US010322096B2

(12) United States Patent
Marcus

(10) Patent No.: US 10,322,096 B2
(45) Date of Patent: Jun. 18, 2019

(54) DISULFIRAM AND METAL SALT STAGGERED ORAL DOSING REGIMEN AND STAGGERED-RELEASE ORAL UNIT DOSAGE FORMS

(71) Applicant: Cantex Pharmaceuticals, Inc., Weston, FL (US)

(72) Inventor: Stephen Marcus, Weston, FL (US)

(73) Assignee: Cantex Pharmaceuticals, Inc., Weston, FL (US)

( * ) Notice: Subject to any disclaimer, the term of this patent is extended or adjusted under 35 U.S.C. 154(b) by 0 days.

(21) Appl. No.: 15/793,879

(22) Filed: Oct. 25, 2017

(65) Prior Publication Data

US 2018/0110744 A1  Apr. 26, 2018

Related U.S. Application Data

(60) Provisional application No. 62/413,257, filed on Oct. 26, 2016, provisional application No. 62/451,597, filed on Jan. 27, 2017, provisional application No. 62/550,500, filed on Aug. 25, 2017.

(51) Int. Cl.

| *A61K 31/145* | (2006.01) |
|---|---|
| *A61P 35/00* | (2006.01) |
| *A61K 31/30* | (2006.01) |
| *A61K 31/495* | (2006.01) |
| *A61K 45/06* | (2006.01) |
| *A61K 33/34* | (2006.01) |

(52) U.S. Cl.
CPC ............ *A61K 31/145* (2013.01); *A61K 31/30* (2013.01); *A61K 31/495* (2013.01); *A61K 33/34* (2013.01); *A61K 45/06* (2013.01); *A61P 35/00* (2018.01); *A61K 2300/00* (2013.01)

(58) Field of Classification Search
CPC ..... A61K 31/145; A61K 31/30; A61K 31/495
See application file for complete search history.

(56) References Cited

U.S. PATENT DOCUMENTS

| 6,548,540 | B2 | 4/2003 | Kennedy |
| 6,589,987 | B2 | 7/2003 | Kennedy |
| 7,816,403 | B2 | 10/2010 | Kennedy |
| 2005/0096304 | A1 | 5/2005 | White et al. |
| 2006/0204578 | A1 | 9/2006 | Vergez et al. |
| 2013/0090591 | A1 | 4/2013 | Ferrara et al. |
| 2014/0037715 | A1* | 2/2014 | Wang ...................... A61K 9/127 424/450 |

FOREIGN PATENT DOCUMENTS

WO    WO 2015/120254 A1    8/2015

OTHER PUBLICATIONS

Allensworth, J., et al., "Disulfiram (DSF) acts as a copper ionophore to induce copper-dependent oxidative stress and mediate anti-tumor efficacy in inflammatory breast cancer," Molecular Oncology, Science Direct, 2015, vol. 9, pp. 1155-1168.

Bobustuc, G., et al., "Disulfiram a dual MGMT and aldehyde dehydrogenase inhibitor sensitizes pancreatic cancer to gemcitabine and abraxane," [Abstract]. Proceedings of the 106th Annual Meeting of the American Association for Cancer Research; Apr. 18-22, 2015, Philadelphia, PA.: AACR; Cancer Res., 2015, vol. 75, Suppl 15, Abstract 3493, 2 Pages.

Brar, S., et al., "Disulfiram inhibits activating transcription factor/ cyclic AMP-responsive element binding protein and human melanoma growth in a metal-dependent manner in vitro, in mice and in a patient with metastatic disease," Molecular Cancer Therapeutics, Sep. 2004, pp. 1049-1060, vol. 3, No. 9.

Burnett, G.B., et al., "The pharmacology of disulfiram in the treatment of alcoholism," Br J Addict Alcohol Other Drugs, 1970, vol. 65, No. 4, pp. 281-288.

Capasso, E., et al., "Role of (64)CuCl2 PET/CT in staging of prostate cancer," Annals of Nuclear Medicine, 2015, vol. 29, No. 6, pp. 482-488.

Chen, D., et al., "Disulfiram, a clinically used anti-alcoholism drug and copper-binding agent, induces apoptotic cell death in breast cancer cultures and xenografts via inhibition of the proteasome activity," Cancer Res., 2006, vol. 66, No. 21, pp. 10425-10433.

Chick, J., "Safety issues concerning the use of disulfiramin treating alcohol dependence," Drug Saf., 1999, vol. 20, No. 5, pp. 427-435.

Child, G. P., et al., "The toxicity of tetraethylthiuram disulphide (Antabuse) to mouse, rat, rabbit and dog," Acta Pharmacol Toxicol (Copenh) 1952, vol. 8, No. 3, pp. 305-314.

Cong, J., et al., "A novel chemoradiation targeting stgem and nonstem pancreatic cancer cells by repurposing disulfiram," Cancer Letters, Aug. 30, 2017, vol. 409, pp. 9-19.

Cvek, B., et al., "Ni(II), Cu(II), and Zn(II) diethyldithiocarbamate complexes show various activities against the proteasome in breast cancer cells," J Med Chem., 2008, vol. 51, No. 20, pp. 6256-6258.

Dalla, P., et al., "Gemcitabine response in pancreatic adenocarcinoma cells is synergistically enhanced by dithiocarbamate derivatives," Free Radical Biology & Medicine, 2011, vol. 50, pp. 926-933.

Denoyer, D., et al., "Copper as a target for prostate cancer therapeutics: copper-ionophore pharmacology and altering systemic copper distribution," Oncotarget, May 9, 2016, vol. 7, No. 24, pp. 37064-37080.

Faiman, M. D., et al., "Distribution of S35 disulfiram and metabolites in mice, and metabolism of S35 disulfiram in the dog," Res Commun Chem Pathol Pharmacol, 1978, vol. 21, No. 3, pp. 543-567.

Faiman, M. D., et al., "Elimination kinetics of disulfiram in alcoholics after single and repeated doses," Clin Pharmacol Ther., 1984, vol. 36, No. 4, pp. 520-526.

(Continued)

*Primary Examiner* — Pancham Bakshi
(74) *Attorney, Agent, or Firm* — Fenwick & West LLP

(57) ABSTRACT

This application relates to methods and compositions for the administration of disulfiram (DSF) and heavy metals zinc and copper for the treatment and prevention of medical conditions, such as cancer. DSF and copper as well as DSF and zinc form active complexes that have been shown to be effective in the treatment of cancers. However, as described herein, DSF is incompatible with either copper or zinc for simultaneous oral administration. Included herein are improved methods and oral dosage forms comprising DSF and copper and DSF and zinc in fixed dose combinations that are configured to temporally stagger release of either DSF and copper or DSF and zinc after ingestion.

2 Claims, 13 Drawing Sheets

(56) References Cited

OTHER PUBLICATIONS

Grossman, K.F., et al., "A phase I clinical study investigating disulfiram and copper gluconate in patients with advanced treatment-refractory solid tumors involving the liver," Cancer Res 71(Suppl 8):[Abstract] nr 1308, 2011, 2 Pages.
Han, J., et al., "A binuclear complex constituted by diethyldithiocarbamate and copper (I) functions as a proteasome activity inhibitor in pancreatic cancer cultures and xenografts," Toxicol Appl. Pharmacol., Dec. 2013, vol. 273, No. 3, pp. 477-483.
Hasinoff, B., et al., "Disulfiram is a slow-binding partial noncompetitive inhibitor of 20S proteasome activity," Arch Biochem Biophys., Sep. 5, 2017, vol. 633, pp. 23-28.
Hochreiter, J., et al., "Disulfiram metabolite S-methyl-N,N-diethylthiocarbamate quantitation in human plasma with reverse phase ultra performance liquid chromatography and mass spectrometry," J Chromatogr B Analyt Technol Biomed Life Sci., May 15, 2012, vol. 897, pp. 80-84.
Hothi, P., et al., "High-throughput chemical screens identify disulfiram as an inhibitor of human glioblastoma stem cells," Oncotarget, Oct. 2012, vol. 3, No. 10, pp. 1124-1136.
Huang, J., et al., "A phase I study to repurpose disulfiram in combination with temozolomide to treat newly diagnosed glioblastoma after chemoradiotherapy," J Neurooncol., Jun. 2016, vol. 128, No. 2, pp. 259-266.
LIjin K., et al., "High-throughput cellbased screening of 4910 known drugs and drug-like small molecules identifies disulfiram as an inhibitor of prostate cancer cell growth," Clin Cancer Res 2009, vol. 15, No. 19, pp. 6070-6078.
Jacobsen, E., "Deaths of alcoholic patients treated with disulfiram (tetraethylthiuram disulfide) in Denmark," Q J Stud Alcohol, 1952, vol. 13, No. 1, pp. 16-26.
Jensen, J. C., et al., Elimination characteristics of disulfiram over time in five alcoholic volunteers: a preliminary study. Am J Psychiatry, Dec. 1982, vol. 139, No. 12, pp. 1596-1598.
Johansson, B., et al., "A review of the pharmacokinetics and pharmacodynamics of disulfiram and its metabolites," Acta Psychiatr Scand Suppl., 1992, vol. 369, pp. 15-26.
Johansson, B., "Plasma protein binding of disulfiram and its metabolite diethylthiocarbamic acid methyl ester," J Pharm Pharmacol, 1990, vol. 42, No. 11, pp. 806-807.
Johansson, B., et al., 1991 "Dose-effect relationship of disulfiram in human volunteers. II: A study of the relation between the disulfiram-alcohol reaction and plasma concentrations of acetaldehyde, diethyldithiocarbamic acid methyl ester, and erythrocyte aldehyde dehydrogenase activity," Pharmacol Toxicol., 1991, vol. 68, No. 3, pp. 166-170.
Kilari, D., et al., "Role of copper transporters in platinum resistance," World J Clin Oncol., Feb. 2016, vol. 7, No. 1, pp. 106-113.
Liu, P., et al., "Cytotoxic effect of disulfiram/copper on human glioblastoma cell lines and ALDH-positive cancer-stem-like cells," Br J Cancer, 2012, vol. 107, No. 9, pp. 1488-1497.
Lun, X., et al., "Disulfiram when combined with copper enhances the therapeutic effects of temozolomide for the treatment of Glioblastoma," Clin Cancer Res., Aug. 1, 2016, vol. 22, No. 15, pp. 3860-3875.
Milandri, M., et al., "Effect of long-term disulfiram administration on rat liver," Pharmacology, 1980, vol. 21, No. 1, pp. 76-80.
Nechushtan, H, et al., "A phase lib trial assessing the addition of disulfiram to chemotherapy for the treatment of metastatic non-small cell lung cancer," Oncologist, 2015, vol. 20, No. 4, pp. 366-367.

Paranjpe, A., et al., "Disulfiram is a direct and potent inhibitor of human O6-methylguanine-DNA methyltransferase (MGMT) in brain tumor cells and mouse brain and markedly increases the alkylating DNA damage," Carcinogenesis, 2014, vol. 35, No. 3, pp. 692-702.
Peng, F., et al., "PET of human prostate cancer xenografts in mice with increased uptake of $^{64}CuCl_2$," Journal of Nuclear Medicine, Jul. 6, 2006, vol. 47, pp. 1649-1652.
Peng, F., et al., "Positron Emission Tomography of Copper Metabolism in the Atp7b-/- knock-out mouse model of Wilson's disease," Molecular Imaging and Biology, Feb. 2012, vol. 14, pp. 70-78.
Petersen, E.N., "The pharmacology and toxicology of disulfiram and its metabolites," Acta Psychiatr Scand Suppl, 1992, vol. 369, pp. 7-13.
Safi, R., et al., "Copper signaling axis as a target for prostate cancer therapeutics," Cancer Research, 2014, vol. 74, No. 20, pp. 5819-5831.
Schweizer, M. T., et al., "Pharmacodynamic study of disulfiram in men with non-metastatic recurrent prostate cancer," Prostate Cancer Prostatic Dis, Dec. 2013, vol. 16, No. 4, pp. 357-361.
Stern, B. R., et al., "Copper and human health: biochemistry, genetics, and strategies for modeling dose-response relationships," J Toxicol Environ Health B Crit Rev., 2007, vol. 10, No. 3, pp. 157-222.
Stewart, D. J., et al., "Phase I study of the combination of disulfiram with cisplatin," Am J Clin Oncol., 1987, vol. 10, No. 6, pp. 517-519.
Suh, J. J., et al., "The status of disulfiram: a half of a century later," J Clin Psychopharmacol., 2006, vol. 26, No. 3, pp. 290-302.
Triscott, J., et al., "Disulfiram, a drug widely used to control alcoholism, suppresses the self-renewal of glioblastoma and overrides resistance to temozolomide," Oncotarget, Oct. 2012, vol. 3, No. 10, pp. 1112-1123.
University of Utah, "Phase I Study of Disulfiram and Copper Gluconate for the Treatment of Refractory Solid Tumors Involving the Liver," NCT00742911 ClinicalTrials.gov, Aug. 28, 2008, 6 Pages, Can be retrieved at <URL:https://clinicaltrials.gov/ct2/show/NCT00742911?term=NCT00742911&>.
Zhang, L., et al., "A novel UPLC-ESI-MS/MS method for the quantitation of disulfiram, its role in stabilized plasma and its application," J Chromatogr B Analyt Technol Biomed Life Sci., 2013, vol. 937, pp. 54-59.
PCT Invitation to Pay Additional Fees and, Where Applicable, Protest Fee for PCT/US17/58358, dated Dec. 27, 2017, 3 Pages.
Lun, X., et al., "Disfulfiram when combined with copper enhances the therapeutic effects of temozolomide for the treatment of glioblastoma," Clinical Cancer Research, Mar. 22, 2016, pp. 3860-3875, vol. 22. No. 15.
PCT International Search Report and Written Opinion for PCT/US17/61362, dated Jan. 30, 2018, 17 Pages.
PCT International Search Report and Written Opinion for PCT/US17/58358, dated Feb. 23, 2018, 22 Pages.
Eisele, S., et al., "Blocking the PD-1/PD-L1 Signaling Pathway in Malignant Glioma: Current and Future Perspectives," OncLive, Aug. 9, 2015, 5 Pages.
Fukai, J., et al., "Rapid regression of glioblastoma following carmustine wafer implantation: A case report," Molecular and Clinical Oncology, 2016, vol. 5, pp. 153-157.
He, J., et al., "Development of $PD_{-1}/PD-L_1$ Pathway in Tumor Immune Microenvironment and Treatment for Non-Small Cell Lung Cancer," Scientific Reports, Aug. 17, 2015, vol. 5, pp. 1-9.
Helson, C., et al., "Androgen receptor antagonists for prostate cancer therapy," Thematic Review, Aug. 1, 2014, vol. 21, pp. T105-T118.
Von Hoff, D., et al., "Increased Survival in Pancreatic Cancer with nab-Paclitaxel plus Gemcitabine," The New England Journal of Medicine, Oct. 31, 2013, pp. 1691-1703.

\* cited by examiner

FIGURE 2: T=0
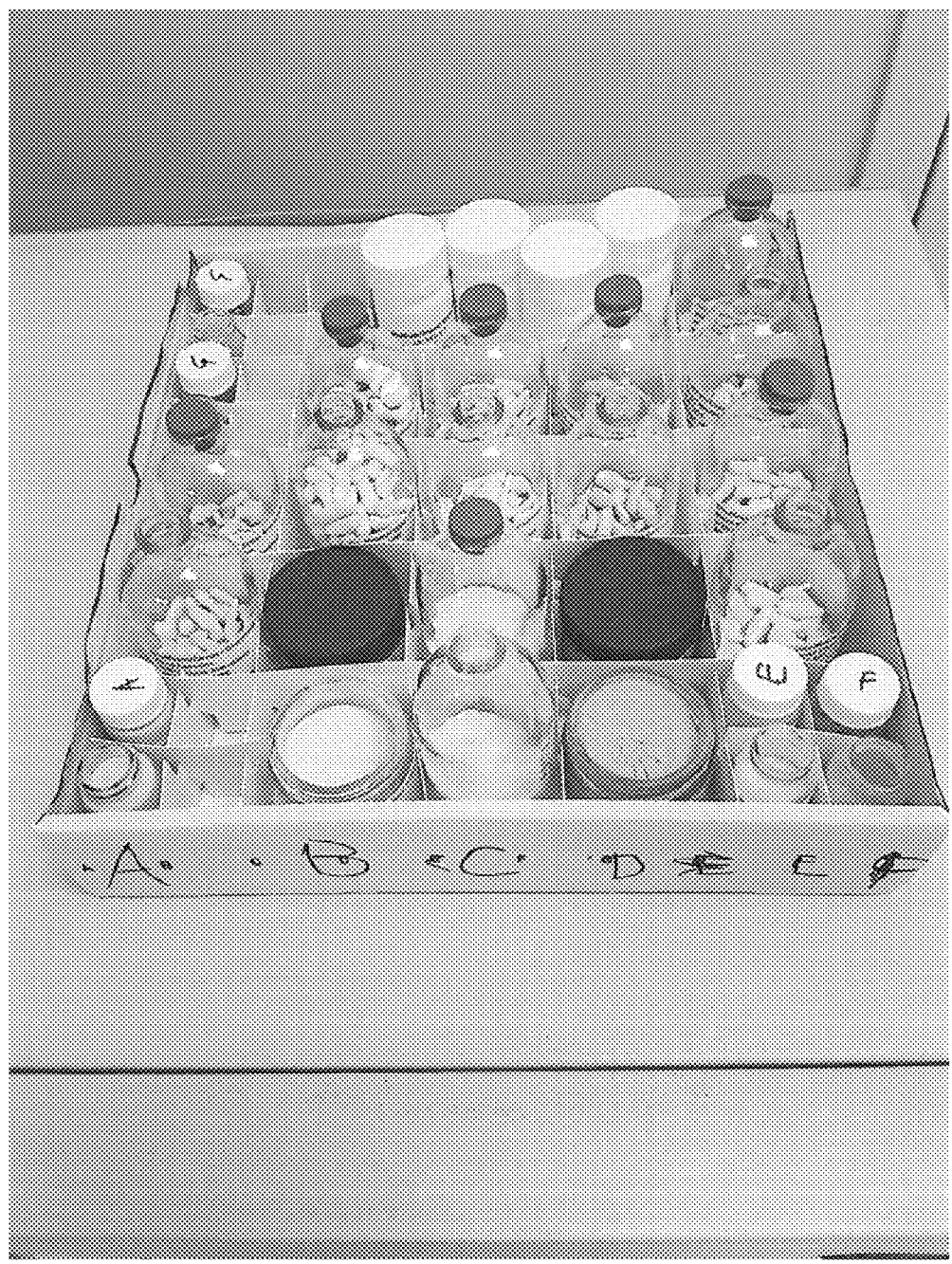

SCHEMA

DISULFIRAM AND METAL SALT STAGGERED ORAL DOSING REGIMEN AND STAGGERED-RELEASE ORAL UNIT DOSAGE FORMS

1. CROSS-REFERENCE TO RELATED APPLICATIONS

This application claims benefit under 35 U.S.C. § 119(e) of U.S. Provisional Application Nos. 62/550,500 filed Aug. 25, 2017; 62/451,597 filed Jan. 31, 2017; and 62/413,257, filed Oct. 26, 2016, the contents of all of which are incorporated herein in their entireties by reference thereto.

2. BACKGROUND

Disulfiram and copper form active complexes that have been shown to be effective in vitro in killing neoplastic cells of various cancers, see, e.g., U.S. Pat. Nos. 6,548,540; 6,589,987; and 7,816,403, and that have been shown to significantly augment temozolomide activity against patient-derived glioma cells from both newly diagnosed and recurrent tumors, both in vitro and in animal models, see Lun et al., Clin. Cancer Res. 22(15):3860-75 (2016). Disulfiram and zinc also form active complexes that kill neoplastic cells in vitro, see, e.g., U.S. Pat. No. 6,548,540. Despite this promise, however, combination therapy with disulfiram and copper and disulfiram and zinc has not yet been proven to be effective in human cancer patients. There is a continuing need for methods, compositions, and dosage forms that allow the preclinical efficacy of combination therapy with disulfiram and copper, and disulfiram and zinc, to be translated into effective human therapies.

3. SUMMARY

It has now been discovered that disulfiram (DSF) and copper are poorly compatible for simultaneous oral administration. Accordingly, disclosed herein are methods for the administration of DSF and copper on a staggered oral dosing schedule for the treatment of hyperproliferative disorders, including cancer, and oral dosage forms configured to temporally stagger release of disulfiram and copper after ingestion. It has also been discovered that disulfiram (DSF) and zinc are poorly compatible for simultaneous oral administration. Disclosed herein are methods for the administration of DSF and zinc on a staggered oral dosing schedule for the treatment of hyperproliferative disorders, including cancer, and oral dosage forms configured to temporally stagger release of disulfiram and zinc after ingestion.

In a first aspect, methods for treating cancer are provided, comprising administering to a subject with cancer an effective amount of DSF followed by or preceded by an effective amount of copper on a temporally staggered dosage schedule.

In an embodiment, the copper is administered prior to administration of DSF. In an embodiment, the DSF is administered prior to administration of copper. In an embodiment, the method comprises administering to a subject an effective amount of an oral dosage form comprising DSF and copper to the subject, wherein the oral dosage form is configured to temporally stagger release of DSF and copper after ingestion. In an embodiment, the subject is human. In an embodiment, the copper is in the form of copper gluconate. In an embodiment, the copper is in the form of copper glycinate. In an embodiment, the DSF is released after the release of copper in the digestive system of the subject. In an embodiment, the DSF is released prior to the release of copper in the digestive system of the subject. In an embodiment, the DSF is formulated to be released in the stomach of the subject and the copper is formulated to be released in the intestines of the subject. In an embodiment, the copper is formulated to be released in the stomach of the subject and the DSF is formulated to be released in the intestines of the subject. In an embodiment, the DSF is formulated to be released in the stomach of the subject and the copper is coated with an enteric coating or a gastro-resistant coating. In an embodiment, the copper is formulated to be released in the stomach of the subject and the DSF is coated with an enteric coating or a gastro-resistant coating. In an embodiment, the oral dosage form consists of a solid pharmaceutical composition. In an embodiment, the oral dosage form consists of a liquid pharmaceutical composition. In an embodiment, the oral dosage form comprises a solid and a liquid pharmaceutical composition. In an embodiment, the liquid pharmaceutical composition comprises DSF. In an embodiment, the liquid pharmaceutical composition comprises DSF and a solvent. In an embodiment, the solvent is hydrophobic. In an embodiment, the solvent is propylene glycol. In an embodiment, oral dosage forms comprising a liquid pharmaceutical composition are administered for the treatment of pediatric cancers. In an embodiment, the oral dosage form comprises at least one polymeric material. In an embodiment, the oral dosage form comprises a hydrophilic matrix. In an embodiment, the oral dosage form comprises a hydrophobic matrix. In an embodiment, the oral dosage form comprises at least one disintegrant. In an embodiment, the oral dosage form further comprises at least one pharmaceutical excipient selected from the group consisting of a polymeric material, a hydrophobic matrix, a hydrophilic matrix and a disintegrant. In an embodiment, the oral dosage form is a solid dosage form comprising more than one layer; and wherein the DSF and copper are located in separate layers. In an embodiment, the oral dosage form comprises at least one additional intermediate layer. In an embodiment, the oral dosage form comprises granules; and wherein the DSF and copper are located in separate granules. In an embodiment, the method comprises administering an effective amount of an anti-cancer agent prior to the administration of the oral dosage form. In an embodiment, the method comprises administering an effective amount of an anti-cancer concurrently with the administration of the oral dosage form. In an embodiment, the method comprises administering an effective amount of an anti-cancer agent after the administration of the oral dosage form. In an embodiment, the oral dosage form further comprises an anti-cancer agent. In an embodiment, the anti-cancer agent is selected from the group consisting of radiation, a chemotherapeutic, a targeted anti-cancer agent, an antibody, a small molecule inhibitor, a chemokine, a nucleic acid and an immunomodulator. In an embodiment, the method is performed for the treatment of cancers selected from the group consisting of glioblastoma, medulloblastoma, prostate cancer, pancreatic cancer, rectal cancer, head and neck cancer, lung cancer, colon cancer, bladder cancer, kidney cancer, liver cancer, breast cancer and osteosarcoma. In an embodiment, the cancer is glioblastoma. In an embodiment, the glioblastoma is temozolomide-resistant. In an embodiment, the cancer is prostate cancer. In an embodiment, the cancer is castration-resistant prostate cancer. In an embodiment, the cancer is pancreatic cancer. In an embodiment, the cancer is inflammatory breast cancer. In an embodiment, administration of the oral dosage form results in reduced tumor burden in the subject. In an embodiment, the administration of the oral dosage form results in increased survival in the subject. In an embodiment, the effective amount of DSF is 10 mg to 1 g. In an embodiment, the amount of DSF in the effective amount is 40 mg. In an embodiment, the amount of DSF in the effective amount is 80 mg. In an embodiment, the effective amount of copper gluconate is 0.1 mg to 30 mg. In an embodiment, the amount of copper gluconate in the oral dosage form is 1.5-2 mg. In an embodiment, the oral dosage form is administered thrice daily.

In an aspect, the application describes an oral dosage form configured to temporally stagger release of DSF and copper after ingestion. In an embodiment, the application describes a differential release dosage form comprising DSF and copper configured to separately release of DSF and copper after ingestion. In an embodiment, the application describes a two-stage release dosage form comprising DSF and copper, configured to separately release of DSF and copper after ingestion. In an embodiment, the copper is in the form of copper gluconate. In an embodiment, the copper is in the form of copper glycinate. In an embodiment, the oral dosage form comprises at least one pharmaceutically acceptable excipient. In an embodiment, the DSF is released after the release of copper. In an embodiment, the DSF is released prior to the release of copper. In an embodiment, the copper is formulated to be released in a subject immediately upon injection. In an embodiment, the oral dosage form is formulated such that copper is released in the digestive system of the subject after the release of DSF. In an embodiment, the copper is formulated to be released in the digestive system of the subject prior to the release of DSF. In an embodiment, the copper is formulated to be released in the digestive system of the subject after the release of the DSF. In an embodiment, the copper is formulated to be released in the digestive system of the subject greater than 30 minutes after the release of DSF. In an embodiment, the DSF is formulated to be released in a subject upon ingestion, and the copper is formulated to be released in the digestive system of the subject greater than 30 minutes after the release of DSF. In an embodiment, the DSF is formulated to be released in the stomach of the subject and the copper is formulated to be released in the intestines of the subject. In an embodiment, the DSF is formulated to be released in the stomach of the subject and wherein the copper is coated with an enteric coating or a gastro-resistant coating. In an embodiment, the release of DSF is completed before the onset of the release of copper. In an embodiment, the release of copper is completed before the onset of the release of DSF.

In an embodiment, the oral dosage form comprises DSF in a solid pharmaceutical composition. In an embodiment, the DSF is in a liquid pharmaceutical composition. In an embodiment, the DSF is in contact with a dispersion agent. In an embodiment, the copper is in a solid pharmaceutical composition. In an embodiment, the copper is in a liquid pharmaceutical composition. In an embodiment, the copper is in contact with a dispersion agent. In an embodiment, the oral dosage form comprises both a solid pharmaceutical composition and a liquid pharmaceutical composition. In an embodiment, the oral dosage form comprises DSF and copper, wherein the DSF and copper are located in different layers.

In an embodiment, the oral dosage form comprises two or more layers. In an embodiment, the oral dosage form comprises two layers. In an embodiment, the DSF is located in an outer layer and the copper is located in an inner layer that is underneath the layer comprising DSF. In an embodiment, the oral dosage form comprises more than two layers.

In an embodiment, the oral dosage form comprises an intermediate layer. In an embodiment, the intermediate layer does not comprise either DSF or copper.

In an embodiment, the oral dosage form comprises one or more types of granules. In an embodiment, the oral dosage form comprises DSF in a first solid pharmaceutical composition formulated as a first type of granule, and copper in a second solid pharmaceutical composition formulated as a second type of granule. In an embodiment, the granules have a size range of 0.01 to 5 mm in diameter. In an embodiment, the oral dosage form comprises at least one polymeric material. In an embodiment, the copper is in contact with a polymeric material. In an embodiment, the DSF is in contact with a polymeric material. In an embodiment, the oral dosage form comprises a disintegrant. In an embodiment, the DSF is in contact with the disintegrant. In an embodiment, the copper is in contact with the disintegrant. In an embodiment, the oral dosage form comprises granules, and the granules comprise copper and a polymeric material. In an embodiment, the oral dosage form comprises granules, and the granules comprise copper and an enteric coating. In an embodiment, the oral dosage form comprises granules, and the granules comprise copper and a disintegrant. In an embodiment, the oral dosage form comprises granules, and the granules comprise DSF and a polymeric material. In an embodiment, the oral dosage form comprises granules, and the granules comprise DSF and an enteric coating. In an embodiment, the oral dosage form comprises granules, and the granules comprise DSF and a disintegrant. In an embodiment, the oral dosage form comprises at least two types of granules, wherein one type of granule comprises DSF and the other type of granule comprises copper. In an embodiment, the oral dosage form comprises at least two types of granules, and at least one type of granule comprises copper, wherein the copper is formulated to be released after DSF, and the oral dosage form further comprises at least one type of granule comprising DSF. In an embodiment, the oral dosage form comprises at least two types of granules, and at least one of the types of granule comprises copper, wherein the copper is formulated to be released after DSF and wherein the granule comprising copper is coated with an enteric coating, and the oral dosage form further comprises at least one type of granule comprising DSF. In certain embodiments, the granules are not spherical. In certain embodiments, the granules are mini-tablets that have a volume between 0.01 $cm^3$ and 3 $cm^3$.

In an embodiment, the oral dosage form is configured so that the DSF is released upon exposure to an acidic solution with a pH less than 4. In an embodiment, the oral dosage form is configured so that the DSF is released upon exposure to a solution with a pH greater than 6. In an embodiment, the oral dosage form is configured so that the copper is released upon exposure to an acidic solution with a pH less than 4. In an embodiment, the oral dosage form is configured so that the copper is released upon exposure to a solution with a pH greater than 6.

In an embodiment, the oral dosage form comprises a hydrophilic matrix. In an embodiment, the oral dosage form comprises a hydrophobic matrix. In an embodiment, the oral dosage form is configured so that the release of DSF is controlled by diffusion of DSF through a pore. In an embodiment, the oral dosage form is configured so that the release of copper is controlled by diffusion of copper through a pore. In an embodiment, the DSF in the oral dosage form is in contact with a gastroretentive composition. In an embodiment, the oral dosage form comprises a semipermeable membrane. In an embodiment, the oral dosage form comprises phospholipids.

In an aspect, the application describes a method of treating cancer comprising administering to a subject an oral dosage form comprising an effective amount of DSF followed by administering an oral dosage form comprising an effective amount of copper. In an embodiment, the application describes a method of treating cancer comprising administering to a subject an oral dosage form comprising an effective amount of copper followed by administering an oral dosage form comprising an effective amount of DSF. In an embodiment, the copper is in the form of copper gluconate. In an embodiment, the oral dosage form comprising copper is administered 30 minutes or more after the administration of the oral dosage form comprising DSF. In an embodiment, the oral dosage form comprising DSF is administered 30 minutes or more after the administration of the oral dosage form comprising copper. In an embodiment, the subject is human. In an embodiment, the DSF is released after the release of copper in the digestive system of the subject. In an embodiment, the DSF is released prior to the release of copper in the digestive system of the subject. In an embodiment, the DSF is formulated to be released in the stomach of the subject, and the copper is formulated to be released in the intestines of the subject. In an embodiment, the copper is formulated to be released in the stomach of the subject, and the DSF is formulated to be released in the intestines of the subject. In an embodiment, the DSF is formulated to be released in the stomach of the subject, and the copper is coated with an enteric coating or a gastro-resistant coating. In an embodiment, the copper is formulated to be released in the stomach of the subject, and the DSF is coated with an enteric coating or a gastro-resistant coating. In an embodiment, at least one of the oral dosage forms is a solid dosage form. In an embodiment, at least one of the oral dosage forms comprises at least one polymeric material. In an embodiment, at least one of the oral dosage forms comprises a hydrophilic matrix. In an embodiment, at least one of the oral dosage forms comprises a hydrophobic matrix. In an embodiment, at least one of the oral dosage forms comprises at least one disintegrant. In an embodiment, at least one of the oral dosage forms comprises at least one pharmaceutical excipient selected from the group consisting of a polymeric material, a hydrophobic matrix, a hydrophilic matrix and a disintegrant. In an embodiment, the oral dosage form is a solid dosage form comprising more than one layer; and the DSF and copper are located in separate layers. In an embodiment, at least one of the oral dosage forms comprises at least one additional intermediate layer. In an embodiment, at least one of the oral dosage forms comprises granules.

In an embodiment, the method comprises administering an effective amount of an anti-cancer agent prior to the administration of the oral dosage forms. In an embodiment, the method comprises administering an effective amount of an anti-cancer concurrently with the administration of the oral dosage forms. In an embodiment, the method comprises administering an effective amount of an anti-cancer agent after the administration of the oral dosage forms. In an embodiment, the oral dosage form further comprises an anti-cancer agent. In an embodiment, the anti-cancer agent is selected form the group consisting of radiation, a chemotherapeutic, a targeted anti-cancer agent, an antibody, a small molecule inhibitor, a chemokine, a nucleic acid, a hormonal agent, and an immunomodulator. In an embodiment, the method is performed for the treatment of cancers selected from the group consisting of glioblastoma, liver cancer, breast cancer and osteosarcoma. In an embodiment, the cancer is glioblastoma. In an embodiment, administration of the oral dosage forms results in reduced tumor burden in the subject. In an embodiment, the administration of the oral dosage forms results in increased survival in the subject.

In an embodiment, the amount of DSF in the oral dosage form ranges from 10 mg to 1 g. In an embodiment, the amount of DSF in the oral dosage form is 80 mg. In an embodiment, the amount of copper gluconate in the oral dosage form is in the range of 0.1 mg to 30 mg. In an embodiment, the amount of copper gluconate in the oral dosage form is 1.5-2 mg. In an embodiment, the oral dosage forms are administered thrice daily.

In an aspect, the application describes a means for administering DSF and copper to a subject for treating cancer, wherein the administration results in release of DSF and copper at different times within the subject.

In an aspect, the application describes a means for administering DSF and copper to a subject for treating cancer, wherein the administration results in release of DSF in the stomach of the subject and release of copper within the intestines of the subject.

In an aspect, the application describes a method of treating cancer comprising administering to a subject with cancer an effective amount of DSF followed by or preceded by administering an effective amount of copper. In an aspect of the method, the subject is administered a first oral dosage form comprising an effective amount of DSF followed by or preceded by administering a second oral dosage form comprising an effective amount of copper. In an embodiment, the copper is in the form of copper gluconate or copper glycinate. In an embodiment, the copper is in the form of copper gluconate. In an aspect of the method, the oral dosage form comprising copper is administered 30 minutes or more after the administration of the oral dosage form comprising DSF. In an aspect of the method, the oral dosage form comprising copper is administered 1 to 2 hours after the administration of the oral dosage form comprising DSF.

In an aspect, the application describes a method of treating cancer comprising administering to a subject with cancer an effective amount of DSF and copper, wherein the DSF and copper are administered together in a single oral dosage form, wherein the oral dosage form is configured to temporally stagger release of DSF and copper after ingestion, wherein the copper is released following the release of DSF in the digestive system of the subject. In an aspect of the method, the DSF is released upon ingestion, and the copper is released in the digestive system of the subject greater than 30 minutes after the release of the DSF. In an embodiment, the DSF is released upon ingestion and the copper is released in the digestive system of the subject 1 to 2 hours after the release of the DSF. In an embodiment, the release of DSF is completed before the onset of release of copper. In an embodiment, the DSF is formulated to be released in the stomach of the subject and the copper is formulated to be released in the intestines of the subject. In an embodiment, the DSF is formulated to be released in the stomach of the subject and the copper is coated with an enteric coating or a gastro-resistant coating. In an embodiment, each oral dosage form consists of at least one pharmaceutical excipient selected from the group consisting of a polymeric material, a hydrophobic matrix, a hydrophilic matrix and a disintegrant. In an embodiment, the oral dosage form comprises a first plurality of granules comprising DSF and a second plurality of granules comprising copper. In an embodiment, the method comprises administering an effective amount of at least one additional anti-cancer agent prior to, concurrently with or after the administration of DSF and copper. In an embodiment, the additional anti-cancer agent is selected from the group consisting of a chemotherapeutic, a targeted anti-cancer agent, an antibody, a small molecule inhibitor, a chemokine, a nucleic acid, an immunomodulator, a hormonal agent, radiation, or combinations thereof. In an embodiment, the additional anti-cancer agent is temozolomide.

In certain embodiments of the methods described in the application, the oral dosage form further comprises an additional anti-cancer agent. In an embodiment, the additional anti-cancer agent is selected from the group consisting of a chemotherapeutic, a targeted anti-cancer agent, an antibody, a small molecule inhibitor, a chemokine, a nucleic acid and an immunomodulator. In an embodiment, the additional anti-cancer agent is temozolomide.

In certain embodiments of the methods, the cancer is selected from the group consisting of glioblastoma, liver cancer, lung cancer, breast cancer, prostate cancer, pancreatic cancer, colon cancer, rectal cancer, colon cancer, bladder cancer, kidney cancer, medulloblastoma, head and neck cancer, and osteosarcoma. In an embodiment, the cancer is glioblastoma. In an embodiment, the glioblastoma is temozolomide-resistant. In an embodiment, the cancer is prostate cancer. In an embodiment, the cancer is castration-resistant prostate cancer. In an embodiment, the cancer is breast cancer. In an embodiment, the cancer is inflammatory breast cancer.

In certain embodiments of the methods, the administration results in reduced tumor burden in the subject. In certain embodiments of the methods, the administration results in wherein the administration results in increased progression-free survival and/or overall survival of the subject.

In certain embodiments, the effective amount of DSF is 10 mg to 1.0 g. In certain embodiments, the effective amount of DSF is 40 mg. In certain embodiments, the effective amount of DSF is 80 mg. In certain embodiments, the effective amount of copper gluconate is in the range of 0.1 mg to 30 mg. In an embodiment, the effective amount of copper gluconate in is 1.5 mg.

In certain embodiments, the oral dosage form comprising DSF is administered thrice daily. In certain embodiments, the oral dosage form comprising copper is administered thrice daily.

In an embodiment, each of the oral dosage forms is a capsule.

In an embodiment, the oral dosage form comprising DSF is a capsule comprising 40 mg-80 mg of DSF; the oral dosage form comprising copper is a capsule comprising 1.5 mg-3 mg copper gluconate; two of the capsules comprising DSF are administered three times daily, and the capsule comprising copper gluconate is administered three times daily.

In an aspect, the application describes an oral dosage form configured to temporally stagger release of DSF and copper after ingestion, wherein the copper is released following the release of DSF. In an aspect, the application describes an oral dosage form configured to temporally stagger release of DSF and copper after ingestion, wherein the DSF is released following the release of copper. In an embodiment, the copper is in the form of copper gluconate or copper glycinate. In an embodiment, the copper is in the form of copper gluconate. In an embodiment, the oral dosage form comprises at least one pharmaceutically acceptable excipient. In an embodiment, the release of DSF is formulated to be followed by the release the copper in the digestive system of the subject. In certain embodiments, the DSF is formulated to be released immediately upon ingestion. In certain embodiments, the copper is formulated to be released in the digestive system of the subject greater than 30 minutes after the release of DSF. In an embodiment, the copper is formulated to be released in the digestive system of the subject in the range of 1-3 hours after the release of DSF. In an embodiment, the DSF is formulated to be released in the stomach of the subject, and the copper is formulated to be released in the intestines of the subject. In an embodiment, the DSF is formulated to be released in the stomach of the subject, and the copper is coated with an enteric coating or a gastro-resistant coating. In certain embodiments, the release of DSF is completed before the onset of the release of copper. In certain embodiments, the DSF is in a solid pharmaceutical composition. In certain embodiments, the copper is in a solid pharmaceutical composition. In certain embodiments, each solid pharmaceutical composition is formulated as a granule, optionally as a minitablet. In certain embodiments, the granules or minitablets are 0.01 mm to 5 mm in maximum diameter. In certain embodiments, the DSF is in a first solid pharmaceutical composition formulated as a first type of granule, optionally as a first type of minitablet, and the copper is in a second solid pharmaceutical composition formulated as a second type of granule, optionally as a first type of minitablet. In certain embodiments, the oral dosage form contains 10 mg to 1.0 g DSF. In an embodiment, the oral dosage form contains 80 mg DSF. In an embodiment, the oral dosage form contains 40 mg DSF. In certain embodiments, the oral dosage form contains 0.1 mg-30 mg of copper. In an embodiment, the oral dosage from contains 1.5 mg of copper.

In an aspect, the application describes an oral dosage form configured to temporally stagger release of 80 mg of DSF followed and 1.5 mg copper after ingestion, wherein the dosage form is a capsule comprising a first population of granules, optionally minitablets, comprising DSF and a second population of granules, optionally minitablets, comprising copper gluconate and wherein the copper granules or minitablets are formulated to be released 1-3 hours after the release of DSF.

In an aspect, the application describes a method of treating glioblastoma comprising administering to a patient with Temozolomide-resistant glioblastoma a first oral dosage form comprising an effective amount of DSF followed by administering a second oral dosage form comprising an effective amount of copper wherein the first oral dosage form comprising DSF is a capsule comprising 40 mg-80 mg of DSF; wherein the second oral dosage form comprising copper is a capsule comprising 1.5 mg-3 mg copper gluconate; wherein two of the capsules comprising DSF are administered three times daily on a 28-day cycle; wherein the capsule comprising copper gluconate is administered three times daily on a 28-day cycle; and wherein temozolomide is administered daily on days 1-5 of a 28 day cycle at a dose of 150 mg/m$^2$.

In certain aspects, the application discloses methods of treating a condition, comprising administering to a subject with the condition an effective amount of DSF followed by administering an effective amount of copper. In certain embodiments, the methods comprise administering to the subject a first oral dosage form comprising an effective amount of DSF followed by administering a second oral dosage form comprising an effective amount of copper. In certain embodiments, the copper is in the form of copper gluconate or copper glycinate. In an embodiment, the copper is in the form of copper gluconate. In certain embodiments, the oral dosage form comprising copper is administered 30 minutes or more after the administration of the oral dosage form comprising DSF. In an embodiment, the oral dosage form comprising copper is administered 1 to 3 hours after the administration of the oral dosage form comprising DSF.

In certain aspects, the application discloses methods of treating a condition, comprising administering to a subject with the condition an effective amount of DSF and copper, wherein the DSF and copper are administered together in a single oral dosage form, wherein the oral dosage form is configured to temporally stagger release of DSF and copper after ingestion, wherein the copper is released following the release of DSF in the digestive system of the subject. In certain embodiments, the DSF is released upon ingestion, and the copper is released in the digestive system of the subject greater than 30 minutes after the release of the DSF. In certain embodiments, the DSF is released upon ingestion and the copper is released in the digestive system of the subject 1 to 3 hours after the release of the DSF. In certain embodiments, the release of DSF is completed before the onset of release of copper. In an embodiment, the DSF is formulated to be released in the stomach of the subject and the copper is formulated to be released in the intestines of the subject. In an embodiment, the DSF is formulated to be released in the stomach of the subject and the copper is coated with an enteric coating or a gastro-resistant coating. In certain embodiments, the condition is an infection. In an embodiment, the condition is tuberculosis.

In an embodiment, the application describes methods of preventing cancer in a subject, comprising administering to the subject an effective amount of DSF followed by administering an effective amount of copper. In certain embodiments, the methods comprise administering to the subject a first oral dosage form comprising an effective amount of DSF followed by administering a second oral dosage form comprising an effective amount of copper. In certain embodiments, the copper is in the form of copper gluconate or copper glycinate. In an embodiment, the copper is in the form of copper gluconate. In certain embodiments, the oral dosage form comprising copper is administered 30 minutes or more after the administration of the oral dosage form comprising DSF. In an embodiment, the oral dosage form comprising copper is administered 1 to 3 hours after the administration of the oral dosage form comprising DSF.

In an aspect, the application discloses a method of preventing cancer in a subject, comprising administering to the subject an effective amount of DSF and copper, wherein the DSF and copper are administered together in a single oral dosage form, wherein the oral dosage form is configured to temporally stagger release of DSF and copper after ingestion, wherein the copper is released following the release of DSF in the digestive system of the subject. In certain embodiments, DSF is released upon ingestion, and the copper is released in the digestive system of the subject greater than 30 minutes after the release of the DSF. In an embodiment, the DSF is released upon ingestion and the copper is released in the digestive system of the subject 1 to 3 hours after the release of the DSF. In certain embodiments, the release of DSF is completed before the onset of release of copper. In an embodiment, the DSF is formulated to be released in the stomach of the subject and the copper is formulated to be released in the intestines of the subject. In certain embodiments, the DSF is formulated to be released in the stomach of the subject and the copper is coated with an enteric coating or a gastro-resistant coating. In certain embodiments, the subject has previously been diagnosed with cancer. In certain embodiments, the method prevents the recurrence of cancer. In certain embodiments, the subject has previously been treated for cancer. In certain embodiments, the subject has previously been treated for cancer with surgery, radiation therapy, an anti-cancer agent or combinations thereof.

In an aspect, methods for treating cancer are provided, comprising administering to a subject with cancer an effective amount of DSF and an effective amount of zinc on a temporally staggered dosage schedule. In an aspect, the application describes a method of treating cancer comprising administering to a subject with cancer an effective amount of DSF followed by or preceded by administering an effective amount of zinc. In an aspect of the method, the subject is administered a first oral dosage form comprising an effective amount of DSF followed by or preceded by administering a second oral dosage form comprising an effective amount of zinc. In an embodiment, the zinc is in the form of zinc gluconate or zinc glycinate. In an embodiment, the zinc is in the form of zinc gluconate. In an aspect of the method, the oral dosage form comprising zinc is administered 30 minutes or more after the administration of the oral dosage form comprising DSF. In an aspect of the method, the oral dosage form comprising zinc is administered 1 to 3 hours after the administration of the oral dosage form comprising DSF.

In an aspect, the application describes a method of treating cancer comprising administering to a subject with cancer an effective amount of DSF and zinc, wherein the DSF and zinc are administered together in a single oral dosage form, wherein the oral dosage form is configured to temporally stagger release of DSF and zinc after ingestion, wherein the zinc is released following the release of DSF in the digestive system of the subject. In an aspect of the method, the DSF is released upon ingestion, and the zinc is released in the digestive system of the subject greater than 30 minutes after the release of the DSF. In an embodiment, the DSF is released upon ingestion and the zinc is released in the digestive system of the subject 1 to 3 hours after the release of the DSF. In an embodiment, the release of DSF is completed before the onset of release of zinc. In an embodiment, the DSF is formulated to be released in the stomach of the subject and the zinc is formulated to be released in the intestines of the subject. In an embodiment, the DSF is formulated to be released in the stomach of the subject and the zinc is coated with an enteric coating or a gastro-resistant coating. In an embodiment, each oral dosage form further comprises at least one pharmaceutical excipient selected from the group consisting of a polymeric material, a hydrophobic matrix, a hydrophilic matrix and a disintegrant. In an embodiment, the oral dosage form comprises a first plurality of granules comprising DSF and a second plurality of granules comprising zinc. In an embodiment, the method comprises administering an effective amount of an additional anti-cancer agent prior to, concurrently with or after the administration of DSF and zinc. In an embodiment, the additional anti-cancer agent is selected from the group consisting of a chemotherapeutic, a targeted anti-cancer agent, an antibody, a small molecule inhibitor, a chemokine, a nucleic acid and an immunomodulator. In an embodiment, the additional anti-cancer agent is temozolomide.

In certain embodiments of the methods described in the application, the oral dosage form further comprises an additional anti-cancer agent. In an embodiment, the additional anti-cancer agent is selected from the group consisting of a chemotherapeutic, a targeted anti-cancer agent, an antibody, a small molecule inhibitor, a chemokine, a nucleic acid and an immunomodulator. In an embodiment, the additional anti-cancer agent is temozolomide.

In certain embodiments of the methods, the cancer is selected from the group consisting of glioblastoma, prostate cancer, pancreatic cancer, liver cancer, lung cancer, breast cancer, prostate cancer and osteosarcoma. In an embodiment, the cancer is glioblastoma. In an embodiment, the glioblastoma is temozolomide-resistant. In an embodiment, the cancer is prostate cancer. In an embodiment, the cancer is castration-resistant prostate cancer. In an embodiment, the cancer is pancreatic cancer. In an embodiment, the cancer is breast cancer. In an embodiment, the cancer is inflammatory breast cancer.

In certain embodiments of the methods, the administration results in reduced tumor burden in the subject. In certain embodiments of the methods, the administration results in wherein the administration results in increased progression-free survival and/or overall survival of the subject.

In certain embodiments, the effective amount of DSF ranges from 10 mg to 1.0 g. In certain embodiments, the effective amount of DSF is 80 mg. In certain embodiments, the effective amount of DSF is 40 mg. In certain embodiments, the effective amount of zinc gluconate is in the range of 10 mg to 300 mg. In an embodiment, the effective amount of zinc gluconate in is 50 mg.

In certain embodiments, the oral dosage form comprising DSF is administered thrice daily. In certain embodiments, the oral dosage form comprising zinc is administered thrice daily.

In an embodiment, each of the oral dosage forms is a capsule.

In an embodiment, the oral dosage form comprising DSF is a capsule comprising 40 mg-80 mg of DSF; the oral dosage form comprising zinc is a capsule comprising 10 mg-300 mg zinc gluconate; two of the capsules comprising DSF are administered three times daily, and the capsule comprising zinc gluconate is administered three times daily.

In an aspect, the application describes an oral dosage form configured to temporally stagger release of DSF and zinc after ingestion, wherein the zinc is released following the release of DSF. In an aspect, the application describes an oral dosage form configured to temporally stagger release of DSF and zinc after ingestion, wherein the DSF is released following the release of zinc. In an embodiment, the zinc is in the form of zinc gluconate or zinc glycinate. In an embodiment, the zinc is in the form of zinc gluconate. In an embodiment, the oral dosage form comprises at least one pharmaceutically acceptable excipient. In an embodiment, the release of DSF is formulated to be followed by the release the zinc in the digestive system of the subject. In certain embodiments, the DSF is formulated to be released immediately upon ingestion. In certain embodiments, the zinc is formulated to be released in the digestive system of the subject greater than 30 minutes after the release of DSF. In an embodiment, the zinc is formulated to be released in the digestive system of the subject in the range of 1-3 hours after the release of DSF. In an embodiment, the DSF is formulated to be released in the stomach of the subject, and the zinc is formulated to be released in the intestines of the subject. In an embodiment, the DSF is formulated to be released in the stomach of the subject, and the zinc is coated with an enteric coating or a gastro-resistant coating. In certain embodiments, the release of DSF is completed before the onset of the release of zinc. In certain embodiments, the DSF is in a solid pharmaceutical composition. In certain embodiments, the zinc is in a solid pharmaceutical composition. In certain embodiments, the solid pharmaceutical composition is formulated as a granule. In certain embodiments, the granules have a size range of 0.01 mm to 5 mm in maximum diameter. In certain embodiments, the DSF is in a first solid pharmaceutical composition formulated as a first type of granule, and the zinc is in a second solid pharmaceutical composition formulated as a second type of granule. In certain embodiments, the effective amount of DSF is in the range of 10 mg to 1.0 g. In an embodiment, the dosage form contains 40 mg of DSF. In an embodiment, the dosage form contains 80 mg of DSF. In certain embodiments, the dosage form contains 10 mg-300 mg of zinc. In an embodiment, the dosage form contains 50 mg of zinc.

In an aspect, the application describes an oral dosage form configured to temporally stagger release of DSF and zinc after ingestion; wherein the dosage form is a capsule comprising a first population of granules, optionally minitablets, comprising DSF and a second population of granules, optionally minitablets, comprising zinc gluconate and wherein the zinc granules or minitablets are formulated to be release zinc 1-3 hours after the release of DSF.

In an aspect, the application describes a method of treating glioblastoma comprising administering to a patient with temozolomide-resistant glioblastoma a first oral dosage form comprising an effective amount of DSF followed by administering a second oral dosage form comprising an effective amount of zinc, wherein the first oral dosage form comprising DSF is a capsule comprising 40 mg-80 mg of DSF; wherein the second oral dosage form comprising zinc is a capsule comprising 10 mg-300 mg zinc gluconate; wherein two of the capsules comprising DSF are administered three times daily on a 28-day cycle; wherein the capsule comprising zinc gluconate is administered three times daily on a 28-day cycle; and wherein temozolomide is administered daily on days 1-5 of a 28 day cycle at a dose of 150 mg/m$^2$.

In certain aspects, the application discloses methods of treating a condition, comprising administering to a subject with the condition an effective amount of disulfiram ("DSF") followed by administering an effective amount of zinc. In certain embodiments, the methods comprise administering to the subject a first oral dosage form comprising an effective amount of DSF followed by administering a second oral dosage form comprising an effective amount of zinc. In certain embodiments, the zinc is in the form of zinc gluconate or zinc glycinate. In an embodiment, the zinc is in the form of zinc gluconate. In certain embodiments, the oral dosage form comprising zinc is administered 30 minutes or more after the administration of the oral dosage form comprising DSF. In an embodiment, the oral dosage form comprising zinc is administered 1 to 3 hours after the administration of the oral dosage form comprising DSF.

In certain aspects, the application discloses methods of treating a condition, comprising administering to a subject with the condition an effective amount of DSF and zinc, wherein the DSF and zinc are administered together in a single oral dosage form, wherein the oral dosage form is configured to temporally stagger release of DSF and zinc after ingestion, wherein the zinc is released following the release of DSF in the digestive system of the subject. In certain embodiments, the DSF is released upon ingestion, and the zinc is released in the digestive system of the subject greater than 30 minutes after the release of the DSF. In certain embodiments, the DSF is released upon ingestion and the zinc is released in the digestive system of the subject 1 to 3 hours after the release of the DSF. In certain embodiments, the release of DSF is completed before the onset of release of zinc. In an embodiment, the DSF is formulated to be released in the stomach of the subject and the zinc is formulated to be released in the intestines of the subject. In an embodiment, the DSF is formulated to be released in the stomach of the subject and the zinc is coated with an enteric coating or a gastro-resistant coating. In certain embodiments, the condition is an infection. In an embodiment, the condition is tuberculosis.

In an embodiment, the application describes methods of preventing cancer in a subject, comprising administering to the subject an effective amount of DSF followed by administering an effective amount of zinc. In certain embodiments, the methods comprise administering to the subject a first oral dosage form comprising an effective amount of DSF followed by administering a second oral dosage form comprising an effective amount of zinc. In certain embodiments, the zinc is in the form of zinc gluconate or zinc glycinate. In an embodiment, the zinc is in the form of zinc gluconate. In certain embodiments, the oral dosage form comprising zinc is administered 30 minutes or more after the administration of the oral dosage form comprising DSF. In an embodiment, the oral dosage form comprising zinc is administered 1 to 3 hours after the administration of the oral dosage form comprising DSF.

In an aspect, the application discloses a method of preventing cancer in a subject, comprising administering to the subject an effective amount of DSF and zinc, wherein the DSF and zinc are administered together in a single oral dosage form, wherein the oral dosage form is configured to temporally stagger release of DSF and zinc after ingestion, wherein the zinc is released following the release of DSF in the digestive system of the subject. In certain embodiments, DSF is released upon ingestion, and the zinc is released in the digestive system of the subject greater than 30 minutes after the release of the DSF. In an embodiment, the DSF is released upon ingestion and the zinc is released in the digestive system of the subject 1 to 3 hours after the release of the DSF. In certain embodiments, the release of DSF is completed before the onset of release of zinc. In an embodiment, the DSF is formulated to be released in the stomach of the subject and the zinc is formulated to be released in the intestines of the subject. In certain embodiments, the DSF is formulated to be released in the stomach of the subject and the zinc is coated with an enteric coating or a gastro-resistant coating. In certain embodiments, the subject has previously been diagnosed with cancer. In certain embodiments, the method prevents the recurrence of cancer. In certain embodiments, the subject has previously been treated for cancer. In certain embodiments, the subject has previously been treated for cancer with surgery, radiation therapy, an anti-cancer agent or combinations thereof.

In certain aspects, described herein is an oral unit dosage form, comprising a capsule containing at least one of disulfiram minitablet and at least one copper minitablet, wherein each disulfiram minitablet comprises a core, wherein the core contains disulfiram and one or more excipients, and a first coating external to the core, wherein the first external coating does not delay release of disulfiram after capsule ingestion; wherein each copper minitablet comprises a core, wherein the core contains copper gluconate and/or copper glycinate, and one or more excipients; optionally, a first coating external to the core, and a second coating external to the optional first coating, wherein the second external coating effects delayed release of copper after capsule ingestion. In certain embodiments, the capsule is a hard gelatin capsule or a soft gelatin capsule. In certain embodiments, the disulfiram minitablets within a capsule collectively contain 20 mg DSF, 30 mg DSF, 40 mg DSF, 50 mg DSF, 60 mg DSF, 70 mg DSF, 80 mg DSF, 90 mg DSF, 100 mg DSF, or 120 mg DSF. In certain embodiments, the disulfiram minitablets within a capsule collectively contain 80 mg DSF. In certain embodiments, each individual disulfiram minitablet contains 2 mg, 4 mg, 6 mg, 8 mg, 10 mg, 12 mg, 14 mg, 15 mg, 16 mg DSF, 20 mg DSF, 25 mg DSF, or 40 mg DSF. In certain embodiments, each disulfiram minitablet contains 20 mg DSF. In certain embodiments, the at least one of the DSF minitablet excipients is selected from the group consisting of colloidal silicon dioxide, anhydrous lactose, magnesium stearate, microcrystalline cellulose, sodium starch glycolate, and stearic acid.

In certain embodiments, the disulfiram first external coating is an aqueous film coating. In certain embodiments, the disulfiram first external coating is pH-insensitive. In certain embodiments, the disulfiram first external coating comprises low viscosity hydroxypropyl methylcellulose (HPMC), plasticizers or optional pigments, or combinations thereof. In certain embodiments, the disulfiram first external coating comprises Opadry®. In certain embodiments, the disulfiram first external coating comprises Opadry® II. In certain embodiments, the disulfiram first external coating comprises Opadry® II 85. In certain embodiments, the disulfiram first external coating comprises sodium carboxymethylcellulose (NaCMC). In certain embodiments, the disulfiram first external coating comprises polyvinyl alcohol (PVA). In certain embodiments, the disulfiram first external coating comprises Opadry® AMB. In certain embodiments, the disulfiram first external coating is present at a thickness, measured as minitablet weight gain upon application, of 1%, 2%, 3%, 4%, 5%, 6%, 7%, 8%, 9%, or 10%.

In certain embodiments, the copper minitablets within a capsule collectively contain 0.1 mg copper, 0.2 mg copper, 0.25 mg copper, 0.3 mg copper, 0.4 mg copper, 0.5 mg copper, 0.75 mg copper, 1 mg copper, 1.5 mg copper, 2 mg copper or 2.5 mg copper. In certain embodiments, the copper minitablets within a capsule collectively contain 1.5 mg copper. In certain embodiments, each copper minitablet contains 0.1 mg copper, 0.2 mg copper, 0.3 mg copper, 0.4 mg copper, 0.5 mg copper, 0.6 mg copper, 0.7 mg copper, 0.8 mg copper, 0.9 mg copper, or 1.0 mg copper. In certain embodiments, each individual copper minitablet contains 0.5 mg copper. In certain embodiments, the optional copper first external coating is an aqueous film coating. In certain embodiments, the optional copper first external coating is pH-insensitive.

The oral unit dosage form of any one of claims 179-201, wherein the optional copper first external coating comprises low viscosity hydroxypropyl methylcellulose (HPMC), plasticizers, optional pigments, or combinations thereof. In certain embodiments, the optional copper first external coating is Opadry®. In certain embodiments, wherein the optional copper first external coating is Opadry® II. In certain embodiments, the optional copper first external coating is Opadry® II 85. In certain embodiments, wherein the optional copper first external coating comprises sodium carboxymethylcellulose (NaCMC). In certain embodiments, the optional copper first external coating comprises polyvinyl alcohol (PVA). In certain embodiments, the optional copper first external coating is Opadry® AMB. In certain embodiments, the optional copper first external coating is present at a thickness, measured as minitablet weight gain upon application, of 1%, 2%, 3%, 4%, 5%, 6%, 7%, 8%, 9%, or 10%. In certain embodiments, the optional copper first external coating is present at a thickness, measured as minitablet weight gain upon application of 2%.

In certain embodiments, the copper second external coating is a pH-sensitive delayed release coating. In certain embodiments, the copper second external coating dissolves at pH >=5.0. In certain embodiments, the copper second external coating dissolves at pH >=5.5. In certain embodiments, the copper second external coating is an aqueous acrylate/methacrylate copolymer. In certain embodiments, the copper second external coating comprises Eudragit® L 100-55. In certain embodiments, the copper second external coating comprises AcrylEZE®. In certain embodiments, the copper second external coating is present at a thickness, measured as minitablet weight gain upon application, of 1%, 2.5%, 5%, 7.5%, 10%, 11%, 12%, 13%, 14%, 15%, 16%, 17%, 18%, 19%, 20%, 21%, 22%, 23%, 24%, or 25%. In certain embodiments, the copper second external coating is present at a thickness, measured as minitablet weight gain upon application, of 20%. In certain embodiments, the copper second external coating is a pH-insensitive time-controlled release coating. In certain embodiments, the copper second external coating comprises Eudragit® RS. In certain embodiments, the copper second external coating comprises Eudragit® RL. In certain embodiments, the copper second external coating dissolves at pH >=7. In certain embodiments, the copper second external coating comprises Eudragit® FS.

In certain embodiments, the copper is further coated with a third coating external to the second coating, wherein the third external coating effects delayed release of copper after capsule ingestion. In certain embodiments, the copper third external coating is a pH-sensitive delayed release coating. In certain embodiments, the copper third external coating dissolves at pH >=7. In certain embodiments, the copper third external coating comprises Eudragit® FS. In certain embodiments, the copper third external coating is a pH-insensitive time-controlled release coating. In certain embodiments, the copper third external coating comprises Eudragit® RS. In certain embodiments, the copper third external coating comprises Eudragit® RL.

In an aspect, described herein is an oral unit dosage form, comprising a capsule containing at least one of disulfiram minitablet and at least one zinc minitablet, wherein each disulfiram minitablet comprises a core, wherein the core contains disulfiram and one or more excipients, and a first coating external to the core, wherein the first external coating does not delay release of disulfiram after capsule ingestion; wherein each zinc minitablet comprises a core, wherein the core contains zinc gluconate and/or zinc glycinate, and one or more excipients; optionally, a first coating external to the core, and a second coating external to the optional first coating, wherein the second external coating effects delayed release of zinc after capsule ingestion.

In an aspect, described herein is a method of treating pancreatic cancer, comprising administering to a patient with metastatic pancreatic cancer a first oral dosage form comprising an effective amount of DSF followed by or preceded by administering a second oral dosage form comprising an effective amount of copper, wherein the first oral dosage form comprising DSF is a capsule comprising 40 mg-80 mg of DSF; the second oral dosage form comprising copper is a capsule comprising 1.5 mg-3 mg copper gluconate; two of the capsules comprising DSF are administered three times daily on a 28-day cycle; the capsule comprising copper gluconate is administered three times daily on a 28-day cycle; the capsule comprising copper gluconate is not administered within one hour of the capsules comprising DSF; and administering to the patient Nab-paclitaxel intravenously over 30 minutes at a dose of 125 mg/m$^2$ followed by administering gemcitabine intravenously over 30 minutes at a dose of at 1000 mg/m$^2$; wherein Nab-paclitaxel and gemcitabine are administered weekly for 3 weeks followed by one week of no administration of Nab-paclitaxel and gemcitabine.

In an aspect, described herein is a method of treating pancreatic cancer, comprising administering to a patient with metastatic pancreatic cancer a first oral dosage form comprising an effective amount of DSF followed by or preceded by administering a second oral dosage form comprising an effective amount of zinc, wherein the first oral dosage form comprising DSF is a capsule comprising 40 mg-80 mg of DSF; the second oral dosage form comprising zinc is a capsule comprising 10 mg-300 mg zinc gluconate; two of the capsules comprising DSF are administered three times daily on a 28-day cycle; the capsule comprising zinc gluconate is administered three times daily on a 28-day cycle; the capsule comprising zinc gluconate is not administered within one hour of the capsules comprising DSF; and administering to the patient Nab-paclitaxel intravenously over 30 minutes at a dose of 125 mg/m$^2$ followed by administering gemcitabine intravenously over 30 minutes at a dose of at 1000 mg/m$^2$; and wherein Nab-paclitaxel and gemcitabine are administered weekly for 3 weeks followed by one week of no administration of Nab-paclitaxel and gemcitabine.

In an aspect, described herein is a method of adjuvant treatment of malignant glioma or other primary malignant brain tumor, including but not limited to glioblastoma, comprising administering to a patient with malignant glioma a first oral dosage form comprising an effective amount of DSF followed by or preceded by administering a second oral dosage form comprising an effective amount of copper; wherein the first oral dosage form comprising DSF is a capsule comprising 40 mg-80 mg of DSF; wherein the second oral dosage form comprising copper is a capsule comprising 1.5 mg-3 mg copper gluconate; wherein two of the capsules comprising DSF are administered three times daily on a 28-day cycle; wherein the capsule comprising copper gluconate is administered three times daily on a 28-day cycle; wherein the capsule comprising copper gluconate is not administered within one hour of the capsules comprising DSF; and administering to the patient at least one anti-cancer agent over a period of 2-8 weeks concurrent with administration of the first and second oral dosage forms. In certain embodiments, at least one anti-cancer agent is selected from the group consisting of radiation, temozolomide, a nitrosourea including but not limited to BCNU and CCNU, and combinations thereof, or an immunomodulator including, but not limited to PDL-1 and PD-1 antagonists.

In an aspect, described herein is a method of treating rectal cancer, comprising administering to a patient with locally advanced rectal cancer a first oral dosage form comprising an effective amount of DSF followed by or preceded by administering a second oral dosage form comprising an effective amount of copper, wherein the first oral dosage form comprising DSF is a capsule comprising 40 mg-80 mg of DSF; wherein the second oral dosage form comprising copper is a capsule comprising 1.5 mg-3 mg copper gluconate; wherein two of the capsules comprising DSF are administered three times daily on a 28-day cycle; wherein the capsule comprising copper gluconate is administered three times daily on a 28-day cycle; wherein the capsule comprising copper gluconate is not administered within one hour of the capsules comprising DSF; and administering to the patient at least one anti-cancer agent over a period of 2-8 weeks concurrent with administration of the first and second oral dosage forms. In certain embodiments, at least one anti-cancer agent is selected from the group consisting of, 5-fluorouracil, capecitabine, radiation, and combinations thereof.

In an aspect, described herein is a method of treating prostate cancer, comprising administering to a patient with locally advanced prostate cancer a first oral dosage form comprising an effective amount of DSF followed by or preceded by administering a second oral dosage form comprising an effective amount of copper; wherein the first oral dosage form comprising DSF is a capsule comprising 40 mg-80 mg of DSF; wherein the second oral dosage form comprising copper is a capsule comprising 1.5 mg-3 mg copper gluconate; wherein two of the capsules comprising DSF are administered three times daily on a 28-day cycle; wherein the capsule comprising copper gluconate is administered three times daily on a 28-day cycle; wherein the capsule comprising copper gluconate is not administered within one hour of the capsules comprising DSF; administering to the patient radiation, and optionally administering to the patient hormonal therapy. In certain embodiments, the hormonal therapy is an androgen receptor agonist.

In an aspect, described herein is a method of treating head and neck cancer, comprising administering to a patient with locally advanced head and neck cancer a first oral dosage form comprising an effective amount of DSF followed by or preceded by administering a second oral dosage form comprising an effective amount of copper, wherein the first oral dosage form comprising DSF is a capsule comprising 40 mg-80 mg of DSF; wherein the second oral dosage form comprising copper is a capsule comprising 1.5 mg-3 mg copper gluconate; wherein two of the capsules comprising DSF are administered three times daily on a 28-day cycle; wherein the capsule comprising copper gluconate is administered three times daily on a 28-day cycle; wherein the capsule comprising copper gluconate is not administered within one hour of the capsules comprising DSF; and administering to the patient at least one anti-cancer agent over a period of 2-8 weeks concurrent with administration of the first and second oral dosage forms. In certain embodiments, at least one anti-cancer agent is selected from the group consisting of radiation, cisplatin, carboplatin, 5-fluorouracil, and combinations thereof.

In an aspect, described herein is a method of treating lung cancer, comprising administering to a patient with locally advanced lung cancer a first oral dosage form comprising an effective amount of DSF followed by or preceded by administering a second oral dosage form comprising an effective amount of copper; wherein the first oral dosage form comprising DSF is a capsule comprising 40-80 mg of DSF; wherein the second oral dosage form comprising copper is a capsule comprising 1.5 mg-3 mg copper gluconate; wherein two of the capsules comprising DSF are administered three times daily on a 28-day cycle; wherein the capsule comprising copper gluconate is administered three times daily on a 28-day cycle; wherein the capsule comprising copper gluconate is not administered within one hour of the capsules comprising DSF; and administering to the patient at least one anti-cancer agent over a period of 2-8 weeks concurrent with administration of the first and second oral dosage forms. In certain embodiments, the at least one anti-cancer agent is selected from the group consisting of radiation, cisplatin, paclitaxel, immunotherapy, PD-1 antagonists, PDL-1 antagonists, and combinations thereof.

In an aspect, described herein is a method of adjuvant treatment of malignant glioma or other primary malignant brain tumor, comprising administering to a patient with malignant glioma a first oral dosage form comprising an effective amount of DSF followed by or preceded by administering a second oral dosage form comprising an effective amount of copper, wherein the first oral dosage form comprising DSF is a capsule comprising 40 mg-80 mg of DSF; the second oral dosage form comprising copper is a capsule comprising 1.5 mg-3.0 mg copper gluconate; one or two of the capsules comprising DSF are administered three times daily on a 28-day cycle; the capsule(s) comprising copper gluconate is administered three times daily on a 28-day cycle; the capsule(s) comprising copper gluconate is not administered within one hour of the capsules comprising DSF; and administering to the patient at least one anti-cancer agent over a period of 2-8 weeks, followed by treatment with an anti-cancer agent for up to a subsequent 6-12 months, concurrent with administration of the first and second oral dosage forms. In certain embodiments, the at least one anti-cancer agent is selected from the group consisting of radiation, temozolomide, a nitrosourea including, an immunomodulator, and combinations thereof. In certain embodiments, the nitrosourea is bis-chloroethylnitrosourea (BCNU), 1-(2-chloroethyl)-3-cyclohexyl-1-nitrosourea (CCNU), or combinations thereof. In certain embodiments, the immunomodulator is a PD-1 antagonist, a PDL-1 antagonist, or combinations thereof.

4. BRIEF DESCRIPTION OF THE SEVERAL VIEWS OF THE DRAWINGS

These and other features, embodiments, and advantages of the present invention will become better understood with regard to the following description, and accompanying drawings where:

FIG. 2 is a photograph showing bottles containing blends of disulfiram and copper gluconate with (i) individual test excipients, (ii) the full excipient mixture, and (iii) as a simple mixture without excipients, as bulk powders and as capsules stored with and without a desiccant in sealed polypropylene bottles at time zero of the disulfiram stability study. The stability of these blends was visually and analytically evaluated over two weeks at storage conditions of 25, 40 and 50 degrees centigrade.

Figure 3:
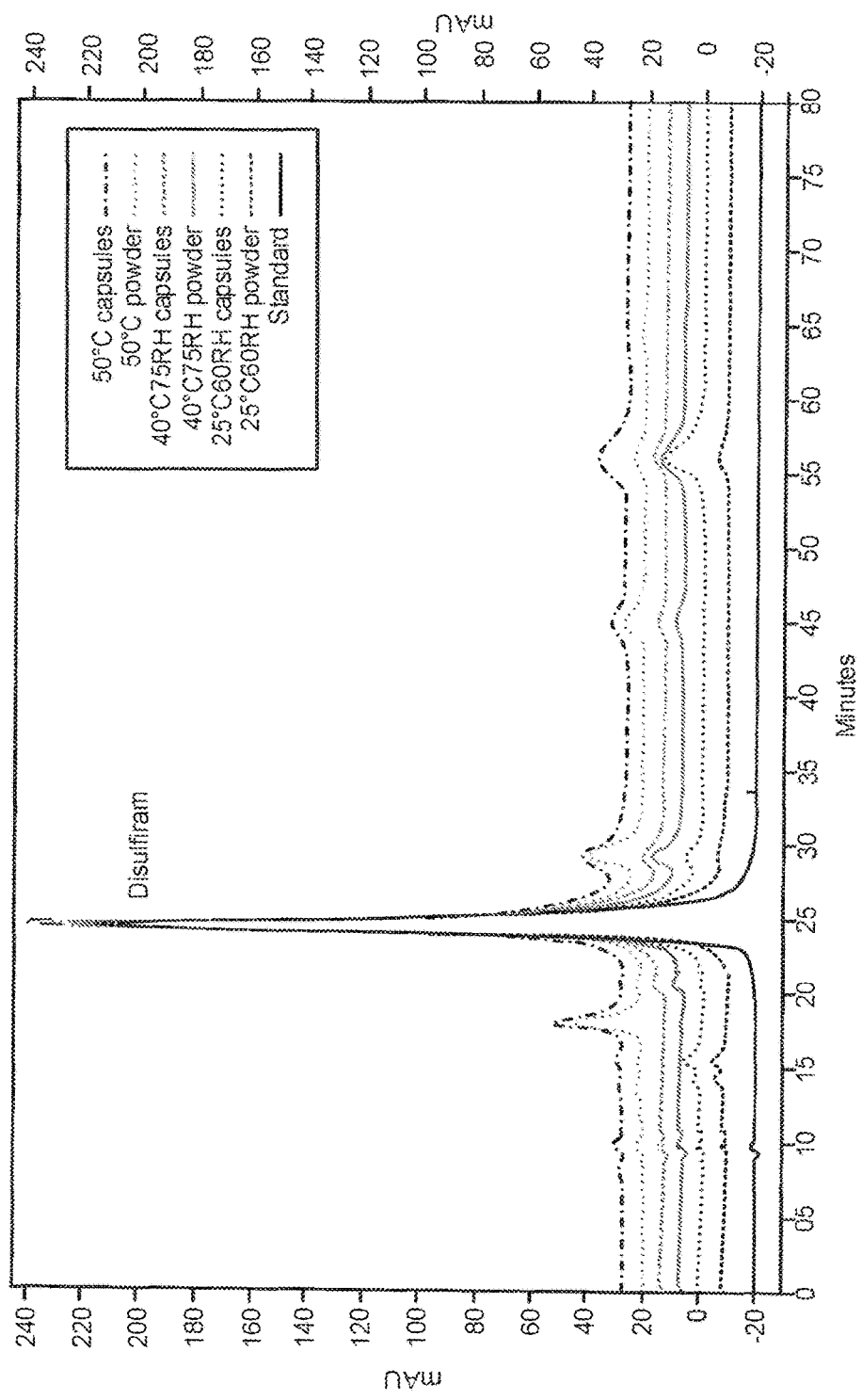

FIG. 3 is a chromatogram of samples of the disulfiram, copper gluconate and lactose anhydrous blend stored in powder and in capsule form at 25° C., 40° C. and 50° C. at the indicated relative humidity ("RH").

Figure 4:
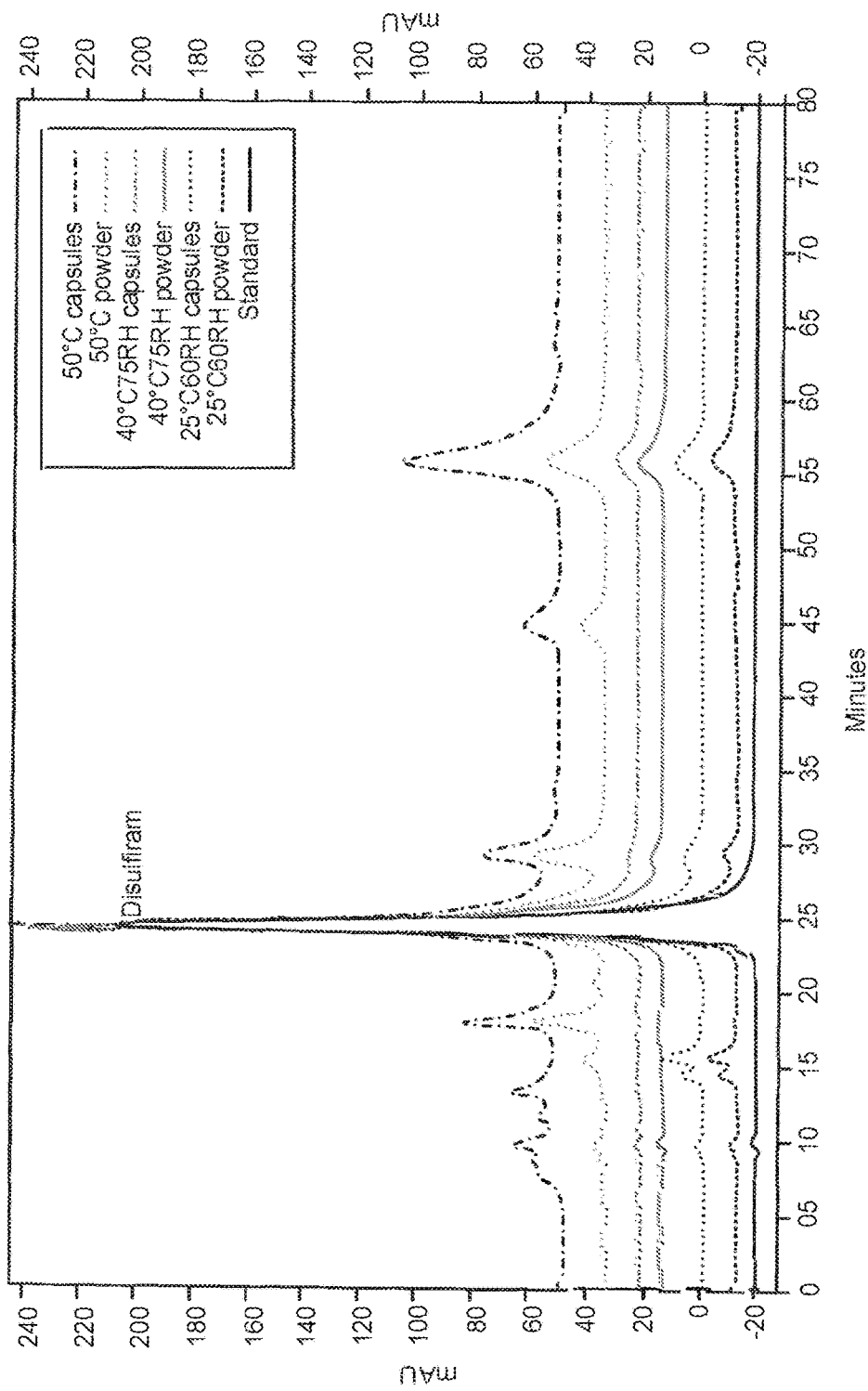

FIG. 4 is a chromatogram of samples of the disulfiram and copper gluconate blend stored in powder and in capsule form at 25° C., 40° C. and 50° C. at the indicated relative humidity ("RH").

Figure 5:
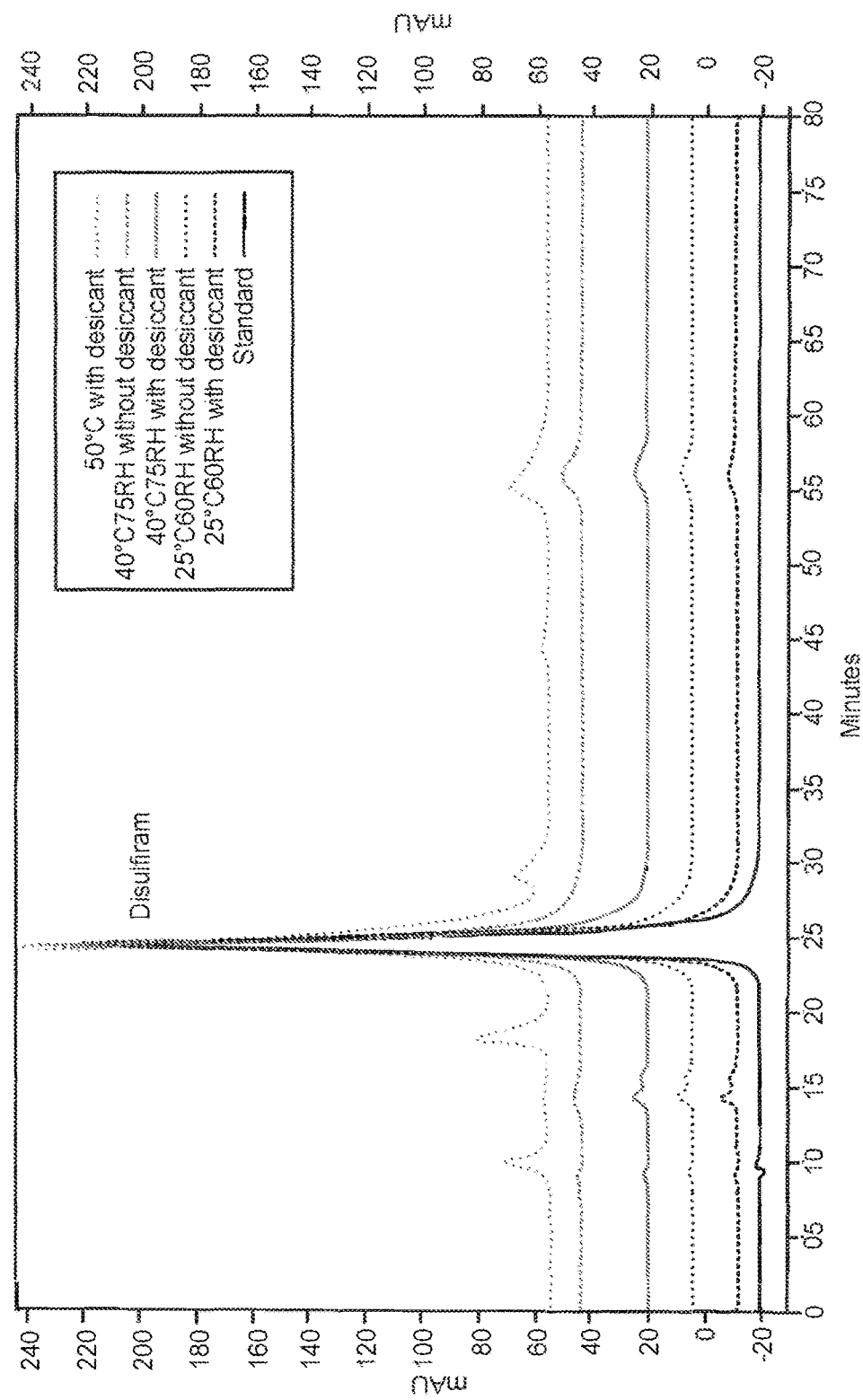

FIG. 5 is a chromatogram of samples of the full blend formulation of disulfiram and copper gluconate stored in powder and in capsule form at 25° C., 40° C. or 50° C. at the indicated relative humidity ("RH").

Figure 6:
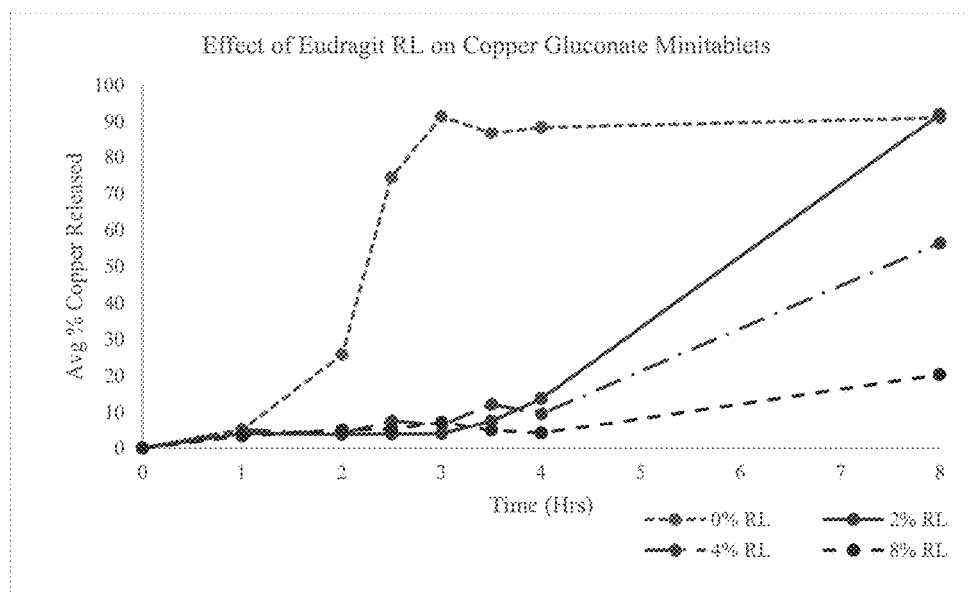

FIG. 6 is a graph showing the average percent copper released from copper gluconate minitablets coated with Eudragit® ("RL").

Figure 7:
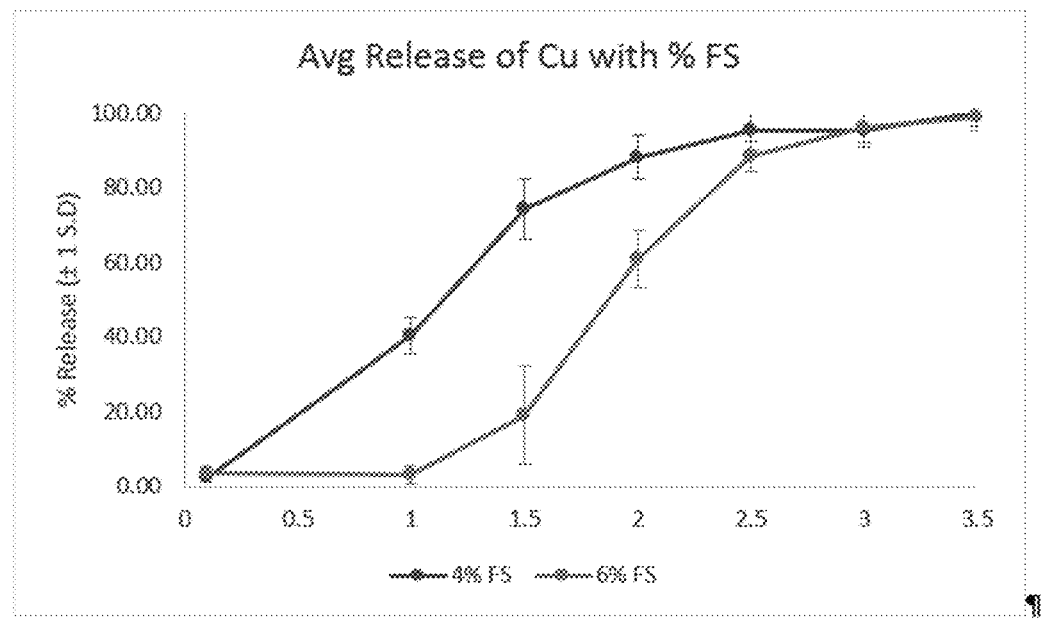

FIG. 7 is a graph showing the average percent copper released from copper gluconate minitablets coated with Eudragit® FS 30D ("FS").

Figure 8:
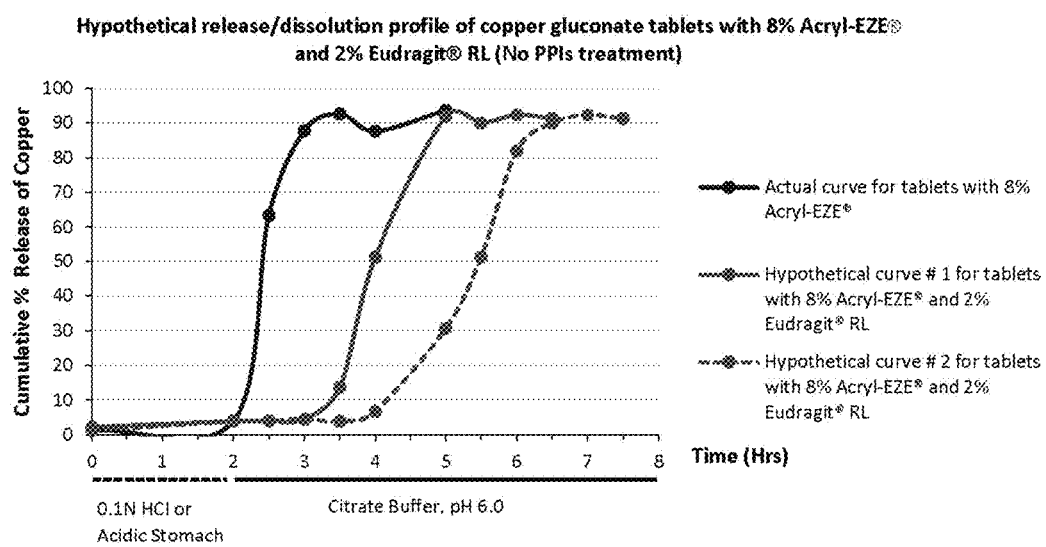

FIG. 8 is a graph showing the hypothetical dissolution profile of copper gluconate coated with 8% Acryl-EZE® and 2% Eudragit® RL.

Figure 9:
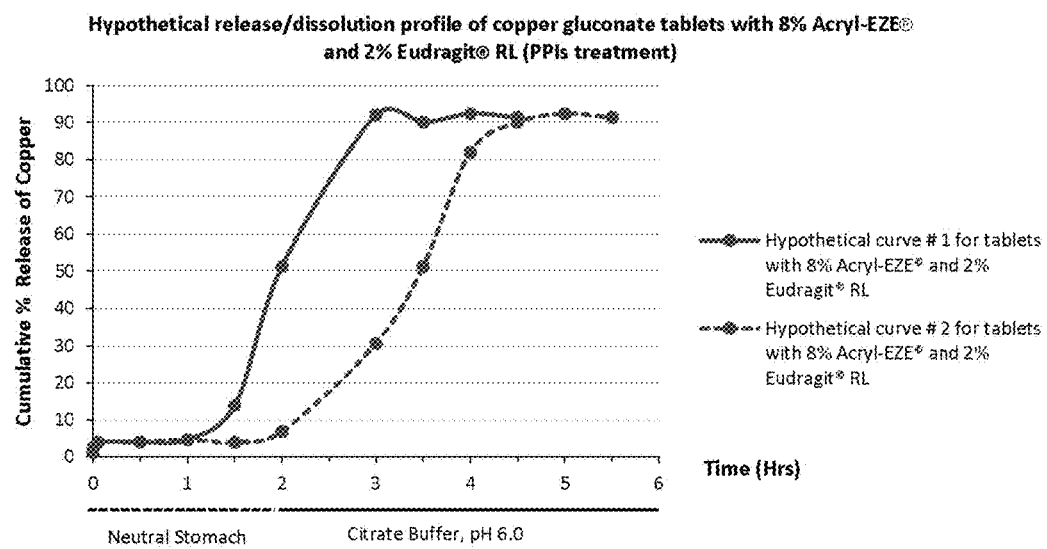

FIG. 9 is a graph showing the hypothetical dissolution profile of copper gluconate coated with 8% Acryl-EZE® and 2% Eudragit® RL in patients receiving proton pump inhibitor (PPI) treatment.

Figure 10:
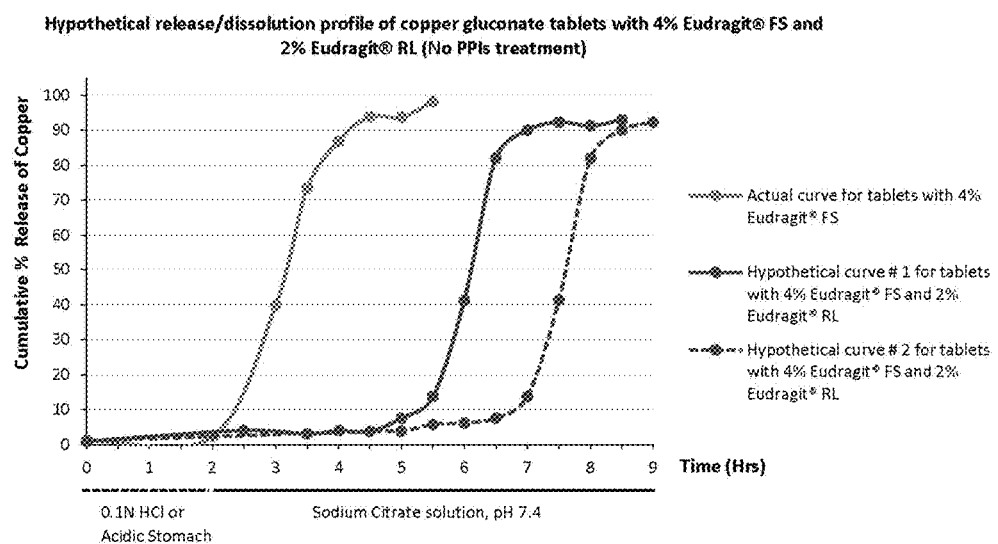

FIG. 10 is a graph showing the hypothetical dissolution profile of copper gluconate coated with 4% Eudragit® FS and 2% Eudragit® RL.

Figure 11:
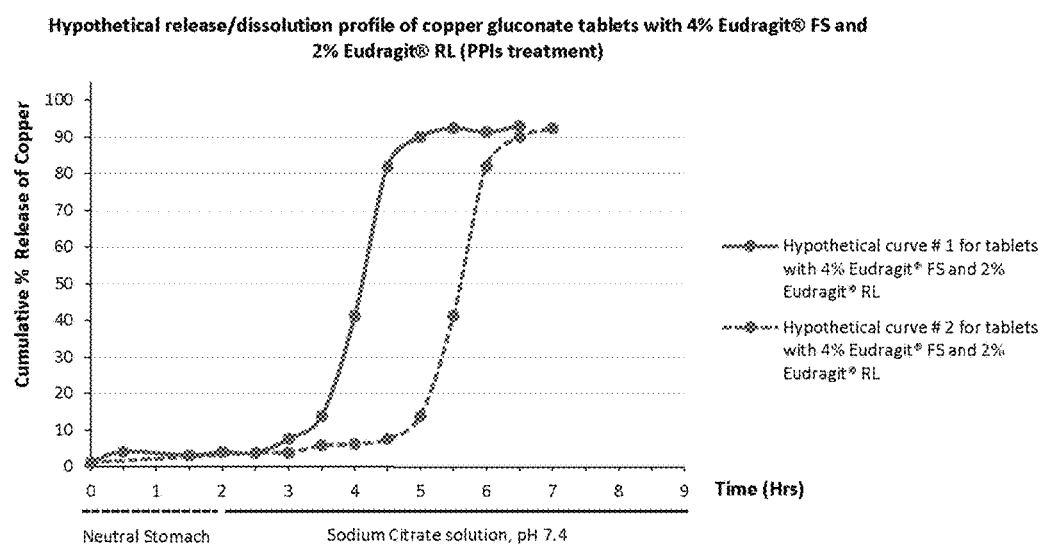

FIG. 11 is a graph showing the hypothetical dissolution profile of copper gluconate coated with 4% Eudragit® FS and 2% Eudragit® RL in patients receiving proton pump inhibitor (PPI) treatment.

Figure 12:
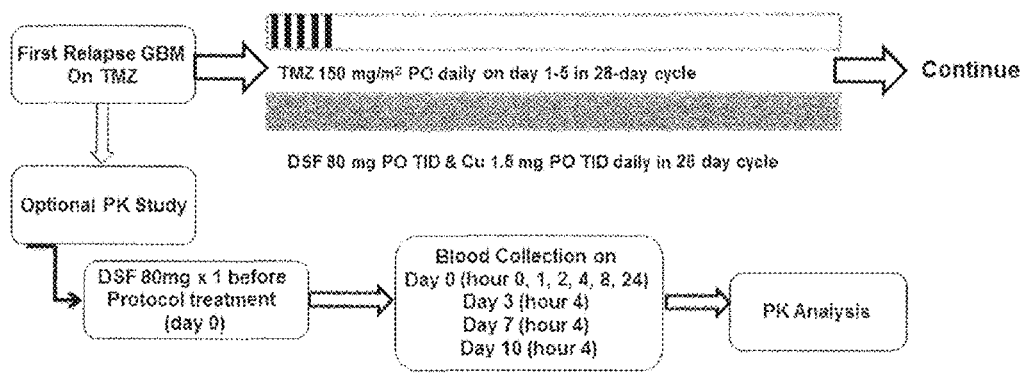

FIG. 12 schematizes the clinical trial protocol for treatment of temozolomide (TMZ) resistant glioblastoma comprising staggered oral dosing of disulfiram (DSF) and copper in combination with TMZ.

Figure 13:
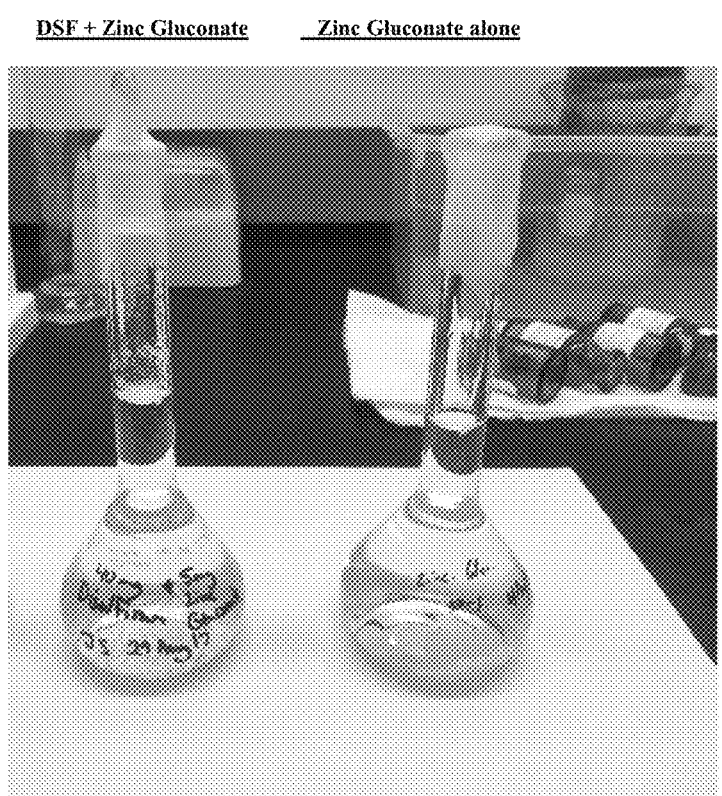

FIG. 13 is a photograph showing flasks containing disulfiram and zinc gluconate (left) and zinc gluconate alone (right), both in 0.1 N HCL.

5. DETAILED DESCRIPTION

5.1. Advantages and Utility

Disulfiram forms complexes with metals, such as copper or zinc; the dithiocarbamate metal complexes have been shown to be effective in vitro and in animal models to inhibit cancer cell growth and/or survival. However, as described herein, it has now been discovered that disulfiram and copper are poorly compatible for simultaneous oral administration. Accordingly, described herein are methods for the oral administration of disulfiram (DSF) and copper on a staggered oral dosing regimen, and oral dosage forms configured to temporally stagger release of disulfiram (DSF) and copper after ingestion, for the treatment of cancer. It has also been discovered that disulfiram and zinc are poorly compatible for simultaneous oral administration. Accordingly, described herein are methods for the oral administration of disulfiram (DSF) and zinc on a staggered oral dosing regimen, and oral dosage forms configured to temporally stagger release of disulfiram (DSF) and zinc after ingestion, for the treatment of cancer.

5.2. Definitions

Unless otherwise defined herein, all technical and scientific terms used herein have the meaning commonly understood by one of ordinary skill in the art to which the invention pertains. The following terms are defined as set forth below.

The term "oral dosage form" refers to a pharmaceutical formulation suitable for oral administration of a defined quantity of one or more active ingredients. In certain embodiments, the oral dosage form comprises a plurality of discrete compositions.

The term "release" or "released" refers to the separation of an agent, typically an active pharmaceutical ingredient ("API"), from the dosage form within which it is administered to a subject, such that the agent is available for absorption. Unless specifically indicated (such as, e.g., by reference to "temporally staggered release"), the term "release" or "released" comprises (i) the onset or beginning of the release; (ii) partial release, and (iii) completion of release, wherein only a negligible or ineffective amount of the drug remains within the dosage form and unavailable for absorption.

The term "temporally staggered release" or "staggered release" refers to the onset of release of one or more agents after or prior to the onset of release of another agent in a pharmaceutical composition.

The term "granule" refers to a solid particle of a pharmaceutical composition that comprises at least one active pharmaceutical ingredient. Granules can be any shape, including spherical or substantially spherical. Granules can be in the form of a tablet or minitablet. Granules can have a volume in any range of 0.001 $mm^3$ to 1.5 $cm^3$. Spherical or substantially spherical granules can have a radius of between 0.01 μm and 1.0 cm.

The term "effective amount" or "therapeutically effective amount" or "sufficient amount" means an amount sufficient to produce a desired effect, e.g., an amount sufficient to reduce tumor burden or reduce disease or stabilize disease or reduce disease symptoms in a subject or an amount that is effective to ameliorate a symptom of a disease.

The term "treating cancer" as used herein, specifically refers to administering therapeutic agents to a patient diagnosed with cancer, i.e., having established cancer in the patient, to inhibit the further growth or spread of the malignant cells in the cancerous tissue and/or to cause the death of malignant cells, or a patient in whom a cancer has been previously treated with potentially curative surgery, radiation, or other treatments and in whom the goal of treatment is to reduce the risk of cancer recurrence, or a patient at known high risk of developing a new cancer for whom the goal is cancer prevention.

The term "preventing cancer" as used herein, refers to administering to a subject with a therapeutic agent for the purpose of inhibiting the onset of cancer or for the purpose of preventing the recurrence of cancer in a patient previously diagnosed with cancer. The subject may be a patient that has been determined to have a higher than average probability of developing cancer than individuals of similar age. The subject may have undergone any diagnostic procedure known in the art for determining the probability of developing cancer. The subject may have undergone prior cancer treatment. For example, the subject may have undergone cancer treatment with an anti-cancer agent, surgery or combinations thereof.

The term "anti-cancer agent" as used herein, refers to any agent or therapeutic used in the art for the treatment of cancer and/or cancer-related conditions. Examples of anti-cancer agents include, but are not limited to, radiation, chemotherapeutics such as, but not limited to: platinum compounds (e.g., cisplatin or carboplatin), alkylating agents (e.g., temozolomide), antitumor antibiotics, taxanes (e.g., paclitaxel), antimetabolites, nucleoside analogues (e.g., 5-fluorouracil and capecitabine), topoisomerase inhibitors, hypomethylating agents, proteasome inhibitors, epipodophyllotoxins, DNA synthesis inhibitors, *vinca* alkaloids, targeted cancer therapeutics, such as but not limited to, tyrosine kinase inhibitors, monoclonal antibodies, nitrosoureas (e.g., bis-chloroethylnitrosourea or 1-(2-chloroethyl)-3-cyclohexyl-1-nitrosourea), enzymes, biological agents (e.g., interferons and interleukins), hexamethylmelamine, mitotane, angiogenesis inhibitors, steroids, hormonal agents (e.g., androgen receptor antagonists), aromatase inhibitors, PARP inhibitors, arsenic trioxide, tretinoin, nonselective cyclooxygenase inhibitors, selective cyclooxygenase-2 (COX-2) inhibitors, immunomodulator (e.g., PD1 antagonists or PDL-1 antagonists), or any combination thereof.

The terms "temozolomide-resistant glioblastoma" or "glioblastoma that is temozolomide-resistant" as used herein refer interchangeably to primary or secondary glioblastoma, astrocytoma or oligodendroglioma in which the subject harboring the cancer has completed a course of temozolomide treatment (either with or without concurrent radiation therapy) and has pathological verification of recurrent tumors.

"DSF" refers to disulfiram, bis(diethylthiocarbamoyl) disulfide or tetraethylthiuram disulfide.

As used herein, "DSF copper complex" refers to a copper 1,1-dithiolato complex.

As used herein, "DSF zinc complex" refers to a zinc 1,1-dithiolato complex.

The term "condition" as used herein, refers to any medical condition or any form of illness or abnormality in a subject that reduces a subject's survival, interferes with usual activities or behavior or feeling of wellbeing. The condition may be, for example, an infection (e.g., bacterial or viral infection), a disease or a disorder. The condition may be inherited or acquired, or susceptibility to developing the condition may be inherited or acquired.

The term "enteric coating" or "gastro-resistant coating" refers to substances applied to the outer surfaces of capsules or tablets (including minitablets, etc.) that inhibit release of substances in the stomach. "pH-sensitive coatings" are impervious or semi-impervious to stomach acid but dissolve in the more alkaline environment of the intestines or colon. In certain embodiments, the enteric coating is methacrylic acid copolymer type C. "pH-insensitive coatings" are enteric coatings that are acid-insoluble or partially acid-soluble and allow for a delay of release of substances in a time-dependent manner (e.g., a coating that exhibits pH independent swelling), allowing for substance release to bypass the stomach and release in either the intestines or colon.

The term "minitablet" or "mini-tablet" refers to solid dosage tablet forms configured to be in a size ≤5 mm in diameter or ≤5 mm on a side.

The term "optional first coating", or "optional first external coating" refers to a coating that is optionally applied external to the core (the core comprising DSF, copper and/or zinc) and internal to the second external coating. In the absence of the optional first coating, the second external coating is the coating that is closest to the exterior of the core.

Unless stated otherwise, as used herein, the term "copper" refers to copper in either the elemental form or in the form of a copper salt (e.g., copper gluconate or copper glycinate).

Unless stated otherwise, the term, "mg Cu" or "mg copper", refers to the mass of elemental copper in the form of copper gluconate or copper glycinate.

Unless stated otherwise, as used herein, the term "zinc" refers to zinc in either the elemental form or in the form of a zinc salt (e.g., zinc gluconate, zinc glycinate or zinc sulfate).

Unless stated otherwise, the term "mg Zn" or "mg zinc", refers to the mass of elemental copper in the form of copper gluconate or copper glycinate.

Recitation of ranges herein includes the recited endpoints and all points there between.

It must be noted that, as used in the specification and the appended claims, the singular forms "a," "an" and "the" include plural referents unless the context clearly dictates otherwise.

5.3. Staggered Oral Dosing Regimens

In a first aspect, methods of treating hyperproliferative disorders, such as cancer, are presented. In certain aspects, method of treating subjects with conditions that would benefit from the treatment of DSF and copper are presented. In certain aspects, methods of preventing cancer or a hyperproliferative disorder in a subject are presented. The methods comprise administering to a subject with cancer, a hyperproliferative disorder or other condition or administering to a subject suspected of having a high probability of developing cancer, a hyperproliferative disorder or other condition an effective amount of DSF and an effective amount of copper on a temporally staggered dosage schedule.

In certain embodiments, the methods comprise administering an effective amount of an oral dosage form comprising DSF preceded by or followed by administration an effective amount of an oral dosage form comprising copper. In some embodiments, the oral dosage form comprising copper is administered prior to administration of the oral dosage form comprising DSF. In embodiments that are currently preferred, the DSF oral dosage form is administered prior to administration of the copper oral dosage form. In certain embodiments, the copper oral dosage form is administered not less than one hour before the administration of the DSF oral dosage form. In certain embodiments, the copper oral dosage form is administered not less than one hour after the administration of the DSF oral dosage form.

In a variety of embodiments, DSF and copper are administered together in a single oral dosage form, wherein the oral dosage form is configured to temporally stagger release of disulfiram (DSF) and copper after ingestion. In various embodiments, release of DSF is preceded by or followed by release of copper. In embodiments that are currently preferred, DSF is released prior to release of copper. Such staggered-release oral dosage forms are described herein further below.

5.3.1. Cancers

The present application describes effective methods for treating or preventing various types of hyperproliferative conditions and cancers of adults and children, including but not limited to: glioblastoma (glioblastoma, astrocytoma or oligodendroglioma), medulloblastoma, atypical teratoid or rhabdoid tumors, ependymoma, pituitary adenoma, melanoma, non-small cell lung cancer, small cell lung cancer, renal cancer, colorectal cancer, breast cancer, triple-negative breast cancer, inflammatory breast cancer, pancreatic cancer, rectal cancer, head and neck cancer, gastric cancer, bladder cancer, kidney cancer, colon cancer, ovarian cancer, uterine cancer, lymphoma, and prostate cancer. In particular, the present invention is effective in treating glioblastoma, melanoma, lung cancer, triple-negative breast cancer and prostate cancer. The present application describes effective methods for treating primary malignant brain tumors, such as, but not limited to, malignant glioma.

In certain embodiments, the methods are used for the treatment of glioblastoma. In certain embodiments, the methods are used for the treatment of temozolomide-resistant glioblastoma. In certain embodiments, the methods of the application are used for the treatment of primary malignant brain tumors. In certain embodiments, the methods of the application are used for the treatment of malignant glioma. In certain embodiments, the methods of the application are used for the treatment of pancreatic cancer. In certain embodiments, the methods of the application are used for the treatment of rectal cancer. In certain embodiments, the methods of the application are used for the treatment of head and neck cancer. In certain embodiments, the methods of the application are used for the treatment of lung cancer. In certain embodiments, the methods of the application are used for the treatment of metastatic pancreatic cancer. In certain embodiments, the methods of the application are used for the treatment of inflammatory breast cancer. In certain embodiments, the methods of the application are used for the treatment of Her2 positive breast cancer. In certain embodiments, the methods of the application are used for the treatment of castration-resistant prostate cancer. In certain embodiments, the methods of the application are used for the treatment of acute myelogenous leukemia (AML). In certain embodiments, the methods of the application are used for the treatment of acute lymphoblastic leukemia (ALL). In certain embodiments, the methods of the application are used for the treatment of esophageal cancer. In certain embodiments, the methods of the application are used for the treatment of mesothelioma. In certain embodiments, the cancer is recurrent cancer that has failed one or more prior anti-cancer treatments. In certain embodiments, the subject has unresectable brain metastases. In certain embodiments, the subject has not yet undergone a prior anti-cancer treatment. In certain embodiments, the cancer is a pediatric cancer. In certain embodiments, the cancer is a pediatric brain tumor including, but not limited to, glioma, medulloblastoma, pituitary adenoma, atypical teratoid or rhabdoid tumor or ependymoma.

In certain aspects, methods of treating disorders or conditions that would benefit from the treatment of DSF and copper are presented. In certain embodiments, the condition is an infection. In certain embodiments, the methods described herein comprise administering DSF and copper for the treatment of tuberculosis. In certain embodiments, the methods described herein comprise administering DSF and copper for the treatment of leishmaniasis.

In the methods described herein, a therapeutically effective amount of DSF is administered. In certain embodiments, the therapeutically effective amount of DSF is 0.01-0.1 mg, 0.1-1 mg, 1.0-10.0 mg, 10.0-20 mg, 20-30 mg, 30-40 mg, 40-50 mg, 50-60 mg, 60-70 mg, 70-80 mg, 80-90 mg, 90-100 mg, 100-150 mg, 150-200 mg, 200-300 mg, 300-400 mg, 400-500 mg or 500-1,000 mg. In an embodiment, the therapeutically effective amount of DSF administered is 80 mg. In an embodiment, the therapeutically effective amount of DSF administered is 40 mg.

In the methods described herein, a therapeutically effective amount of copper is administered. In typical embodiments, the copper is in the form of copper gluconate, copper sulfate or copper glycinate. In currently preferred embodiments, the copper is in the form of copper gluconate.

In certain embodiments, the therapeutically effective amount of copper is 0.01-0.1 mg, 0.1-1 mg, 1.0-10.0 mg, 10.0-20 mg, 20-30 mg, 30-40 mg, 40-50 mg, 50-60 mg, 60-70 mg, 70-80 mg, 80-90 mg or 90-100 mg. In certain embodiments, the therapeutically effective amount of copper is 0.1 mg-30 mg. In certain embodiments, a therapeutically effective amount of copper gluconate is administered. In certain embodiments, the therapeutically effective amount of copper gluconate is 0.01-0.1 mg, 0.1-1 mg, 1.0-10.0 mg, 10.0-20 mg, 20-30 mg, 30-40 mg, 40-50 mg, 50-60 mg, 60-70 mg, 70-80 mg, 80-90 mg and 90-100 mg. In an embodiment, the therapeutically effective amount of copper gluconate is 0.1 mg-30 mg.

In an embodiment, the therapeutically effective amount of copper gluconate is 1.5 mg-3 mg. In an embodiment, the therapeutically effective amount of copper gluconate is 1.5 mg.

In certain embodiments, the DSF is administered orally once daily, twice daily, thrice daily, 4 times daily, 5 times daily, every other day, 2 times per week, weekly or monthly. In certain embodiments, the copper is administered orally once daily, twice daily, thrice daily, 4 times daily, 5 times daily, every other day, 2 times per week, weekly or monthly. In certain embodiments, the copper gluconate is administered orally once daily, twice daily, thrice daily, 4 times daily, 5 times daily, every other day, 2 times per week, weekly, bi-weekly or monthly. In certain embodiments, the DSF and copper are orally administered simultaneously once daily, twice daily, thrice daily, 4 times daily, 5 times daily, every other day, 2 times per week, weekly or monthly. In certain embodiments, the DSF and copper gluconate are orally administered simultaneously once daily, twice daily, thrice daily, 4 times daily, 5 times daily, every other day, 2 times per week, weekly, bi-weekly or monthly.

In certain embodiments, the oral dosage form comprising DSF is administered without food. In some embodiments, the oral dosage form comprising DSF is administered in the fasting state.

In some embodiments, DSF and/or copper are administered with food or shortly after the subject has eaten a meal, or within 1 hour before or after the subject ingests food. In certain embodiments, the oral dosage forms comprising DSF and/or copper are administered without food or when the subject has an empty stomach, or greater than 2 hours after the subject has ingested food.

In accordance with an aspect of the methods described herein for treating cancer in a subject, the methods include administering to the patient a therapeutically effective amount of DSF and an intracellular copper ion stimulant, which can enhance the intracellular level of the above described heavy metal ions in the patient. Intracellular heavy metal ion carriers are known. For example, ceruloplasmin can be administered to the patient to enhance the intracellular copper level. Other copper ion carriers known in the art may also be administered in accordance with this aspect of the invention. The copper ion carriers and the DSF can be administered together or separately.

In accordance with an aspect of the methods described in this application, the oral dosage form can be used in combination with a conventional anti-cancer therapy. For example, the method can be complemented by a conventional radiation therapy or chemotherapy. Thus, in an embodiment, the method comprises administering to a patient DSF and copper and another anti-cancer agent. The other anti-cancer agent may be administered prior to, concurrently or after administration of the DSF and copper.

In order to inhibit cell growth, induce cell differentiation, induce apoptosis, inhibit MDR phenotype, inhibit metastasis, inhibit angiogenesis or otherwise reverse or reduce the malignant phenotype of tumor cells using the methods and compositions of the present application, a "target" cell is contacted with one or more compositions described herein. In certain embodiments, the composition or dosage form composed of DSF and copper and at least one other agent can be administered. In certain embodiments, the other agent is an anti-cancer agent. Examples of anti-cancer agents include, but are not limited to, radiation, platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, plicamycin, dactinomycin), taxanes (e.g., paclitaxel, nab-paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine, gemcitabine, 5-flurouracil), topoisomerase inhibitors (e.g., topotecan and irinotecan), hypomethylating agents (e.g., azacitidine and decitabine), proteasome inhibitors (e.g., bortezomib), epipodophyllotoxins (e.g., etoposide and teniposide), DNA synthesis inhibitors (e.g., hydroxyurea), vinca alkaloids (e.g., vincristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab, ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicalutamide, granisetron, flutamide, androgen receptor antagonists), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, PARP inhibitors, immunotheapeutics (e.g., PD1 antagonists, PDL-1 antagonists), or any combination thereof.

In certain embodiments, the compositions and dosage forms described herein improve the efficacy of chemotherapy and radiotherapy. One approach involves using the compositions or dosage forms described herein in combination with chemo or therapeutic or radiotherapeutic intervention. This treatment option may offer a synergistic therapeutic effect along with the disulfiram and copper complex.

In certain embodiments, DSF and copper are administered with temozolomide for the treatment of glioblastoma. In certain embodiments, DSF and copper are administered with Paclitaxel for the treatment of breast cancer, including triple-negative breast cancer.

In certain embodiments, DSF and copper are administered with a chemotherapeutic and/or targeted anti-cancer agent for the treatment of cancer, including, but not limited to, glioblastoma, prostate cancer, pancreatic cancer, rectal cancer, colon cancer, head and neck cancer, kidney cancer, bladder cancer, lung cancer, medulablastoma and breast cancer.

In certain embodiments, the methods of the application are used for the treatment of pancreatic cancer. In certain embodiments, the methods of the application are used for the treatment of metastatic pancreatic cancer. In certain embodiments, DSF and copper are administered with Nab-paclitaxel and gemcitabine for the treatment of metastatic pancreatic cancer. In certain embodiments, DSF and copper are administered with Nab-paclitaxel and gemcitabine for the treatment of metastatic pancreatic cancer in patients that have previously received combination chemotherapy comprising 5-Fluorouracil, leucovorin, irinotecan and oxaliplatin.

Alternatively, any of the treatments with DSF and/or copper compositions or dosage forms may precede or follow the other agent treatment by intervals ranging from minutes to weeks. In embodiments where the other agent and any of the DSF and/or copper compositions or dosage forms described herein are applied separately to the cell, a significant period of time should not expire between the time of each delivery, such that the agent and DSF copper complex would still be able to exert an advantageously combined (e.g., synergistic) effect on the cell. In an embodiment, the cell can be contacted with both the other agent, DSF and copper within about 12-24 h, or from about 6-12 h of each other, with a delay time of up to about 12 h. In some situations, it may be desirable to extend the duration of treatment with just the therapeutic agent, for example, where several days (2, 3, 4, 5, 6 or 7) to several weeks (1, 2, 3, 4, 5, 6, 7 or 8) lapse between the respective administrations.

In certain aspects, methods of treating subjects with conditions that would benefit from the treatment of DSF and zinc are presented. The methods comprise administering to a subject with cancer, a hyperproliferative disorder or other condition or administering to a subject suspected of having a high probability of developing cancer, a hyperproliferative disorder or other condition an effective amount of DSF and an effective amount of zinc on a temporally staggered dosage schedule.

In certain embodiments, the methods comprise administering an effective amount of an oral dosage form comprising DSF preceded by or followed by administration an effective amount of an oral dosage form comprising zinc. In some embodiments, the oral dosage form comprising zinc is administered prior to administration of the oral dosage form comprising DSF. In embodiments that are currently preferred, the DSF oral dosage form is administered prior to administration of the zinc oral dosage form. In certain embodiments, the zinc oral dosage form is administered not less than one hour before the administration of the DSF oral dosage form. In certain embodiments, the zinc oral dosage form is administered not less than one hour after the administration of the DSF oral dosage form.

In a variety of embodiments, DSF and zinc are administered together in a single oral dosage form, wherein the oral dosage form is configured to temporally stagger release of disulfiram (DSF) and zinc after ingestion. In various embodiments, release of DSF is preceded by or followed by release of zinc. In embodiments that are currently preferred, DSF is released prior to release of zinc. Such staggered-release oral dosage forms are described herein further below.

In certain aspects, methods of treating disorders or conditions that would benefit from the treatment of DSF and zinc are presented. In certain embodiments, the condition is an infection. In certain embodiments, the methods described herein comprise administering DSF and zinc for the treatment of tuberculosis. In certain embodiments, the methods described herein comprise administering DSF and zinc for the treatment of leishmaniasis.

In the methods described herein, a therapeutically effective amount of zinc is administered. In typical embodiments, the zinc is in the form of zinc gluconate, zinc sulfate or zinc glycinate. In currently preferred embodiments, the zinc is in the form of zinc gluconate.

In certain embodiments, the therapeutically effective amount of zinc is 10-300 mg, 10.0-50 mg, 50-100 mg, 100-150 mg, 150-200 mg, or 200-300 mg. In certain embodiments, a therapeutically effective amount of zinc gluconate is administered. In certain embodiments, the therapeutically effective amount of zinc gluconate is 10-300 mg, 10.0-50 mg, 50-100 mg, 100-150 mg, 150-200 mg, or 200-300 mg. In an embodiment, the therapeutically effective amount of zinc gluconate is 50 mg.

In certain embodiments, the DSF is administered orally once daily, twice daily, thrice daily, 4 times daily, 5 times daily, every other day, 2 times per week, weekly or monthly. In certain embodiments, the zinc is administered orally once daily, twice daily, thrice daily, 4 times daily, 5 times daily, every other day, 2 times per week, weekly or monthly. In certain embodiments, the copper gluconate is administered orally once daily, twice daily, thrice daily, 4 times daily, 5 times daily, every other day, 2 times per week, weekly, bi-weekly or monthly. In certain embodiments, the DSF and zinc are orally administered simultaneously once daily, twice daily, thrice daily, 4 times daily, 5 times daily, every other day, 2 times per week, weekly or monthly. In certain embodiments, DSF and zinc gluconate are orally administered simultaneously once daily, twice daily, thrice daily, 4 times daily, 5 times daily, every other day, 2 times per week, weekly, bi-weekly or monthly.

In some embodiments, DSF and/or zinc are administered with food or shortly after the subject has eaten a meal, or within 1 hour before or after the subject ingests food. In certain embodiments, the oral dosage forms comprising DSF and/or zinc are administered without food or when the subject has an empty stomach, or greater than 2 hours after the subject has ingested food.

In accordance with an aspect of the methods described herein for treating cancer in a subject, the methods include administering to the patient a therapeutically effective amount of DSF and an intracellular zinc ion stimulant, which can enhance the intracellular level of the above described heavy metal ions in the patient. Zinc ion carriers known in the art may also be administered in accordance with this aspect of the invention. The zinc ion carriers and the DSF can be administered together or separately.

In accordance with an aspect of the methods described in this application, the oral dosage form comprising DSF and zinc can be used in combination with a conventional anti-cancer therapy. For example, the method can be complemented by a conventional radiation therapy or chemotherapy. Thus, in an embodiment, the method comprises administering to a patient DSF and zinc and another anti-cancer agent, including, but not limited to the anti-cancer agents described herein. The other anti-cancer agent may be administered prior to, concurrently with or after administration of the DSF and zinc.

In certain embodiments, the composition or dosage form composed of DSF and zinc and at least one other agent can be administered. In certain embodiments, the other agent is an anti-cancer agent. In certain embodiments, the compositions and dosage forms described herein improve the efficacy of chemotherapy and radiotherapy.

In certain embodiments, DSF and zinc are administered with temozolomide for the treatment of glioblastoma. In certain embodiments, DSF and zinc are administered with Paclitaxel for the treatment of breast cancer, including triple-negative breast cancer.

In certain embodiments, DSF and zinc are administered with a chemotherapeutic and/or targeted anti-cancer agent for the treatment of cancer, including, but not limited to, glioblastoma, prostate cancer, pancreatic cancer, rectal cancer, colon cancer, kidney cancer, bladder cancer, head and neck cancer and breast cancer.

In certain embodiments, the methods of the application are used for the treatment of pancreatic cancer. In certain embodiments, the methods of the application are used for the treatment of metastatic pancreatic cancer. In certain embodiments, DSF and zinc are administered with Nab-paclitaxel and gemcitabine for the treatment of metastatic pancreatic cancer. In certain embodiments, DSF and zinc are administered with Nab-paclitaxel and gemcitabine for the treatment of metastatic pancreatic cancer in patients that have previously received combination chemotherapy comprising 5-Fluorouracil, leucovorin, irinotecan and oxaliplatin.

Alternatively, any of the treatments with DSF and/or zinc compositions or dosage forms may precede or follow the other agent treatment by intervals ranging from minutes to weeks. In embodiments where the other agent and any of the DSF and/or zinc compositions or dosage forms described herein are applied separately to the cell, a significant period of time should not expire between the time of each delivery, such that the agent and DSF zinc complex would still be able to exert an advantageously combined (e.g., synergistic) effect on the cell. In an embodiment, the cell can be contacted with both the other agent, DSF and zinc within about 12-24 h, or from about 6-12 h of each other, with a delay time of up to about 12 h. In some situations, it may be desirable to extend the duration of treatment with just the therapeutic agent, for example, where several days (2, 3, 4, 5, 6 or 7) to several weeks (1, 2, 3, 4, 5, 6, 7 or 8) lapse between the respective administrations.

In certain embodiments, the compositions described herein can be combined with therapies that induce DNA damage when applied to a cell. Such therapies include radiation such as, for example, y-irradiation, X-ray, UV-irradiation, microwave, electronic emissions, and the like.

In certain embodiments, the method described in the application result in reduced tumor burden, increased overall survival, increased progression-free survival and/or decreased disease symptoms in the patient.

5.4. Staggered-Release Oral Unit Dosage Forms

In an embodiment, the present application provides an oral dosage form configured to release an effective amount of DSF followed by release of an effective amount of copper in a subject after ingestion.

Disulfiram has been used clinically in the treatment of alcohol abuse, in which disulfiram inhibits hepatic aldehyde dehydrogenase. Disulfiram has the following formula.

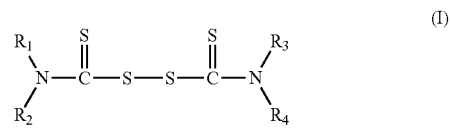

(I)

where R1, R2, R3, and R4 are all ethyl.

The thiolate anion derivative of disulfiram is diethyldithiocarbamate anion, the sodium salt of which has the following formula:

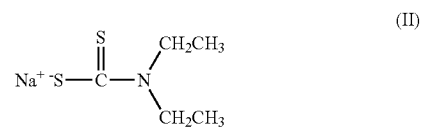

(II)

The copper complex of diethyldithiocarbamate is shown below as Copper 1,1-dithiolato complex, in the following formula:

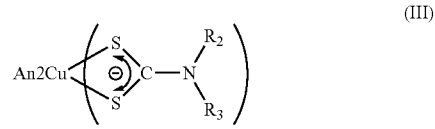

(III)

wherein R2, R3 are ethyl, and An is an anion of low molecular weight. As used herein, the DSF copper complex refers to the Copper 1,1-dithiolato complex.

Copper ions can be administered separately as an aqueous solution in a pharmaceutically suitable salt form. In an embodiment, copper ions are administered separately to form a chelate after ingestion in which the ions are complexed with thiuram disulfide compounds. Thus, the amount of copper to be used advantageously is proportional to the amount of thiuram disulfide compound to be administered based on the molar ratio between a copper and thiuram disulfide compound in the chelate.

Zinc ions can be administered separately as an aqueous solution in a pharmaceutically suitable salt form. In an embodiment, zinc ions are administered separately to form a chelate after ingestion in which the ions are complexed with thiuram disulfide compounds. Thus, the amount of zinc to be used advantageously is proportional to the amount of thiuram disulfide compound to be administered based on the molar ratio between a zinc and thiuram disulfide compound in the chelate.

In certain embodiment, an oral dosage forms are presented that comprise dithiocarbamate disulfides, thiocarbamate anions in combination with copper, thiocarbamate complexes with copper ions, and dithiocarbamate metal chelates as described in U.S. Pat. No. 6,548,540 which is herein incorporated by reference in its entirely.

In certain embodiments, oral dosage forms are presented that comprise thiocarbamate anions in combination with zinc and thiocarbamate complexes with zinc ions, as described in U.S. Pat. No. 6,548,540, which is herein incorporated by reference in its entirely.

The oral dosage forms used in the methods described herein may comprise disulfiram without copper, copper without disulfiram, or disulfiram and copper. In certain embodiments, the copper is in the form of copper gluconate. These oral dosage forms can comprise, in addition to disulfiram and/or copper, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on, for example, the dosage of active DSF copper complex needed for effective treatment, timing and location of release of the DSF and/or copper, solubility and stability of DSF and/or copper and/or DSF copper complex, dosages of DSF copper and copper required for formation of the DSF copper complex, absorption characteristics of the DSF, copper and/or DSF copper complex.

The oral dosage forms described herein can be tablet, capsule, powder or liquid forms. A tablet can include a solid carrier such as gelatin or an adjuvant. Liquid dosage forms generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The DSF and/or copper can also be delivered orally in enclosed gelatin capsules (e.g., hard gelatin or soft gelatin) or compressed tablets. Capsules and tablets can be prepared using any conventional techniques. For example, the active compounds can be incorporated into a formulation which includes pharmaceutically acceptable carriers, such as excipients (e.g., starch, lactose), binders (e.g., gelatin, cellulose, gum), disintegrating agents (e.g., croscarmellose sodium, crospovidone, alginate, Primogel, and corn starch), lubricants (e.g., magnesium stearate, silicon dioxide), and sweetening or flavoring agents (e.g., glucose, sucrose, saccharin, methyl salicylate, and peppermint). Possible excipients include those that have been previously used in FDA-approved products such as, microcrystalline cellulose (MCC), and lactose anhydrous, as fillers; croscarmellose sodium, and crospovidone as disintegrants; colloidal silicon dioxide as glidant; magnesium stearate and talc as lubricants and anti-adherents. Suitable excipients include, colloidal silicon dioxide, anhydrous lactose, sodium starch glycolate, and stearic acid.

Various coatings can also be prepared for the capsules and tablets to modify the flavors, tastes, colors, and shapes of the capsules and tablets. In addition, liquid carriers such as fatty oil can also be included in capsules. In certain embodiments, for administration of DSF, it is desirable to administer the compounds as enteric-coated capsules that are impervious to stomach acid but dissolve in the alkaline environment of the intestines or colon, in order to prevent release of carbon disulfide from dithiocarbamates in the acid environment of the stomach, and to preserve the integrity of the DSF. In certain embodiments, for administration of copper, it is desirable to administer the compounds as enteric-coated capsules that are impervious to stomach acid but dissolve in the alkaline environment of the intestines or colon.

Other forms of oral formulations such as chewing gum, suspension, syrup, wafer, elixir, and the like can also be prepared containing the active compounds used in this invention. Various modifying agents for flavors, tastes, colors, and shapes of the special forms can also be included. In addition, for convenient administration by enteral feeding tube in patients unable to swallow, the active compounds can be dissolved in an acceptable lipophilic vegetable oil vehicle, such as olive oil, corn oil, and safflower oil.

The DSF and/or copper can also be conjugated, i.e., covalently linked, to a water soluble non-immunogenic high molecular weight polymer to form a polymer conjugate.

Advantageously, such polymers, e.g., polyethylene glycol, can impart solubility, stability, and reduced immunogenicity to the active compounds. As a result, the DSF, copper or DSF copper complex in the conjugate when administered to a patient, can have a longer half-life in the body, and exhibit better efficacy. PEGylated proteins are currently being used in protein replacement therapies and for other therapeutic uses. For example, PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). For a general review of PEG-protein conjugates with clinical efficacy. See, e.g., Burnham, *Am. J. Hosp. Pharm.*, 15:210-218 (1994). Preferably, the covalent linkage between the polymer and the active compound is hydrolytically degradable and is susceptible to hydrolysis under physiological conditions. Such conjugates are known as "prodrugs" and the polymer in the conjugate can be readily cleaved off inside the body, releasing the free active compounds. Alternatively, other forms controlled release or protection including microcapsules and nanocapsules generally known in the art, and hydrogels described above can all be utilized in oral administration of the DSF and/or copper. Another preferable delivery form comprises liposomes as carriers. Liposomes are micelles formed from various lipids such as cholesterol, phospholipids, fatty acids, and derivatives thereof. The DSF and/or copper can be enclosed within such micelles. Methods for preparing liposomal suspensions containing therapeutic agents therein are generally known in the art and are disclosed in, e.g., U.S. Pat. No. 4,522,811. Several anti-cancer drugs delivered in the form of liposomes are known in the art and are commercially available from Liposome Inc. of Princeton, N.J., U.S.A. It has been shown that liposomal formulations can reduce the toxicity of the active compounds, and increase their stability.

In certain aspects, the oral dosage forms comprise DSF and copper. The copper can be in the form of, but is not limited to, copper gluconate. In certain embodiments, the pharmaceutical composition described herein, comprise 0.01-0.1 mg, 0.1-1 mg, 1.0-10.0 mg, 10.0-20 mg, 20-30 mg, 30-40 mg, 40-50 mg 50-60 mg, 60-70 mg, 70-80 mg, 80-90 mg, 90-100 mg, 100-150 mg, 150-200 mg, 200-300 mg, 300-400 mg, 400-500 mg and 500-1,000 mg of DSF. In certain embodiments, the pharmaceutical compositions described herein, comprise 0.01-0.1 mg, 0.1-1 mg, 1.0-10.0 mg, 10.0-20 mg, 20-30 mg, 30-40 mg, 40-50 mg 50-60 mg, 60-70 mg, 70-80 mg, 80-90 mg and 90-100 mg of copper. In certain embodiments, the pharmaceutical compositions described herein, comprise 0.01-0.1 mg, 0.1-1 mg, 1.0-10.0 mg, 10.0-20 mg, 20-30 mg, 30-40 mg, 40-50 mg 50-60 mg, 60-70 mg, 70-80 mg, 80-90 mg and 90-100 mg of copper gluconate.

In certain embodiments, the DSF is formulated to be released immediately upon ingestion, and the copper is formulated to be released between 1 min and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of the DSF. In certain embodiments, the copper is formulated to be released immediately upon ingestion, and the DSF is formulated to be released between 1 min and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of the copper. In certain embodiments, the onset of release of the DSF is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h before the release of the copper. In certain embodiments, the onset of release of the copper is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of DSF. In certain embodiments, the onset of release of the copper is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 2 h and 8 h before the release of the DSF. In certain embodiments, the onset of release of the DSF is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of the copper.

In certain embodiments, the DSF is formulated to be released in the stomach and the copper is formulated to be released in the intestines. In certain embodiments, the copper is formulated to be released in the stomach and the DSF is formulated to be released in the intestines. In certain embodiments, the DSF is formulated to begin release in the stomach and the copper is formulated to begin release in the intestines. In certain embodiments, the copper is formulated to begin release in the stomach and the DSF is formulated to begin release in the intestines. In certain embodiments, the DSF is formulated to complete release in the stomach and the copper is formulated to complete release in the intestines. In certain embodiments, the copper is formulated to complete release in the stomach and the DSF is formulated to complete release in the intestines. In certain embodiments, the DSF is formulated to be released in the stomach and the copper is formulated to be released in the colon. In certain embodiments, the copper is formulated to be released in the stomach and the DSF is formulated to be released in the colon.

In certain embodiments, the oral dosage form comprises DSF in solid form and copper in solid form. In certain embodiments, the oral dosage form comprises DSF in liquid form and copper in solid form. In certain embodiments, the oral dosage form comprises both DSF and copper in liquid form. In certain embodiments, the oral dosage form comprises copper in liquid form and DSF in solid form.

In certain embodiments, the oral dosage form comprises DSF and copper located in different layers. In certain embodiments, the DSF is in the outer layer and the copper is located in a layer underneath the layer comprising DSF. In certain embodiments, the copper is in the outer layer and the DSF is located in a layer underneath the layer comprising copper. In certain embodiments, there are one or more intermediate layers. In certain embodiments, the intermediate layers do not comprise DSF or copper. In certain embodiments, the dosage form is a core compressed matrix tablet, wherein the DSF or copper is located in the interior core center of the tablet and the outer layer is an immediate release layer comprising DSF or copper. In certain embodiments, the interior core center comprises granules that contain DSF or copper. In certain embodiments, the oral dosage form is a bi-layer tablet wherein, an immediate release layer comprising DSF or copper is adjacent to a sustained release layer comprising DSF or copper. In certain embodiments, one or more of the layers comprise an enteric coating. In certain embodiments, one or more of the layers comprise a disintegrant or a superdisintegrant. In certain embodiments, one or more of the layers comprise a matrix for retaining the DSF and/or copper in the layer upon ingestion. In certain embodiments, one or more of the layers comprise a polymeric material for increasing retention of the DSF and/or copper in oral dosage form upon ingestion.

In certain embodiments, the oral dosage form comprises one or more types of granules. In certain embodiments, the oral dosage form is a capsule comprising one or more types of granules, wherein one granule is an immediate release granule comprising DSF or copper and the other type of granule is a delayed release granule comprising DSF or copper. In certain embodiments, the granules are 0.01-0.1 mm, 0.1-0.25 mm, 0.25-0.5 mm, 0.5-0.75 mm, 0.75-1.0 mm, 1.0 mm-2.0 mm, 2.0-3.0 mm, 3.0 mm-4.0 mm, 4.0 mm-5.0 mm, or 1.0-5.0 mm in diameter, height or width. In certain embodiments, the oral dosage form comprises granules comprising DSF. In certain embodiments, the oral dosage form comprises granules comprising copper. In certain embodiments, the oral dosage form comprises at least two types of granules, wherein one type of granule comprises DSF and another type of granule comprises copper. In certain embodiment, the granules comprise at least one disintegrant or a superdisintegrant. In certain embodiments, the granules are coated with an enteric coating. In certain embodiments, one or more of the granules comprise a matrix for retaining the DSF and/or copper in the granule. In certain embodiments, one or more of the granules comprise a polymeric material for increasing retention of the DSF and/or copper in the granule upon ingestion. In certain aspects, the granules are minitablets.

In certain embodiments, the release of DSF is controlled by an osmotically-controlled and/or diffusion-controlled system. In certain embodiments, the oral dosage form comprises a substance that absorbs water. In certain embodiments, the oral dosage form comprises a pore, wherein the release of DSF is controlled by diffusion of the DSF through the pore. In certain embodiments, the oral dosage form comprises a pore, wherein the release of copper is controlled by diffusion of copper through the pore.

In certain embodiments, the oral dosage form comprises a matrix for controlled release of DSF and/or copper. In certain embodiments the matrix is hydrophobic. In certain embodiments, the matrix is hydrophilic. In certain embodiments, the matrix is a polymer for controlled release of DSF and/or copper. In come embodiments, the oral dosage form comprises a polymer device comprising a polymeric carrier for controlled release of DSF and/or copper. A common polymeric carrier is N-(2-hydroxypropyl)methacrylamide (HPMA) copolymer; however, other suitable systems include, but are not limited to, poly(glutamic acid), PEI, dextran, dextrin, chitosans, poly(l-lysine) and poly(aspartamides) as polymeric carriers. Other suitable polymeric materials which can be used as polymeric carriers include, but are not limited to, hydrogels, cellulose derivatives, poly(ethylene glycol) PEG, and poly(N-vinyl pyrrolidone). For drug delivery, polymer devices can be diffusion-controlled (monolithic devices), solvent-activated (swelling- or osmotically-controlled devices, chemically controlled (biodegradable) or externally-triggered systems (e.g., pH, temperature).

In certain embodiments, the oral dosage form controls the release of DSF and/or copper by a diffusion-controlled system. In certain diffusion-controlled systems, a drug is dissolved (or dispersed if the concentration exceeds the polymer's solubility limit) in a nonswellable or fully swollen matrix that does not degrade during its therapeutic life. In certain embodiments, the diffusion-controlled system can comprise porous, microporous, and nonporous hydrogels.

In certain embodiments, the oral dosage form controls the release of DSF and/or copper by an osmotic-controlled system. In certain osmotic-controlled systems, drugs are loaded into dehydrated hydrophilic polymers or hydrogels by simply packing the two substances together. In the absence of a plasticizing aqueous solvent, these systems are usually well below their glass transition temperature and have very low diffusivities. Once exposed to an aqueous environment, the hydrogels absorb water and swell. Drug delivery devices that operate as osmotic-controlled systems undergo a transition from the glassy to rubbery state during solvent swelling, which relaxes polymer chains and dissolves dispersed drug deposits.

In certain embodiments, the oral dosage form comprises a semi-permeable membrane.

In certain embodiments, the oral dosage form comprises a disintegrant. In certain embodiments, the disintegrant is a superdisintegrant. Suitable disintegrants can be, but are not limited to, superpolysates, crosslinked polyvinylpyrrolidone, crospovidone, pregelatinized starches, sodium starch glycolate, carboxymethylcellulose, croscarmellose, sodium bicarbonate and tartaric acid.

In certain embodiments, the oral dosage form controls the release of DSF and/or copper by a chemically-controlled system. In certain embodiments, the chemically-controlled system comprises biodegradable and/or bioerodible polymers. Covalent bond cleavage by chemical reactions occurs in degradation. Erosion occurs by the dissolution of chain fragments in noncrosslinked systems without chemical alterations to the molecular structure. To be chemically degradable, polymers generally require hydrolytically or proteolytically labile bonds in their backbone or crosslinker. The majority of biodegradable synthetic polymers rely on hydrolytic cleavage of ester bonds or ester derivatives such as poly(lactic/glycolic acid) and poly(ε-caprolactone). In addition to ester derivatives, hydrolysis may also act on poly(anhydrides), poly(orthoesters), poly(phosphoesters), poly(phosphazenes), and poly(cyanoacrylate) derivatives.

In certain embodiments the oral dosage form comprises a core, wherein the core comprises DSF and/or copper. In certain embodiments, the external surface of the core is coated with a pH-sensitive or pH-insensitive composition. In certain embodiments, the oral dosage form comprises an enteric coating or a gastro-resistant composition. In certain embodiments, the enteric coating or gastro-resistant composition prevent release of DSF or copper at a pH less than 2.5, less than 3.0, less than 4.0, less than 5.0, 6.0, less than 6.2 or less than 7.0. In certain embodiments, the enteric coating or gastro-resistant composition is an acid-soluble composition and delays release of DSF or copper upon exposure to a pH less than 2.5, less than 3.0, less than 4.0, less than 4.5, less than 5.0, less than 5.5, less than 6.0, less than 6.2, less than 6.5, less than 7.0, less than 7.1, less than 7.2, or less than 7.5.

In certain embodiments, the oral dosage form comprises a core that is coated with a composition that allows release of DSF or copper upon exposure to an acidic solution with a pH less than 2.5, less than 3.0, less than 3.5, less than 4.0, less than 4.5, less than 5.0, less than 5.5, less than 6.0, less than 6.2, less than 6.5, less than 7.0, less than 7.1, less than 7.2, or less than 7.5.

In certain embodiments, the oral dosage form comprises DSF and/or copper coated with water-swellable polymers. Water-swellable polymers include acrylate polymers, which are generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "Eudragit" from Rohm Pharma (Germany). The Eudragit® series E, L, S, RL, RS, FS and NE copolymers are available as solubilized in organic solvent, in an aqueous dispersion, or as a dry powder. In certain embodiments, the acrylate polymers are copolymers of methacrylic acid and methyl methacrylate, such as the Eudragit® L and Eudragit® S series polymers. In certain embodiments the copolymers are Eudragit® L-30D-55 and Eudragit® L-100-55 (the latter copolymer is a spray-dried form of Eudragit® L-30D-55 that can be reconstituted with water). In certain embodiments the oral dosage form comprises compositions coated with AcrylEZE®, a coating comprising Eudragit® L-100-55. The molecular weight of the Eudragit® L-30D-55 and Eudragit® L-100-55 copolymer is approximately 135,000 Da, with a ratio of free carboxyl groups to ester groups of approximately 1:1. The copolymer is generally insoluble in aqueous fluids having a pH below 5.5. Another suitable methacrylic acid-methyl methacrylate copolymer is Eudragit® FS-30 D and Eudragit® S-100. Eudragit® FS-30 D and Eudragit® S-100 are insoluble at pH below 5.5, but unlike Eudragit® L-30D-55, are poorly soluble in aqueous fluids having a pH in the range of 5.5 to 7.0. Eudragit® FS-30 D and Eudragit® S-100 copolymers are soluble at pH 7.0 and above. Eudragit® L-100 may also be used, which has a pH-dependent solubility profile between that of Eudragit® L-30D-55 and Eudragit® L-100, insofar as it is insoluble at a pH below 6.0. It will be appreciated by those skilled in the art that Acryl-EZE®, Eudragit® L-30D-55, L-100-55, L-100, FS 30 D and S-100 can be replaced with other acceptable polymers having similar pH-dependent solubility characteristics In certain embodiments, the oral dosage form comprises DSF and/or copper coated with a time-controlled release coating that exhibits pH-independent solubility. Suitable coating include copolymers of Ethyl acrylate, methyl methacrylate and methacrylic acid ester with quaternary ammonium groups. Suitable coatings include the Eudragit® series RL, RS, NE and NM copolymers that exhibit pH-independent solubility. In certain embodiments, the coating comprises Eudragit® RL 30D. In certain embodiments, the coating comprises Eudragit® RS 30D. In certain embodiments, the coating enables drug release more than 0.5 h, 1.0 h, 1.5 h, 2.0 h, 2.5 h, 3.0 h, 3.5 h, 4.0 h, 4.5 h or 5.0 h after oral administration.

In certain embodiments, the oral dosage form comprises DSF and/or copper coated with an aqueous film coating. In certain embodiments the oral dosage form comprises a core, wherein the core comprises DSF and/or copper. In certain embodiments, the external surface of the core is coated with a pH-insensitive polymer that does not confer pH dependent swelling. In certain embodiments, the external surface of the core is coated with a composition that comprises a polymer, a plasticizer and a pigment. In certain embodiments the polymer is a low viscosity hydroxypropyl methylcellulose (HPMC). In certain embodiments, the external surface of the core is coated with Opadry®, Opadry® II, or Opadry® II 85. In certain embodiments the external surface of the core is coated with composition comprising sodium carboxymethylcellulose (NaCMC), polyvinyl alcohol, or combinations thereof. In certain embodiments, the external surface of the core is coated with composition comprising Opadry® AMB In certain embodiments, the external coating is present at a thickness, measured as weight gain upon application, of 1%, 2%, 2.5%, 3%, 3.5% 4%, 4.5%, 5%, 5.5%, 6%, 6.5%, 7%, 7.5%, 8%, 8.5%, 9%, 9.5%, 10% 11%, 12%, 13%, 14%, 15%, 16%, 17%, 18%, 19%, 20%, 21%, 22%, 23%, 24%, or 25%.

In certain embodiments, the oral dosage form comprises compositions coated with a plurality of different polymers either in combination or in separate layers. In certain embodiments, the oral dosage form comprises compositions coated with at least one polymer that is pH-independent and in a separate layer at least one polymer that is pH-independent. In certain embodiments, the oral dosage form is coated with 2, 3, 4, or 5 or more polymers. In certain embodiments, the oral dosage form is coated with 2, 3, 4, or 5 or more separate layers. It will be appreciated by those skilled in the art that suitable polymers may be applied to the oral dosage form in any suitable combination at any suitable ratio.

In certain embodiments, the oral dosage form controls the release of DSF and/or copper by externally-triggered systems. In certain embodiments, the externally-triggered system comprises environmentally-responsive polymers or smart polymers. The majority of environmentally-responsive polymers for drug delivery can be broadly categorized as hydrogels, micelles, polyplexes or polymer-drug conjugates. Environmentally-responsive polymers are a class of materials comprised of a large variety of linear and branched (co)polymers or crosslinked polymer networks. A hallmark of responsive polymers is their ability to undergo a dramatic physical or chemical change in response to an external stimulus of a physical or chemical nature. Physical stimuli (i.e., temperature, ultrasound, light, electromagnetic radiation and magnetic and electrical fields) directly modulate the energy level of the polymer/solvent system and induce a polymer response at some critical energy level. Chemical stimuli (i.e., pH, redox potential, ionic strength, and chemical and biochemical agents) induce a response by altering molecular interactions between polymer and solvent (adjusting hydrophobic/hydrophilic balance) or between polymer chains (influencing crosslink or backbone integrity, proclivity for hydrophobic association, or electrostatic repulsion). These stimuli may induce changes such as, but not limited to, transitions in solubility, hydrophilic-hydrophobic balance, and conformation. These changes are manifested in many ways, such as, but not limited to, the coil-globule transition of polymer chains, swelling/deswelling of covalently crosslinked hydrogels, sol-gel transition of physically crosslinked hydrogels and self-assembly of amphiphilic polymers.

In certain embodiments, the DSF and/or copper are administered in combination with other therapeutic agents that treats or prevents another disease or symptom in the subject treated. However, it is to be understood that such other therapeutic agents should not interfere with or adversely affect the effects of the active compounds of this invention on the cancer being treated. Such other therapeutic agents include, but are not limited to, anti-cancer agents, antiviral agents, antibiotics, antifungal agents, anti-inflammation agents, antithrombotic agents, cardiovascular drugs, cholesterol lowering agents, hypertension drugs, and the like.

Examples of anti-cancer agents include, but are not limited to, radiation, platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, plicamycin, dactinomycin), taxanes (e.g., paclitaxel, nab-paclitaxel and docetaxel), antimetabolites (e.g., 5-fluorouracil, cytarabine, pemetrexed, thioguanine, floxuridine, capecitabine, and methotrexate), nucleoside analogues (e.g., fludarabine, clofarabine, cladribine, pentostatin, nelarabine, gemcitabine), topoisomerase inhibitors (e.g., topotecan and irinotecan), hypomethylating agents (e.g., azacitidine and decitabine), proteasome inhibitors (e.g., bortezomib), epipodophyllotoxins (e.g., etoposide and teniposide), DNA synthesis inhibitors (e.g., hydroxyurea), *vinca* alkaloids (e.g., vincristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab, ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicalutamide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, PARP inhibitors, or any combination thereof.

5.4.1. DSF and Copper Staggered Release Oral Dosage Forms

In certain preferred embodiments, the oral dosage form described herein comprises a capsule containing at least one disulfiram minitablet and at least one copper minitablet, wherein the minitablets are coated to cause staggered release of the disulfiram and copper upon administration. In certain preferred embodiments, the oral dosage form described herein comprises a capsule containing at least one disulfiram minitablet and at least one copper minitablet, wherein each disulfiram minitablet and copper minitablet comprises a core, wherein each core contains disulfiram or copper and one or more excipients. In certain embodiments, the capsule is a hard gelatin capsule. In certain embodiments, the capsule is a soft gelatin capsule. In certain embodiments the copper core comprises copper gluconate and/or copper glycinate.

In certain embodiments, the capsule contains 1, 2, 3, 4, 5, 6, 7, 8, 9, 10, or more copper minitablets. In certain embodiments, the capsule contains 1, 2, 3, 4, 5, 6, 7, 8, 9, 10, or more disulfiram minitablets.

In certain embodiments, the disulfiram minitablets within a capsule collectively contain 20 mg DSF, 30 mg DSF, 40 mg DSF, 50 mg DSF, 60 mg DSF, 70 mg DSF, 80 mg DSF, 90 mg DSF, 100 mg DSF, or 120 mg DSF.

In certain embodiments, the one or more excipients are colloidal silicon dioxide, anhydrous lactose, magnesium stearate, microcrystalline cellulose, sodium starch glycolate, stearic acid, anhydrous lactose, sodium croscarmellose, crospovidone, colloidal silicon dioxide, magnesium stearate, talc, or combinations thereof.

In certain embodiments, the copper minitablets within a capsule collectively contain 0.1 mg copper, 0.2 mg copper, 0.25 mg copper, 0.3 mg copper, 0.4 mg copper, 0.5 mg copper, 0.75 mg copper, 1 mg copper, 1.5 mg copper, 2 mg copper, 2.5 mg, 3 mg, 5 mg, 10 mg, 15 mg, 20 mg, 25 mg, or 30 mg copper. In certain embodiments, the copper minitablets within a capsule collectively contain 0.1 mg-30 mg copper.

In certain embodiments, each copper minitablet contains 0.1 mg copper, 0.2 mg copper, 0.25 mg copper, 0.3 mg copper, 0.4 mg copper, 0.5 mg copper, 0.75 mg copper, 1 mg copper, 1.5 mg copper, 2 mg copper, 2.5 mg, 3 mg or 5 mg copper.

In certain embodiments, the copper and/or disulfiram minitablet cores are coated external to the core with a coating. In certain embodiments, the disulfiram minitablet cores are coated with a first coating external to the core. In certain embodiments, the disulfiram first external coating is an aqueous film coating. In certain embodiments, the aqueous film coating is a pH-insensitive coating. In certain embodiments, the coating is a pH-insensitive coating that does not delay release of the DSF. In certain embodiments, the pH-insensitive coating comprises low viscosity hydroxypropyl methylcellulose (HPMC). In certain embodiments, the pH-insensitive coating comprises plasticizers. In certain embodiments, the pH-insensitive coating comprises optional pigments. In certain embodiments, the pH-insensitive coating comprises Opadry®, Opadry® II, Opadry® II 85, Opadry® AMB, sodium carboxymethylcellulose (NaCMC), polyvinol alcohol (PVA), or combinations thereof. In certain embodiments, the disulfiram first external coating is present at a thickness, measured as minitablet weight gain upon application, of approximately 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, or 25%.

In certain embodiments, the copper minitablet cores are optionally coated with a first coating external to the core. In certain embodiments, the copper optional first external coating is an aqueous film coating. In certain embodiments, the optional aqueous film coating is a pH-insensitive coating. In certain embodiments, the coating is a pH-insensitive coating that does not delay release of the copper and/or causes immediate onset of release of the copper upon ingestion. In certain embodiments, the pH-insensitive coating comprises low viscosity hydroxypropyl methylcellulose (HPMC). In certain embodiments, the pH-insensitive coating comprises plasticizers. In certain embodiments, the pH-insensitive coating comprises optional pigments. In certain embodiments, the pH-insensitive coating comprises Opadry®, Opadry® II, Opadry® II 85, Opadry® AMB, sodium carboxymethylcellulose (NaCMC), polyvinol alcohol (PVA), or combinations thereof. In certain embodiments, the copper first external coating is present at a thickness, measured as minitablet weight gain upon application, of approximately 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, or 25%.

In certain embodiments, the copper minitablet cores are coated with a second coating external to the first external coating. In certain embodiments, the copper second external coating is a pH-sensitive delayed release coating. In certain embodiments, the copper second external coating is a pH-sensitive delayed release coat that dissolves upon exposure to an acidic solution with a pH less than 2.5, less than 3.0, less than 3.5, less than 4.0, less than 4.5, less than 5.0, less than 5.5, less than 6.0, less than 6.2, less than 6.5, less than 7.0, less than 7.1, less than 7.2, or less than 7.5.

In certain embodiments, the pH-sensitive delayed release coating dissolves at a pH greater than 5.0, greater than 5.5, greater than 6.0, greater than 6.5, greater than 7.0, greater than 7.1 or greater than 7.2. In certain embodiments, the copper second external coating comprises an aqueous acrylate/methacrylate copolymer. In certain embodiments, the copper second external coating comprises Acryl-EZE®, Eudragit® L-30D-55, Eudragit® L-100-55, Eudragit® L-100, Eudragit® FS 30 D, Eudragit® S-100, or combination thereof. In certain embodiments, the copper first external coating is present at a thickness, measured as minitablet weight gain upon application, of approximately 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%11%, 12%, 13%, 14%, 15%, 16%, 17%, 18%, 19%, 20%, 21%, 22%, 23%, 24%, or 25%.

In certain embodiments, the copper minitablet cores are coated with a third coating external to the second external coating. In certain embodiments, the copper third external coating is a pH-insensitive delayed release coating. In certain embodiments, the copper third external coating comprises an acrylate/methacrylate copolymer. In certain embodiments, the copper third external coating comprises a copolymers of Ethyl acrylate, methyl methacrylate and methacrylic acid ester with quaternary ammonium groups. In certain embodiments, the copper third external coating comprises Eudragit® series RL, RS, NE and NM copolymers or combinations thereof that exhibit pH-independent solubility. In certain embodiments, the coating comprises Eudragit® RL 30D or Eudragit® RS 30D. In certain embodiments, the copper third external coating enables drug release more than 0.5 h, 1.0 h, 1.5 h, 2.0 h, 2.5 h, 3.0 h, 3.5 h, 4.0 h, 4.5 h or 5.0 h after oral administration.

5.4.2. Oral Dosage Forms Comprising DSF and/or Zinc

Oral dosage forms of the invention include a therapeutically effective amount of disulfiram and/or zinc. The pharmaceutical compositions comprising disulfiram and/or zinc of the invention can be formulated in pharmaceutical dosage forms for oral administration. The oral dosage forms used in the methods described herein may comprise disulfiram without zinc, zinc without disulfiram, or disulfiram and zinc. In certain embodiments, the zinc is in the form of zinc gluconate. These oral dosage forms can comprise, in addition to disulfiram and/or zinc, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on, for example, the dosage of active DSF zinc complex needed for effective treatment, timing and location of release of the DSF and/or zinc solubility and stability of DSF and/or zinc and/or DSF zinc complex, dosages of DSF and zinc required for formation of the DSF zinc complex, absorption characteristics of the DSF, zinc and/or DSF zinc complex.

The DSF and/or zinc can also be delivered orally in enclosed gelatin capsules (e.g., hard gelatin or soft gelatin) or compressed tablets. Capsules and tablets can be prepared using any conventional techniques. Various coatings can also be prepared for the capsules and tablets to modify the flavors, tastes, colors, and shapes of the capsules and tablets. In addition, liquid carriers such as fatty oil can also be included in capsules. In certain embodiments, for administration of zinc, it is desirable to administer the compounds as enteric-coated capsules that are impervious to stomach acid but dissolve in the alkaline environment of the intestines or colon.

The DSF and/or zinc can also be conjugated, i.e., covalently linked, to a water soluble non-immunogenic high molecular weight polymer to form a polymer conjugate.

Advantageously, such polymers, e.g., polyethylene glycol, can impart solubility, stability, and reduced immunogenicity to the active compounds. As a result, the DSF, zinc or DSF zinc complex in the conjugate when administered to a patient, can have a longer half-life in the body, and exhibit better efficacy.

Oral dosage forms for controlled release or protection including microcapsules and nanocapsules generally known in the art, and hydrogels described above can all be utilized in oral administration of the DSF and/or zinc. Another preferable delivery form comprises liposomes as carriers. Liposomes are micelles formed from various lipids such as cholesterol, phospholipids, fatty acids, and derivatives thereof. The DSF and/or zinc can be enclosed within such micelles.

In certain aspects, the pharmaceutical compositions comprise DSF and zinc. The zinc can be in the form of, but is not limited to, zinc gluconate. In certain embodiments, the pharmaceutical composition described herein, comprise 0.01-0.1 mg, 0.1-1 mg, 1.0-10.0 mg, 10.0-20 mg, 20-30 mg, 30-40 mg, 40-50 mg 50-60 mg, 60-70 mg, 70-80 mg, 80-90 mg, 90-100 mg, 100-150 mg, 150-200 mg, 200-300 mg, 300-400 mg, 400-500 mg and 500-1,000 mg of DSF. In certain embodiments, the pharmaceutical compositions described herein, comprise 0.01-0.1 mg, 0.1-1 mg, 1.0-10.0 mg, 10.0-20 mg, 20-30 mg, 30-40 mg, 40-50 mg 50-60 mg, 60-70 mg, 70-80 mg, 80-90 mg and 90-100 mg of zinc. In certain embodiments, the pharmaceutical compositions described herein, comprise 0.01-0.1 mg, 0.1-1 mg, 1.0-10.0 mg, 10.0-20 mg, 20-30 mg, 30-40 mg, 40-50 mg 50-60 mg, 60-70 mg, 70-80 mg, 80-90 mg and 90-100 mg of zinc gluconate.

In certain embodiments, the DSF is formulated to be released immediately upon ingestion, and the zinc is formulated to be released between 1 min and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of the DSF. In certain embodiments, the zinc is formulated to be released immediately upon ingestion, and the DSF is formulated to be released between 1 min and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of the zinc. In certain embodiments, the onset of release of the DSF is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h before the release of the zinc. In certain embodiments, the onset of release of the zinc is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of DSF. In certain embodiments, the onset of release of the zinc is formulated to be released between 1 and 5 min, 5 min and 30 min, 30 min and 45 min, 45 min and 1 h, 1 h and 2 h, 2 h and 8 h before the release of the DSF. In certain embodiments, the onset of release of the DSF is formulated to be released between 1 and 5 min, 5 min and 30 min, 30 min and 45 min, 45 min and 1 h, 1 h and 2 h, 2 h and 3 h, 1 h and 3 h, 1 h and 4 h, 1 h and 5 h, 2 h and 4 h, 2 h and 5 h, or 3 h and 8 h after the release of the zinc.

In certain embodiments, the DSF is formulated to be released in the stomach and the zinc is formulated to be released in the intestines. In certain embodiments, the zinc is formulated to be released in the stomach and the DSF is formulated to be released in the intestines. In certain embodiments, the DSF is formulated to begin release in the stomach and the zinc is formulated to begin release in the intestines. In certain embodiments, the zinc is formulated to begin release in the stomach and the DSF is formulated to begin release in the intestines. In certain embodiments, the DSF is formulated to complete release in the stomach and the zinc is formulated to complete release in the intestines. In certain embodiments, the zinc is formulated to complete release in the stomach and the DSF is formulated to complete release in the intestines. In certain embodiments, the DSF is formulated to be released in the stomach and the zinc is formulated to be released in the colon. In certain embodiments, the zinc is formulated to be released in the stomach and the DSF is formulated to be released in the colon.

In certain embodiments, the oral dosage form comprises DSF in solid form and zinc in solid form. In certain embodiments, the oral dosage form comprises DSF in liquid form and zinc in solid form. In certain embodiments, the oral dosage form comprises both DSF and zinc in liquid form. In certain embodiments, the oral dosage form comprises zinc in liquid form and DSF in solid form.

In certain embodiments, the oral dosage form comprises DSF and zinc located in different layers. In certain embodiments, the DSF is in the outer layer and the zinc is located in a layer underneath the layer comprising DSF. In certain embodiments, the zinc is in the outer layer and the DSF is located in a layer underneath the layer comprising zinc. In certain embodiments, there are one or more intermediate layers. In certain embodiments, the intermediate layers do not comprise DSF or zinc. In certain embodiments, the dosage form is a core compressed matrix tablet, wherein the DSF or zinc is located in the interior core center of the tablet and the outer layer is an immediate release layer comprising DSF or zinc. In certain embodiments, the interior core center comprises granules that contain DSF or zinc. In certain embodiments, the oral dosage form is a bi-layer tablet wherein, an immediate release layer comprising DSF or zinc is adjacent to a sustained release layer comprising DSF or zinc. In certain embodiments, one or more of the layers comprise an enteric coating. In certain embodiments, one or more of the layers comprise a disintegrant or a superdisintegrant. In certain embodiments, one or more of the layers comprise a matrix for retaining the DSF and/or zinc in the layer upon ingestion. In certain embodiments, one or more of the layers comprise a polymeric material for increasing retention of the DSF and/or zinc in oral dosage form upon ingestion.

In certain embodiments, the oral dosage form comprises one or more types of granules. In certain embodiments, the oral dosage form is a capsule comprising one or more types of granules, wherein one granule is an immediate release granule comprising DSF or zinc and the other type of granule is a delayed release granule comprising DSF or zinc. In certain embodiments, the granules are 0.01-0.1 mm, 0.1-0.25 mm, 0.25-0.5 mm, 0.5-0.75 mm, 0.75-1.0 mm, or 1.0 mm-2.0 mm, in maximum diameter, height or width. In certain embodiments, the oral dosage form comprises granules comprising DSF. In certain embodiments, the oral dosage form comprises granules comprising zinc. In certain embodiments, the oral dosage form comprises at least two types of granules, wherein one type of granule comprises DSF and another type of granule comprises zinc. In certain embodiment, the granules comprise at least one disintegrant or a superdisintegrant. In certain embodiments, the granules are coated with an enteric coating. In certain embodiments, one or more of the granules comprise a matrix for retaining the DSF and/or zinc in the granule. In certain embodiments, one or more of the granules comprise a polymeric material for increasing retention of the DSF and/or zinc in the granule upon ingestion. In certain aspects, the granules are minitablets.

In certain embodiments, the oral dosage form comprises a matrix for controlled release of DSF and/or zinc. In certain embodiments the matrix is hydrophobic. In certain embodiments, the matrix is hydrophilic. In certain embodiments, the matrix is a polymer for controlled release of DSF and/or zinc. In come embodiments, the oral dosage form comprises a polymer device comprising a polymeric carrier for controlled release of DSF and/or zinc.

In certain embodiments, the oral dosage form controls the release of DSF and/or zinc by a diffusion-controlled system as described above.

In certain embodiments, the oral dosage form controls the release of DSF and/or zinc by an osmotic-controlled system as described above.

In certain embodiments, the oral dosage form controls the release of DSF and/or zinc by a chemically-controlled system as described above.

In certain embodiments, the oral dosage form controls the release of DSF and/or zinc by externally-triggered systems as described above.

In certain embodiments, the oral dosage form comprises an enteric coating or a gastro-resistant composition. In certain embodiments, the enteric coating or gastro-resistant composition prevent release of DSF or zinc at a pH less than 2.5, less than 3.0, less than 4.0, less than 5.0, 6.0, less than 6.2 or less than 7.0. In certain embodiments, the enteric coating or gastro-resistant composition is an acid-soluble composition and delays release of DSF or zinc upon exposure to a pH less than 2.5, less than 3.0, less than 4.0, less than 5.0, 6.0, less than 6.2 or less than 7.0.

In certain embodiments, the oral dosage form comprises a composition that allows release of DSF or zinc upon exposure to an acidic solution with a pH less than 2.5, less than 3.0, less than 4.0, less than 5.0, less than 6.0, less than 6.2 or less than 7.0.

In certain embodiments, the DSF and/or zinc are administered in combination with other therapeutic agents that treats or prevents another disease or symptom in the subject treated. Such other therapeutic agents include, but are not limited to, antiviral agents, antibiotics, antifungal agents, anti-inflammation agents, antithrombotic agents, cardiovascular drugs, cholesterol lowering agents, hypertension drugs, and the like.

5.4.3. DSF and Zinc Staggered Release Oral Dosage Forms

In certain preferred embodiments, the oral dosage form described herein comprises a capsule containing at least one disulfiram minitablet and at least one zinc minitablet, wherein the minitablets are coated to cause staggered release of the disulfiram and zinc upon administration. In certain preferred embodiments, the oral dosage form described herein comprises a capsule containing at least one disulfiram minitablet and at least one zinc minitablet, wherein each disulfiram minitablet and zinc minitablet comprises a core, wherein each core contains disulfiram or zinc and one or more excipients. In certain embodiments, the capsule is a hard gelatin capsule. In certain embodiments, the capsule is a soft gelatin capsule. In certain embodiments the zinc core comprises zinc gluconate and/or zinc glycinate.

In certain embodiments, the capsule contains 1, 2, 3, 4, 5, 6, 7, 8, 9, 10, or more zinc minitablets. In certain embodiments, the capsule contains 1, 2, 3, 4, 5, 6, 7, 8, 9, 10, or more disulfiram minitablets.

In certain embodiments, the disulfiram minitablets within a capsule collectively contain 20 mg DSF, 30 mg DSF, 40 mg DSF, 50 mg DSF, 60 mg DSF, 70 mg DSF, 80 mg DSF, 90 mg DSF, 100 mg DSF, or 120 mg DSF.

In certain embodiments, the one or more excipients are colloidal silicon dioxide, anhydrous lactose, magnesium stearate, microcrystalline cellulose, sodium starch glycolate, stearic acid, anhydrous lactose, sodium croscarmellose, crospovidone, colloidal silicon dioxide, magnesium stearate, talc, or combinations thereof.

In certain embodiments, the zinc minitablets within a capsule collectively contain any amount in the range of 10-300 mg zinc. In certain embodiments, the zinc minitablets within a capsule collectively contain 10 mg zinc, 0.50 mg zinc, 100 mg zinc, 150 mg zinc, 200 mg zinc, 250 mg zinc, or 300 mg zinc.

In certain embodiments, each zinc minitablet contains any amount in the range of 1-150 mg zinc. In certain embodiments, each zinc minitablet contains 1 mg zinc, 5 mg zinc, 10 mg zinc, 20 mg zinc, 25 mg zinc, 30 mg zinc, 40 mg zinc, 50 mg zinc, 60 mg zinc, 70 mg zinc, 80 mg zinc, 90 mg zinc, 100 mg zinc or 150 mg zinc.

In certain embodiments, the zinc and/or disulfiram minitablet cores are coated external to the core with a coating. In certain embodiments, the disulfiram minitablet cores are coated with a first coating external to the core. In certain embodiments, the disulfiram first external coating is an aqueous film coating. In certain embodiments, the aqueous film coating is a pH-insensitive coating. In certain embodiments, the coating is a pH-insensitive coating that does not delay release of the disulfiram and/or causes immediate onset of release of the disulfiram upon ingestion. In certain embodiments, the pH-insensitive coating comprises low viscosity hydroxypropyl methylcellulose (HPMC). In certain embodiments, the pH-insensitive coating comprises plasticizers. In certain embodiments, the pH-insensitive coating comprises optional pigments. In certain embodiments, the pH-insensitive coating comprises Opadry®, Opadry® II, Opadry® II 85, Opadry® AMB, sodium carboxymethylcellulose (NaCMC), polyvinol alcohol (PVA), or combinations thereof. In certain embodiments, the disulfiram first external coating is present at a thickness, measured as minitablet weight gain upon application, of approximately 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, or 25%.

In certain embodiments, the zinc minitablet cores are coated with an optional first coating external to the core. In certain embodiments, the zinc optional first external coating is an aqueous film coating. In certain embodiments, the optional aqueous film coating is a pH-insensitive coating. In certain embodiments, the coating is a pH-insensitive coating that does not delay release of the zinc and/or causes immediate onset of release of the zinc upon ingestion. In certain embodiments, the pH-insensitive coating comprises low viscosity hydroxypropyl methylcellulose (HPMC). In certain embodiments, the pH-insensitive coating comprises plasticizers. In certain embodiments, the pH-insensitive coating comprises optional pigments. In certain embodiments, the pH-insensitive coating comprises Opadry®, Opadry® II, Opadry® II 85, Opadry® AMB, sodium carboxymethylcellulose (NaCMC), polyvinol alcohol (PVA), or combinations thereof. In certain embodiments, the zinc first external coating is present at a thickness, measured as minitablet weight gain upon application, of approximately 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, or 25%.

In certain embodiments, the zinc minitablet cores are coated with a second coating external to the first external coating. In certain embodiments, the zinc second external coating is a pH-sensitive delayed release coating. In certain embodiments, the zinc second external coating is a pH-sensitive delayed release coat that dissolves upon exposure to an acidic solution with a pH less than 2.5, less than 3.0, less than 3.5, less than 4.0, less than 4.5, less than 5.0, less than 5.5, less than 6.0, less than 6.2, less than 6.5, less than 7.0, less than 7.1, less than 7.2, or less than 7.5.

In certain embodiments, the pH-sensitive delayed release coating dissolves at a pH greater than 5.0, greater than 5.5, greater than 6.0, greater than 6.5, greater than 7.0, greater than 7.1 or greater than 7.2. In certain embodiments, the zinc second external coating comprises an aqueous acrylate/methacrylate copolymer. In certain embodiments, the zinc second external coating comprises Acryl-EZE®, Eudragit® L-30D-55, Eudragit® L-100-55, Eudragit® L-100, Eudragit® FS 30 D, Eudragit® S-100, or combination thereof. In certain embodiments, the zinc first external coating is present at a thickness, measured as minitablet weight gain upon application, of approximately 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%11%, 12%, 13%, 14%, 15%, 16%, 17%, 18%, 19%, 20%, 21%, 22%, 23%, 24%, or 25%.

In certain embodiments, the zinc minitablet cores are coated with a third coating external to the second external coating. In certain embodiments, the zinc third external coating is a pH-insensitive delayed release coating. In certain embodiments, the zinc third external coating comprises an acrylate/methacrylate copolymer. In certain embodiments, the zinc third external coating comprises copolymers of Ethyl acrylate, methyl methacrylate and methacrylic acid ester with quaternary ammonium groups. In certain embodiments, the zinc third external coating comprises Eudragit® series RL, RS, NE and NM copolymers or combinations thereof that exhibit pH-independent solubility. In certain embodiments, the zinc third external coating comprises Eudragit® RL 30D or Eudragit® RS 30D. In certain embodiments, the zinc third external coating enables drug release more than 0.5 h, 1.0 h, 1.5 h, 2.0 h, 2.5 h, 3.0 h, 3.5 h, 4.0 h, 4.5 h or 5.0 h after oral administration.

The pharmaceutically useful compounds according to the present invention are administered preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of cancer or hyperproliferative disorder being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16$^{th}$ edition, Osol, A. (ed.), 1980.

In certain embodiments, a pharmaceutical composition or dosage form are administered alone or in combination with other treatments, either simultaneously or sequentially, depending upon the condition to be treated.

5.5. Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature.

Figure 1A:
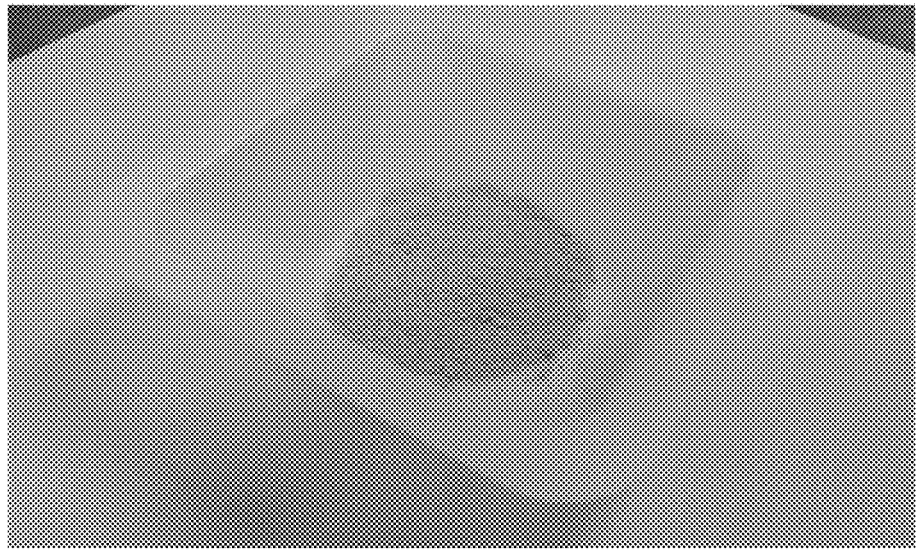
FIG. 1A depicts a blend of DSF and copper gluconate formed using a mortar and pestle.

5.5.1. Example 1: Disulfiram and Copper Gluconate Form a Precipitate at Low pH As part of an effort to design an oral dosage form combining fixed doses of disulfiram and copper gluconate for use in upcoming clinical trials (see Example 7 below), we blended 80 mg of disulfiram and 10 mg of copper gluconate using a mortar and pestle (FIG. 1A). To simulate the pH of the stomach, the blend was then mixed with 100 mL of 0.1N HCL.

Figure 1B:
FIG. 1B depicts the formation of a black precipitate upon mixing of the DSF and copper gluconate blend with 0.1 N HCL.

Immediately upon mixing, however, a dark black precipitate formed (FIG. 1B). The precipitation was complete after 1 hour after mixing.

It is known that the two active ingredients must be administered in sufficient temporal proximity to allow formation of copper-disulfiram complexes. However, the precipitate suggests that simultaneous oral administration of disulfiram and copper would provide poor bioavailability of both active ingredients, leading us to conclude that staggered oral administration is preferable to ensure maximal bioavailability, and may in fact be required to achieve therapeutic levels of the copper-disulfiram complexes in vivo.

5.5.2. Example 2: Excipient Compatibility of Disulfiram and Copper Gluconate Protocol As a predicate to designing an oral dosage form capable of providing staggered release of disulfiram and copper, excipient compatibility of disulfiram and copper gluconate are tested in pharmaceutical compositions comprising both active ingredients. The following excipients that have been previously used in FDA-approved products are tested: microcrystalline cellulose (MCC), and lactose anhydrous, as fillers; croscarmellose sodium, and crospovidone as disintegrants; colloidal silicon dioxide as glidant; magnesium stearate and talc as lubricants and anti-adherents.

The individual excipients are blended with copper gluconate (at 10.71 mg strength), with disulfiram (at 40 mg strength) in a ratio of 10:1, and with combined disulfiram and copper gluconate; the blend is prepared by mixing the active ingredient(s) with excipient in either a mortar and pestle or a V blender of appropriate size. The blends are analyzed for uniformity. The blend is then split into two portions. One portion of the blend is stored in glass bottles (with and without caps) and the other portion of the blend is filled in capsules. To compare with the active pharmaceutical ingredients ("API") as controls, (i) a blend of copper gluconate and disulfiram is stored in glass bottles (with and without caps), and (ii) a blend of copper gluconate and disulfiram is encapsulated. The capsules are stored in glass bottles (with and without caps). All the bottles are subjected to stability testing at 50° C., 40° C./75 relative humidity ("RH") and 25° C./60 RH for 2, 4, 8 and 12 weeks and analyzed for appearance, assay, degradants and impurity.

In addition to preparation of ternary blends (disulfiram+copper gluconate+excipient) and API controls (disulfiram+copper gluconate without excipient) as explained above, a complete formula including fillers, disintegrant, glidant and lubricants is prepared. A representative formula of the blend is shown below:

TABLE 1

| Ingredients | Amount (mg) per capsule | %(w/w) |
|---|---|---|
| Copper Gluconate | 10.71 | 5.088853 |
| Disulfiram | 40 | 19.00599 |
| Lactose monohydrate | 74 | 35.16108 |
| Microcrystalline cellulose ("MCC") | 74 | 35.16108 |
| Croscarmellose | 7.5 | 3.563623 |
| Colloidal Silicon Dioxide | 1.5 | 0.712725 |
| Magnesium Stearate | 0.25 | 0.118787 |
| Talc | 2.5 | 1.187874 |
| Total | 210.46 | 100.00% |

Samples from open bottles are tested first. If assay of the actives is determined to be low or if there are other indications of degradation (e.g., color change) then samples from closed bottles are tested. Only the 50 degree and 40 degree/75% RH samples are tested until an interaction is discovered, at which point the 25° C./60 RH temperature samples are tested.

Results

Disulfiram and copper gluconate were blended with individual excipients, the full excipient mixture ("full blend"), and as a simple mixture without excipients ("control") (Tables 2-5). The stability of these variants was visually and analytically evaluated over two weeks at storage conditions of 25, 40 and 50 degrees Celsius as bulk powders and as capsules stored with and without a desiccant in sealed polypropylene bottles (FIG. 2, taken at time T0).

TABLE 2

Excipient to Drug Ratio

| # | Excipient | Excipient (g) | Disulfiram (g) | CuGlu$_2$ (g) | Total (g) | Ratio |
|---|---|---|---|---|---|---|
| 1 | Lactose anhydrous | 182.6 | 28.8 | 7.7 | 219.1 | 5.00 |
| 2 | MCC | 182.6 | 28.8 | 7.7 | 219.1 | 5.00 |
| 3 | Croscarmellose | 182.6 | 28.8 | 7.7 | 219.1 | 5.00 |
| 4 | Colloidal SiO$_2$ | 40.0 | 28.8 | 7.7 | 76.5 | 1.10 |
| 5 | Mg Stearate | 40.0 | 28.8 | 7.7 | 76.5 | 1.10 |
| 6 | Talc | 40.0 | 28.8 | 7.7 | 76.5 | 1.10 |
| 7 | Control | 0.0 | 28.8 | 7.7 | 36.5 | — |

TABLE 3

Composition of representative formula blend

| Ingredient | Amount in capsule (mg) | Amount in the blend (g) | %, w/w |
|---|---|---|---|
| Cu Gluconate | 10.71 | 7.71 | 5.09% |
| Disulfiram | 40.00 | 28.80 | 19.01% |
| Lactose anhydrous | 74.00 | 53.28 | 35.16% |
| MCC | 74.00 | 53.28 | 35.16% |
| Croscarmellose | 7.50 | 5.40 | 3.56% |
| Colloidal SiO$_2$ | 1.50 | 1.08 | 0.71% |
| Mg Stearate | 0.25 | 0.18 | 0.12% |
| Talc | 2.50 | 1.80 | 1.19% |
| Total | 210.46 | 151.53 | 100.00% |

TABLE 4

Disulfiram assay at T = 0

| Blend | API content | Average |
|---|---|---|
| Lactose anhydrous 1 | 96.1% | 99.9% |
| Lactose anhydrous 2 | 103.2% | |
| Lactose anhydrous 3 | 100.4% | |
| MCC 1 | 93.2% | 94.8% |
| MCC 2 | 93.2% | |
| MCC 3 | 98.1% | |
| Croscarmellose 1 | 89.9% | 94.0% |
| Croscarmellose 2 | 93.2% | |
| Croscarmellose 3 | 98.9% | |
| Colloidal SiO$_2$ 1 | 104.6% | 101.6% |
| Colloidal SiO$_2$ 2 | 99.3% | |
| Colloidal SiO$_2$ 3 | 100.8% | |
| Magnesium Stearate 1 | 97.2% | 98.7% |
| Magnesium Stearate 2 | 97.8% | |
| Magnesium Stearate 3 | 101.0% | |
| Talc 1 | 95.8% | 6.0% |
| Talc 2 | 95.7% | |
| Talc 3 | 96.5% | |
| Control 1 | 99.8% | 97.6% |
| Control 2 | 96.6% | |
| Control 3 | 96.3% | |
| Full Blend 1 | 95.1% | 94.2% |
| Full Blend 2 | 94.1% | |
| Full Blend 3 | 93.5% | |

TABLE 5

Copper assay at T = 0

| Blend | API content | Average |
|---|---|---|
| Lactose anhydrous 1 | 94.8% | 96.2% |
| Lactose anhydrous 2 | 99.8% | |
| Lactose anhydrous 3 | 93.9% | |
| MCC 1 | 93.7% | 95.5% |
| MCC 2 | 97.3% | |
| MCC 3 | 95.6% | |
| Croscarmellose 1 | 97.6% | 96.4% |
| Croscarmellose 2 | 95.9% | |
| Croscarmellose 3 | 95.8% | |
| Colloidal $SiO_2$ 1 | 66.4% | 79.7% |
| Colloidal $SiO_2$ 2 | 90.4% | |
| Colloidal $SiO_2$ 3 | 82.2% | |
| Magnesium Stearate 1 | 99.9% | 94.1% |
| Magnesium Stearate 2 | 90.8% | |
| Magnesium Stearate 3 | 91.6% | |
| Talc 1 | 101.8% | 99.8% |
| Talc 2 | 104.6% | |
| Talc 3 | 93.0% | |
| Control 1 | 85.9% | 95.7% |
| Control 2 | 94.9% | |
| Control 3 | 106.4% | |
| Full Blend 1 | 96.3% | 96.7% |
| Full Blend 2 | 96.2% | |
| Full Blend 3 | 97.7% | |

TABLE 6

Disulfiram Assay T = 2 weeks

| Blend | Disulfiram, % |
|---|---|
| Lactose anhydrous 50° C. powder | 52.1% |
| Lactose anhydrous 50° C. capsules | 28.8% |
| Lactose anhydrous 40° C./75 RH powder | 72.3% |
| Lactose anhydrous 40° C./75 RH capsules | 78.8% |
| Lactose anhydrous 25° C./60 RH powder | 76.0% |
| Lactose anhydrous 25° C./60 RH capsules | 73.4% |
| $CuGlu_2$ + Disulfiram 50° C. powder | 72.6% |
| $CuGlu_2$ + Disulfiram 50° C. capsules | 52.7% |
| $CuGlu_2$ + Disulfiram 40° C./75 RH powder | 51.8% |
| $CuGlu_2$ + Disulfiram 40° C./75 RH capsules | 54.0% |
| $CuGlu_2$ + Disulfiram 25° C./60 RH powder | 85.5% |
| $CuGlu_2$ + Disulfiram 25° C./60 RH capsules | 74.8% |
| Full Formula 50° C. Without Desiccant | Not sampled |
| Full Formula 50° C. With Desiccant | 30.4% |
| Full Formula 40° C./75 RH Without Desiccant | 62.9% |
| Full Formula 40° C./75 RH With Desiccant | 74.0% |
| Full Formula 25° C./60 RH Without Desiccant | 65.5% |
| Full Formula 25° C./60 RH With Desiccant | 68.9% |

At two weeks, most of the mixtures had changed color, indicating chemical degradation, and the simple mixture of copper gluconate and disulfiram had turned black. Color development was greatest at the highest temperature in containers without desiccant packages.

Analytical determination of disulfiram content of the test mixtures confirmed disulfiram degradation and production of degradants with unknown structures (Table 6 and FIGS. 3-5).

The precipitate that formed in vitro in the presence of HCl in Example 1 suggested that simultaneous dosing of disulfiram and copper could reduce bioavailability through formation of a precipitate in the stomach at acid pH. The results from the excipient compatibility studies in the present Example further suggest that simultaneous dosing could also cause degradation of disulfiram, further reducing efficacy. The disulfiram degradation also suggest that a means of physically separating the disulfiram and copper gluconate active ingredients is required to ensure stability of the disulfiram and copper gluconate in any combined unit dosage form.

5.5.3. Example 3: Staggered Release Oral Dosage Form Comprising Disulfiram and Copper Design Parameters An oral unit dosage form configured to release disulfiram before copper is prepared as follows. Disulfiram and copper gluconate are separately formulated for common inclusion in a capsule containing both active ingredients. The capsule comprises two distinct populations of granules, wherein each population comprises either disulfiram or copper gluconate. The disulfiram granules comprise at least one appropriate excipient and are configured for immediate release upon ingestion. The copper gluconate granules comprise at least one appropriate excipient and are coated with a gastro-resistant coating to delay the release of copper gluconate 30 min to 2 hours after ingestion of the capsule. Each capsule contains 40 mg of disulfiram and 1.5 mg copper gluconate.

Stability and Delayed Release of Copper in Coated Minitablets

Various means of separating the two medicaments were considered, including use of a side-by-side tablet, use of a two compartment capsule, use of a capsule containing one of the components inside a second capsule which would contain the other component, and the preparation of "minitablets" from one or both of the medicaments which would be subsequently coated with a protective barrier. The use of minitablets was selected for further development since they would provide the most flexibility in the final single dose form. With this approach, the coating(s) could be applied not only to physically separate the two drug components, but also to change the in vivo drug delivery profile by dissolution delay of one of the components while providing near immediate dissolution of the other component. Additionally, by choosing the amount of active ingredient in the minitablets appropriately, both total dose and dose ratio of the two components in a single capsule could be modified by simply adding more or fewer minitablets to the capsule.

The initial target for the combined dose form was immediate dissolution of the disulfiram minitablets in the stomach followed by dissolution of the copper gluconate 2 to 4 hours later in the small intestine. To achieve this, as well as provide a physical separation of the two medicaments, uncoated minitablets of both disulfiram and copper gluconate were prepared, and the copper gluconate tablets were coated with a pH sensitive coating that dissolves at a pH greater than ~5.5, which is the nominal pH of the small intestine. Conceptually, this would provide for physical separation of the two medicaments in the capsule, and the copper gluconate release would be delayed until the coating environment was at an appropriate pH, >5.5 in this instance.

Copper gluconate and disulfiram minitablets were treated with different coating strategies, with the goal of identifying coatings that would maintain the chemical stability of the respective active ingredients through the storage period, and that would permit minimal interaction in the GI tract. Copper gluconate and disulfiram minitablets with various sizes (e.g., 3-4 mm in diameter) and shapes (e.g., rod, round, etc.) were produced by a KORSCH XL 100 tablet press and evaluated in size 00 capsules. The 4 mm minitablet was selected and used for coating studies. The dose, dimension, and average weight of 4 mm copper gluconate minitablets are summarized in Table 7.

TABLE 7

Uncoated copper gluconate minitablet dimensions and weight

| Dimension (Diameter × Height) | Average weight |
|---|---|
| 4.02 mm × 4.28 mm | 65.1 ± 1.07 mg (equal to 0.5 mg of Cu) |

To create a delayed release profile, the copper gluconate tablet cores were initially coated with an Opadry® immediate release (HPMC, 6 mPa) subcoat to smooth edges of the core tablet prior to barrier membrane coating. The subsequently applied outer barrier membrane coating was Acryl-EZE® EUIDRAGIT® L100-55, a pH dependent coating material that starts dissolving at pH values above 5.5, applied at different weight gains as shown in Table 8.

TABLE 8

Percent weight gain of copper gluconate tablets coated Opadry and Acryl-EZE ®

| Tablet coats | 1 | 2* | 3 | 4* | 5 | 6 | 7* |
|---|---|---|---|---|---|---|---|
| Opadry ® (HPMC, 6 mPa; IR coat) | 2% | 2% | 2% | 2% | 2% | 2% | 2% |
| Acryl-EZE ® (Methacrylic acid copolymer type C; Enteric coat) | 8% | 10% | 12% | 14% | 16% | 18% | 20% |

*Formulation selected for the dissolution test

Since copper solubility is affected by pH, buffer, and ion effects, various buffer solutions were evaluated for the dissolution test. As can be seen in Table 9, copper from uncoated copper gluconate minitablets fully dissolved in 0.1N HCl and Citrate Buffer pH 6.2, but partially dissolved in Acetate Buffer pH 5.0 and Phosphate Buffer pH 6.5. The copper from copper gluconate minitablets coated with Acryl-EZE® at 20% weight gain also fully dissolved in Citrate Buffer pH 6.2, indicating a minimal interaction between copper and Acryl-EZE® (Table 10).

TABLE 9

Cu Assay on uncoated minitablet

| Sample # | Weight (mg) | Cu in sample (mg) | % of Label claim | Average | Medium for Assay |
|---|---|---|---|---|---|
| pH 1.2 #1 | 194.6 | 1.53 | 101.7% | 100.7% | 0.1N HCl (pH 1.2) |
| pH 1.2 #2 | 197.5 | 1.55 | 103.0% | | |
| pH 1.2 #3 | 195.8 | 1.46 | 97.3% | | |
| pH 5.0 #1 | 193.1 | 1.17 | 77.7% | 78.8% | Acetate Buffer 5.0 |
| pH 5.0 #2 | 195.6 | 1.18 | 78.3% | | |
| pH 5.0 #3 | 196.3 | 1.21 | 80.3% | | |
| pH 6.5 #1 | 195.3 | 0.14 | 9.0% | 11.0% | Phosphate Buffer 6.5 |
| pH 6.5 #2 | 197.7 | 0.21 | 13.7% | | |
| pH 6.5 #3 | 193.3 | 0.16 | 10.3% | | |
| pH 6.2 #1 | 197.99 | 1.49 | 99.0% | 104.9% | Citrate Buffer 6.2 |
| pH 6.2 #2 | 197.37 | 1.65 | 109.7% | | |
| pH 6.2 #3 | 198.08 | 1.59 | 106.0% | | |

Cu assay in accordance with SOP QC-223, the identification and quantitation of the element copper in copper gluconate capsules with EDX-7000
Each sample contained 3 minitablets weighing around 195 mg Cu assay in accordance with SOP QC-223, the identification and quantitation of the element copper in copper gluconate capsules with EDX-7000
Each sample contained 3 minitablets weighing around 195 mg

TABLE 10

Cu Assay on copper gluconate minitablets coated with Acryl-EZE ® at 20% weight gain

| Sample # | Weight (mg) | Cu in sample, mg | % of Label claim | Average | Medium for Assay |
|---|---|---|---|---|---|
| 1-pH 6.2 | 236.54 | 1.38 | 92.0% | 98.3% | Citrate Buffer 6.2 |
| 2-pH 6.2 | 238.43 | 1.55 | 103.3% | | |
| 3-pH 6.2 | 237.31 | 1.50 | 99.7% | | |
| 4-pH 6.2 | — | 0.06 | 4.0% | 4.0% | Citrate Buffer 6.2 |

Acryl-EZE ®: EUDRAGIT ® L100-55, an Evonik product
Each sample contained 3 minitablets weighing around 234 mg Acryl-EZE®: EUDRAGIT® L100-55, an Evonik product
Each sample contained 3 minitablets weighing around 234 mg The coated copper gluconate minitablets were evaluated for dissolution in 0.1 N HCl which simulates the normal stomach pH. For the dissolution testing, the copper gluconate minitablets with Acryl-EZE® at 10%, 14%, and 20% weight gains were incubated in 0.1N HCl for 2 hours, followed by either 14 hours in Acetate Buffer pH 5.0 (Table 11) or 1 hour in Citrate Buffer pH 6.0, using a United States Pharmacopeia (USP) Paddle at 50 r.p.m. at 37° C. (Table 12).

The copper gluconate minitablets with Acryl-EZE® at up to 20% weight gains showed no copper release in 0.1 N HCl and Acetate Buffer pH 5.0 but full copper release in Citrate Buffer pH 6.0. As desired, virtually no dissolution occurred at lower pH, and dissolution did occur at higher pH levels which simulates the small intestine environment. Since transit from the stomach to the upper intestine can take as long as 2 hours, the desired delayed release of copper gluconate was successfully achieved.

TABLE 11

Dissolution testing # 1 on copper gluconate minitablets coated with Acryl-EZE ® at 10%, 14%, and 20% weight gain with dissolution medium: 50 mL Acetate Buffer pH 5.0

| | | % Drug Release (at dissolution time, h) | | | | | | | |
|---|---|---|---|---|---|---|---|---|---|
| | Wt | $T_0$ | | $T_{0.5}$ | | $T_1$ | | $T_{14}$ | |
| Sample # | (mg) | Individual | Avg | Individual | Avg | Individual | Avg | Individual | Avg |
| 10-1 | 70.71 | 0.0 | 0.0 | 0.0 | 0.0 | 0.0 | 0.3 | 2.7 | 3.4 |
| 10-2 | 72.98 | 0.0 | | | | 0.7 | | 4.0 | |

TABLE 11-continued

Dissolution testing # 1 on copper gluconate minitablets coated
with Acryl-EZE ® at 10%, 14%, and 20% weight gain with
dissolution medium: 50 mL Acetate Buffer pH 5.0

% Drug Release (at dissolution time, h)

| Sample # | Wt (mg) | $T_0$ Individual | Avg | $T_{0.5}$ Individual | Avg | $T_1$ Individual | Avg | $T_{14}$ Individual | Avg |
|---|---|---|---|---|---|---|---|---|---|
| 14-1 | 75.35 | 4.0 | 4.0 | 2.7 | 2.3 | 0.3 | 0.2 | 2.3 | 1.3 |
| 14-2 | 73.45 | 4.0 | | 2.0 | | 0.2 | | 0.3 | |
| 20-1 | 75.42 | 3.0 | 5.0 | 2.6 | 3.8 | 4.5 | 3.0 | 5.3 | 4.9 |
| 20-2 | 77.73 | 7.0 | | 4.9 | | 1.5 | | 4.5 | |

TABLE 12

Dissolution testing # 2 on copper gluconate minitablets coated
with Acryl-EZE ® at 10%, 14%, and 20% weight gain with
dissolution medium Citrate Buffer pH 6.0

% Drug Release (at dissolution time, h)

| Sample # | Weight (mg) | $T_0$ Individual | Avg | $T_{0.5}$ Individual | Avg | $T_1$ Individual | Avg |
|---|---|---|---|---|---|---|---|
| 10-1 | 213.19 | 0.0 | 0.5 | 98.3 | 85.9 | 106.4 | 99.6 |
| 10-2 | 216.78 | 1.0 | | 73.6 | | 92.8 | |
| 14-1 | 221.48 | 2.7 | 1.3 | 64.9 | 70.7 | 92.8 | 93.3 |
| 14-2 | 223.81 | 0.0 | | 76.5 | | 93.7 | |
| 20-1 | 237.09 | 1.7 | 1.7 | 35.5 | 38.2 | 85.8 | 84.8 |
| 20-2 | 236.83 | 1.7 | | 40.8 | | 83.8 | |

5.5.4. Example 4: Stability of Enteric Coated Copper Gluconate Minitablets

To confirm acceptable shelf stability of the coated copper gluconate minitablets alone, stability studies were conducted. HPLC assays were performed on uncoated or enteric coated copper gluconate and uncoated disulfiram stored at 40° C., 75% relative humidity (RH). Percent drug recovery in Citrate Buffer pH 6.0 was assessed (Table 13) by direct extraction of the capsule contents in 50 mL of Citrate Buffer pH 6.0. Minimal loss of either drug was detected after 2 and 3 months of storage. For uncoated disulfiram, 90.7 percent drug recovery was detected after 2 months. HPLC testing of uncoated disulfiram was performed at lower temperature storage conditions 30° C. (Table 14) and 25° C. (Table 15), and 97.8% percent disulfiram recovery was achieved after two months.

TABLE 13

Stability study on capsules with Copper Gluconate and/or Disulfiram minitablets at 40° C.
HPLC Assay

| Dosage form | API | Capsule Configuration | % Drug Recovery Initial | 1 Month | 2 Month | 3 Month |
|---|---|---|---|---|---|---|
| Size 00 capsules with added Copper gluconate tablets | Cu Gluconate (uncoated) | 6x tablets | 97.3 ± 2.455% | 101.5 ± 0.577% | 95.25 ± 0.024% | NP |
| Copper gluconate coated with Opadry ® (2% W.G.) and Acryl-EZE ® (20% W.G.) | Cu Gluconate (coated) | 6x tablets | 101.6 ± 3.102% | 93.8 ± 0.020% | 97.30 ± 0.022% | NP |
| Copper gluconate coated with Opadry ® (2% W.G.) and Acryl-EZE ® (20% W.G.) | Cu Gluconate (coated) | 3x tablets | 104.6 ± 0.007% | 107.1 ± 3.533% | 104.90 ± 0.027% | 105.91 ± 0.012% |
| Uncoated disulfiram, 20 mg | Disulfiram (uncoated) | 2x tablets | 104.1 ± 0.021% | 1st Run: 93.5 ± 0.026% 2nd Run: 99.4 ± 0.053% | 90.70 ± 0.003% | 99.03 ± 4.300% |

Table 13 Legend:
Storage condition: 40° C. ± 2° C.; 75 ± 5% RH
Data are presented as Mean ± SD (N = 3 capsules)
Cu assay in accordance with SOP QC-223, the identification and quantitation of the element copper in copper gluconate capsules with EDX-7000
HPLC assays on Copper Gluconate were performed by direct extraction of the capsule contents in the appropriate solvent. There was no grinding of tablets;
HPLC assays on Disulfiram: 20 tablets (from 10 capsules) were ground to fine powder. The amount of powder equal to 1 disulfiram tablet was taken for the assay. Samples were taken 3 times for testing;
NP: not performed;
( ) in the % drug recovery table indicates the date of tests performed;
HPLC assay on Copper Gluconate was performed in Citrate Buffer pH 6.0 (50 mL, 3 micro tablets/capsule);
1 Copper Gluconate tablet contains 0.5 mg of Cu;
1 Disulfiram tablet contains 20 mg of Disulfiram;
*2 components were separated for the testing;
W.G.: weight gain

TABLE 14

Stability study on capsules with Copper Gluconate and/or Disulfiram minitablets at 30° C.

| Dosage form | API | Capsule Configuration | % Drug Recovery | | | |
|---|---|---|---|---|---|---|
| | | | Initial | 1 Month | 2 Month | 3 Month |
| Size 00 capsules with added Copper gluconate tablets | Cu Gluconate (uncoated) | 6x tablets | NP | NP | NP | NP |
| Copper gluconate coated with Opadry ® (2% W.G.) and Acryl-EZE ® (20% W.G.) | Cu Gluconate (coated) | 6x tablets | NP | NP | NP | NP |
| Copper gluconate coated with Opadry ® (2% W.G.) and Acryl-EZE ® (20% W.G.) | Cu Gluconate (coated) | 3x tablets | NP | NP | NP | NP |
| Uncoated disulfiram, 20 mg | Disulfiram (uncoated) | 2x tablets | NP | NP | 97.8 ± 0.021%* | NP |

Table 14 Legend:
HPLC assays on stability samples
Storage condition 25° C. ± 2° C.; 60 ± 5% RH
*Data are presented as Mean ± SD (N = 6 capsules). No impurities were found in the chromatograms;
Storage orientation Upright
Data are presented as Mean ± SD (N = 3 capsules);
Cu assay was performed in accordance with SOP QC-223, the identification and quantitation of the element copper in copper gluconate capsules with EDX-7000
Disulfiram assay was performed in accordance with SOP QC-222
HPLC assays on copper gluconate were performed by direct extraction of the capsule contents in the appropriate solvent. There was no grinding of tablets;
HPLC assays on Disulfiram: 20 tablets (from 10 capsules) were ground to fine powder. The amount of powder equal to 1 disulfiram tablet was taken for the assay. Samples were taken 3 times for testing;
NP: not performed;
( ) in the % drug recovery table indicates the date of tests performed;
HPLC assay on copper gluconate was performed in Citrate Buffer pH 6.0 (50 mL, 3 micro tablets/capsule);
1 Copper Gluconate tablet contains 0.5 mg of Cu;
1 Disulfiram tablet contains 20 mg of disulfiram;
*2 components were separated for the testing;
W.G.: weight gain

TABLE 15

Stability study on capsules with Copper Gluconate and/or Disulfiram minitablets at 25° C.

| | API | Capsule Configuration | Time at condition: | | | |
|---|---|---|---|---|---|---|
| | | | Initial | 1 Month | 2 Month | 3 Month |
| | | | % Drug Recovery | | | |
| Size 00 capsules with added Copper gluconate tablets | Cu Gluconate (uncoated) | 6x tablets | NP | NP | NP | NP |
| Copper gluconate coated with Opadry ® (2% W.G.) and Acryl-EZE ® (20% W.G.) | Cu Gluconate (coated) | 6x tablets | NP | NP | NP | NP |
| Copper gluconate coated with Opadry ® (2% W.G.) and Acryl-EZE ® (20% W.G.) | Cu Gluconate (coated) | 3x tablets | NP | NP | NP | NP |
| Uncoated disulfiram, 20 mg | Disulfiram (uncoated) | 2x tablets | NP | NP | 97.8 ± 0.021%* | NP |

TABLE 15 Legend:
HPLC assays on stability samples
Storage condition 25° C. ± 2° C.; 60 ± 5% RH
Storage orientation Upright
*Data are presented as Mean ± SD (N = 6 capsules). No impurities were found in the chromatograms;
Data are presented as Mean ± SD (N = 3 capsules);
Cu assay was performed in accordance with SOP QC-223, the identification and quantitation of the element copper in copper gluconate capsules with EDX-7000
Disulfiram assay was performed in accordance with SOP QC-222
HPLC assays on copper gluconate were performed by direct extraction of the capsule contents in the appropriate solvent. There was no grinding of tablets;
HPLC assays on disulfiram: 20 tablets (from 10 capsules) were ground to fine powder. The amount of powder equal to 1 disulfiram tablet was taken for the assay. Samples were taken 3 times for testing;
NP: not performed;
( ) in the % drug recovery table
indicates the date of tests performed;
HPLC assay on copper gluconate was performed in Citrate Buffer pH 6.0 (50 mL, 3 micro tablets/capsule);
1 Copper Gluconate tablet contains 0.5 mg of Cu;
1 Disulfiram tablet contains 20 mg of disulfiram;
*2 components were separated for the testing;
W.G.: weight gain To confirm acceptable stability of the coated copper gluconate minitablets in 0.1N HCl, dissolution studies were conducted after 1 month (Table 16), 2 months and 3 months (Table 17) of storage. Samples were stored at 40° C./75% RH. A dissolution test of Copper Gluconate tablets with and without enteric coating was performed using a United States Pharmacopeia (USP) Paddle at 50 r.p.m. in 50 mL of 0.1 N HCl for 2 hours at 37° C. 0.1 N HCl was then removed and 50 mL of Citrate buffer pH 6.0 was added into the dissolution vessels for testing for up to 1.5 hours dissolution time. Dissolution of uncoated disulfiram tablets was performed with 900 mL of 2% SDS (sodium dodecyl sulfate) using a USP Paddle at 100 r.p.m. for testing for up to 2 hours dissolution time. The results listed in Tables 16 and 17 show that the coated copper gluconate minitablets are stable for at least 2 months and maintain resistance to dissolution in the acidic 0.1N HCl environment.

TABLE 16

Dissolution tests on capsules with Copper Gluconate and/or Disulfiram minitablets after one month
Storage condition 40° C. ± 2° C.; 75 ± 5% RH

| | | | Time at condition: | | | | | |
|---|---|---|---|---|---|---|---|---|
| | | | Initial | | | 1 Month | | |
| | | | | % Drug Recovery | | | | |
| Dissolution tests | API | Capsule Configuration | 2 h (T0) 0.1N HCl | 1 h Citrate Buffer pH 6.0 | 1.5 h | 2 h (T0) 0.1N HCl | 1 h Citrate Buffer pH 6.0 | 1.5 h | 2.0 h |
| Size 00 capsules with added Copper gluconate tablets | Cu Gluconate (uncoated) | 6x tablets | 85.1 ± 0.051%$^a$ | 12.8 ± 0.095%$^b$ | 11.9 ± 0.084%$^b$ | 87.1 ± 0.066% | 7.5 ± 0.062% | 7.6 ± 0.061% | NP |
| Copper gluconate coated with Opadry ® (2% W.G.) and Acryl-EZE ® (20% W.G.) | Cu Gluconate (coated) | 6x tablets | 1$^{st}$: 1.7 ± 0.0% 2$^{nd}$: 0.9 ± 0.006% | 1$^{st}$: 84.8 ± 1.4% 2$^{nd}$: 43.1 ± 0.052% | 66.9 ± 0.077% | 0.6 ± 0.006% | 40.2 ± 0.088% | 67.4 ± 0.145% | NP |
| Copper gluconate coated with Opadry ® (2% W.G.) and Acryl-EZE ® (20% W.G.) | Cu Gluconate (coated) | 3x tablets | 1.4 ± 0.015% | 77.7 ± 0.194% | 98.2 ± 0.023% | 4.0 ± 0.015% | 59.0 ± 0.032% | 80.7 ± 0.033%* [200 r.p.m.] | NP |
| | | | 30 min | 60 min 2% SLS | 120 min | 30 min | 60 min 2% SLS | 120 min | |
| Uncoated disulfiram, 20 mg | Disulfiram (uncoated) | 2x tablets | 86.9 ± 0.036% | 86.5 ± 0.034% | NP | 84.2 ± 0.024% | 93.4 ± 0.020% | 93.4 ± 0.020% | |

Table 16 Legend:
Data are presented as Mean ± SD (N = 3 capsules);
NP: not performed;
Normal dissolution testing on copper gluconate was performed at 37° C., 50 rpm, and 50 mL of dissolution media (0.1N HCl or Citrate Buffer pH 6.0);
*indicates that samples were run at 37° C. in 50 mL of dissolution media; but the stirring rate was increased to 200 r.p.m. after 1 hour time point;
Storage orientation Upright
Dissolution of disulfiram tablets was performed at 900 mL of 2% SLS, 100 rpm, 60 min of sampling intervals;
2-month data on samples at 25° C./60% RH are run with 40° C./75% RH in parallel;
( ) in the % drug recovery table indicates the date of tests performed;
**2 components were separated for the testing;
$^a$Dissolution test on copper gluconate tablets Lot# 843-1-21 without coating was ran at 37° C. and 50 r.p.m. in 50 mL of 0.1N HCl for 2 hours;
$^b$After tablets Lot# 843-1-21 were sampled, 0.1N HCl was removed and 50 mL of Citrate buffer pH 6.0 was added into the dissolution vessels for testing up to 1.5 hours dissolution time

TABLE 17

Dissolution tests on capsules with Copper Gluconate and/or Disulfiram minitablets after two or three months
Storage condition 40° C. ± 2° C.; 75 ± 5% RH

| | | | 2 Month | | | 3 Month | | |
|---|---|---|---|---|---|---|---|---|
| | | | | % Drug Recovery | | | | |
| Dissolution tests | API | Capsule Configuration | 2 h (T0) 0.1N HCl | 1 h Citrate Buffer pH 6.0 | 2 h | 2 h (T0) 0.1N HCl | 1 h Citrate Buffer pH 6.0 | 2 h |
| Size 00 capsules with added Copper gluconate tablets | Cu Gluconate (uncoated) | 6x tablets | 92.3 ± 0.007% | 6.9 ± 0.015% | 5.1 ± 0.027% | NP | NP | NP |

TABLE 17-continued

Dissolution tests on capsules with Copper Gluconate and/or Disulfiram minitablets after two or three months
Storage condition 40° C. ± 2° C.; 75 ± 5% RH

| | | | | | | | | |
|---|---|---|---|---|---|---|---|---|
| Copper gluconate coated with Opadry® (2% W.G.) and Acryl-EZE® (20% W.G.) | Cu Gluconate (coated) | 6x tablets | 3.3 ± 0.009% | 58.2 ± 0.018% | 84.3 ± 0.025% | NP | NP | NP |
| Copper gluconate coated with Opadry® (2% W.G.) and Acryl-EZE® (20% W.G.) | Cu Gluconate (coated) | 3x tablets | 3.0 ± 0.003% | 60.7 ± 0.026% | 88.8 ± 0.049% | 1.78 ± 0.016% | 68.65 ± 0.030% | 97.52 ± 0.071% |
| | | | 30 min | 60 min 2% SLS | 120 min | 30 min | 60 min 2% SLS | 120 min |
| Uncoated disulfiram, 20 mg | Disulfiram (uncoated) | 2x tablets | 78.67 ± 0.006% | 84.67 ± 0.012% | 87.0 ± 0.026% | 80.69 ± 0.077% | 89.79 ± 0.085% | 91.26 ± 0.088% |

Table 17 Legend:
Data are presented as Mean ± SD (N = 3 capsules);
NP: not performed;
Normal dissolution testing on copper gluconate was performed at 37° C., 50 rpm, and 50 mL of dissolution media (0.1N HCl or Citrate Buffer pH 6.0) - according to SOP QC-223;
* indicates that samples were run at 37° C. in 50 mL of dissolution media; but the stirring rate was increased to 200 r.p.m. after 1 hour time point;
Dissolution of disulfiram tablets was performed at 900 mL of 2% SLS, 100 rpm, 60 min of sampling intervals;
2-month data on samples at 25° C./60% RH are run with 40° C./75% RH in parallel;
( ) in the % drug recovery table indicates the date of tests performed;
**2 components were separated for the testing;
a: Dissolution test on copper gluconate tablets Lot# 843-1-21 without coating was ran at 37° C. and 50 r.p.m. in 50 mL of 0.1N HCl for 2 hours;
b: After tablets Lot# 843-1-21 were sampling, 0.1N HCl was removed and 50 mL of Citrate buffer pH 6.0 was added into the dissolution vessels for testing up to 1.5 hours dissolution time

5.5.5. Example 5: Formulations for Patients with Higher Stomach pH Levels

A second dissolution target was established for patients with higher stomach pH levels, e.g., patients undergoing proton pump inhibitor treatment concurrent with chemotherapy. The coated copper gluconate minitablets discussed above were further coated with a coating that dissolves as a function of time (e.g., exhibits pH-independent swelling) to provide additional protection against copper gluconate dissolution in the stomach. Coating studies were performed on copper gluconate minitablets coated with: a) Opadry® (4.5% W.G.) and Eudragit® FS 30 D (12% W.G.); b) Opadry® (4.5% W.G.), Eudragit® FS 30 D (12% W.G.) and Eudragit® RL (2%, 4%, and 6% W.G.). Eudragit® RS 30D and Eudragit® RL 30D are pH-independent polymers. Both Eudragit® RS 30D and RL 30D are composed of ethyl acrylate, methyl methacrylate, and a low content of methacrylic acid ester with quaternary ammonium groups. Eudragit® RL 30D contains more ammonium groups than Eudragit® RS 30D, thus it has faster water permeability than Eudragit® RS 30D.

Minitablets were produced as follows: 2 kg of copper gluconate powder blend was prepared and around 1.4 kg of copper gluconate minitablets was obtained for coating trials after the process of tableting. Due to the low weight variation (>95% of tablets within target weight 7.5%) observed on tablets produced by the tablet press, these minitablets were directly used for coating trials without evaluating weight. The minitablets were first coated with 4.5% weight gain of Opadry® Clear (Colorcon, Calif.) and 12% weight gain of Eudragit® FS30D (Evonik, N.J.). The initial dissolution testing was performed as follows: three coated copper gluconate tablets were put in a size 00 Licaps® gelatin capsule prefilled with four disulfiram tablets (10 mg of disulfiram each). These capsules were then packaged in a 60 cc bottles for stability testing. Results are shown in Table 18.

Minitablets pre-coated with Opadry® Clear 4.5% W.G. and Eudragit® FS30D (12% W.G.) were then further coated with 2%-10% weight gain of Eudragit® RL30D (Evonik, N.J.). Dissolution testing was performed and drug recovery was determined every hour between 1 h and 8 h. The results presented in Table 19 and FIG. 6 show that the additional coating of Eudragit® RL30D of 2%, 4% or 8% weight gain successfully delayed the release of copper beyond the minitablets coated with Opadry® Clear and 12% weight gain of Eudragit® FS30D alone. In particular, the copper gluconate tablets coated with Eudragit® FS (12% weight gain) and Eudragit® RL (2% weight gain) displayed no copper release in 0.1 N HCL and 91.03% recovery after 3 hours in sodium citrate pH 7.4.

Dissolution testing was also performed on minitablets coated with pH-sensitive coats that exhibit swelling at higher pH. To assess coat combinations that may provide drug recovery at higher pH, copper gluconate minitablets were coated with Opadry® (3% W.G.) and Eudragit® FS 30 D (4% or 6% W.G.), Table 20. Eudragit® FS 30 D is a pH-dependent coating that allows drug release at pH >7. The copper gluconate minitablets coated with Opadry® (3% W.G.) and Eudragit® FS 30 D (4% W.G.) demonstrated 88.18% release of copper after 2 hours in sodium citrate pH 7.4 and 95.43% release of copper after 2.5 hours in sodium citrate pH 7.4. The copper gluconate minitablets coated with Opadry® (3% W.G.) and Eudragit® FS 30 D (6% W.G.) demonstrated 61.02% release of copper after 2 hours in sodium citrate pH 7.4 and 88.48% release of copper after 2.5 hours in sodium citrate pH 7.4 (Tables 20, 21 and FIG. 7).

Further dissolution studies are performed with copper gluconate minitablets coated with 3% Opadry®, 8% Acryl-EZE®, and 2% Eudragit® RL. Copper in the minitablets is intended to be released in small intestine for patients with and without treatment of proton pump inhibitors (PPI)s having a neutral or acidic stomach pH, respectively. Copper release is expected to be slightly earlier in the presence of treatment with PPIs and relatively slower for an acidic stomach. 2% Eudragit® RL coating gives an additional 2-3 hour delay of copper release beyond the 2 hour protection from acid provided by Acryl-EZE® alone. The actual dissolution profile of copper gluconate with 8% Acryl-EZE® and 2% Eudragit® RL should fall into the region between hypothetical curve #1 and #2 (FIGS. 8-11). Dissolution tests are also performed on copper gluconate minitablets coated with 3% Opadry®, 4% Eudragit® FS, and 2% Eudragit® RL. Copper in the minitablets is intended to be released in ileum/colon for patients with and without treatment of PPIs (neutral or acidic stomach pH, respectively). The 2% Eudragit® RL coating gives additional 2-3 hour delay on copper release beyond the 2 hour protection from acid provided by Eudragit® FS alone. The actual dissolution profile of copper gluconate with 4% Eudragit® FS and 2% Eudragit® RL should fall into the region between hypothetical curve #1 and #2 (FIGS. 8-11).

TABLE 18

Dissolution tests on capsules with Copper Gluconate and/or Disulfiram minitablet coated with Opadry ® (4.5% W.G.) and Eudragit ® FS 30 D (12% W.G.) at Time = 0

| Dissolution tests | API | Capsule Configuration | % Drug Recovery | | | |
|---|---|---|---|---|---|---|
| | | | 2 h (T0) 0.1N HCl | 1 h | 2.5 h | 3.5 h |
| | | | | Sodium Citrate pH 7.4 | | |
| Copper gluconate coated with Opadry ®(4.5% W.G.) | Cu Gluconate (coated) | 3x tablets | 105.44 ± 0.020% | 4.44 ± 0.010% | 6.67 ± 0.024% | 6.96 ± 0.020% |
| Copper gluconate coated with Opadry ® (4.5% W.G.) and Eudragit ® FS 30 D (12% W.G.) | Cu Gluconate (coated) | 3x tablets | 3.22 ± 0.007% | 4.67 ± 0.003% | 72.80 ± 0.162% | 98.70 ± 0.057% |
| Copper gluconate coated with Opadry ® (4.5% W.G.) and Eudragit ® FS30D (12% W.G.) | Cu Gluconate (coated) | 3x tablets | NP | NP | NP | NP |
| Uncoated disulfiram, 10 mg | Disulfiram (uncoated) | 2x tablets | | | | |

Table 18 Legend:
1. Data are presented as Mean ± SD (N = 3 capsules); NP: not performed;
2. Normal dissolution testing on Copper Gluconate was performed at 37° C., 50 rpm, and 50 mL of dissolution media (0.1N HCl or Sodium Citrate pH 7.4) per SOP QC-223;
3. Eudragit ® FS 30 D is a pH-dependent enteric polymer used to release the drug at the solution with pH value above 7

TABLE 19

Dissolution tests on capsules with Copper Gluconate and/or Disulfiram minitablet coated with Opadry ® (4.5% W.G.), Eudragit ® FS 30 D (12% W.G.) and Eudragit ® RL (2%, 4% and 6% W.G.) at Time = 0 (T0)

| Dissolution tests | Eudragit ® RL coating | Capsule Config-uration | % Drug Recovery | | | | | | |
|---|---|---|---|---|---|---|---|---|---|
| | | | 1 h | 2 h | 2.5 h | 3 h | 3.5 h | 4 h | 8 h |
| | | | | | Sodium Citrate pH 7.4 | | | | |
| Copper gluconate coated with Opadry ® (4.5% W.G.), and Eudragit ® FS30D (12% W.G.) | 0% | 3x tablets | 5.24 | 25.88 | 74.49 | 91.40 | 86.75 | 88.37 | 91.03 |
| Copper gluconate coated with Opadry ® (4.5% W.G.), Eudragit ® FS30D (12% W.G.), and Eudragit ® RL30D (2% W.G.) | 2% | 3x tablets | 4.09 ± 0.834% | 3.78 ± 0.829% | 3.93 ± 1.254% | 3.97 ± 0.138% | 7.57 ± 6.128% | 13.77 ± 11.672% | 91.95 ± 0.635 |
| Copper gluconate coated with Opadry ® (4.5% W.G.), Eudragit ® FS30D (12% W.G.), and Eudragit ® RL30D (4% W.G.) | 4% | 3x tablets | 5.06 ± 2.040% | 3.93 ± 3.219% | 7.64 ± 0.972% | 6.43 ± 6.736% | 12.20 ± 8.758% | 9.61 ± 8.837% | 56.44 ± 9.765% |

TABLE 19-continued

Dissolution tests on capsules with Copper Gluconate and/or Disulfiram minitablet coated with Opadry ® (4.5% W.G.), Eudragit ® FS 30 D (12% W.G.) and Eudragit ® RL (2%, 4% and 6% W.G.) at Time = 0 (T0)

| | Eudragit ® | Capsule | % Drug Recovery | | | | | | |
|---|---|---|---|---|---|---|---|---|---|
| Dissolution tests | RL coating | Config-uration | 1 h | 2 h | 2.5 h | 3 h | 3.5 h | 4 h | 8 h |
| | | | | | Sodium Citrate pH 7.4 | | | | |
| Copper gluconate coated with Opadry ® (4.5% W.G.), Eudragit ® FS30D (12% W.G.), and Eudragit ® RL30D (6% W.G.) | 6% | 3x tablets | 3.36 ± 0.882% | 5.07 ± 0.853% | 5.27 ± 0.136% | 7.22 ± 3.528% | 4.98 ± 1.590% | 4.16 ± 0.090% | 20.39 ± 4.130% |

Table 19 Legend:
1. Data are presented as Mean ± SD (N = 3 capsules); NP: not performed;
2. Normal dissolution testing on Copper Gluconate was performed at 37° C., 50 rpm, and 50 mL of dissolution media (0.1N HCl or Sodium Citrate pH 7.4;
3. Eudragit ® FS 30 D is a pH-dependent enteric polymer used to release the drug at the solution with pH value above 7

TABLE 20

Dissolution testing on Copper Gluconate micro tablets coated with Opadry ® (3% W.G.) and Eudragit ® FS 30 D (4 or 6% W.G.) at Time 0 (T0)

| | Capsule | % Drug Recovery at T0 | | | | | | |
|---|---|---|---|---|---|---|---|---|
| Dissolution tests | Config-uration | 2 h 0.1N HCl | 1 h | 1.5 h | 2 h | 2.5 h | 3 h | 3.5 h |
| | | | | | Sodium Citrate pH 7.4 | | | |
| Copper gluconate coated with Opadry ® (3% W.G.), and Eudragit ® FS 30D (4% W.G.) | 3x tablets | 2.36 ± 1.231% | 40.37 ± 4.955% | 74.46 ± 8.048% | 88.18 ± 5.851% | 95.43 ± 5.269% | 95.44 ± 4.602% | 100.24 ± 3.864% |
| Copper gluconate coated with Opadry ® (3% W.G.), and Eudragit ® FS 30D (6% W.G.) | 3x tablets | 3.60 ± 1.384% | 19.10 ± 2.463% | 19.10 ± 13.107% | 61.02 ± 7.687% | 88.48 ± 4.166% | 96.23 ± 4.219% | 98.95 ± 3.630% |

Table 20 Legend:
1. W.G.: weight gain;
2. Data are presented as Mean ± SD (N = 3 capsules);
3. Normal dissolution testing on Copper Gluconate was performed at 37° C., 50 rpm, and 50 mL of dissolution media (Sodium Citrate pH 7.4) per SOP QC-223

TABLE 21

Summary of Dissolution tests of Coated Copper Gluconate Tablets

| Configuration of Tablet | Description of Results |
|---|---|
| Copper gluconate tablets with Acryl-EZE ® (20% weight gain); | Good protection from acid; Break point of Acryl-EZE ®: pH 5.5 or above; No release in 0.1N HCl, 80% or above release after 2 h in citrate buffer, pH 6.0 (T0, 1M, 2M, 3M) |
| Copper gluconate tablets with Eudragit ® RL/RS (8:2 ratio) (2%, 6%, 10% weight gain) | Unsatisfactory protection from acid; 2% RL/RS: complete release after 2.5 h of testing; 6% RL/RS: complete release after 3.0 h of testing; 10% RL/RS: 70% release after 3.0 h of testing |
| Copper gluconate tablets with Eudragit ® FS (12% weight gain); | Good protection from acid; Break point of Eudragit ® FS: pH 7.0 or above; No release in 0.1N HCl, 80% or above release after 3 h in sod. citrate, pH 7.4 |
| Copper gluconate tablets with Eudragit ® FS (12% weight gain) and Eudragit ® RL (2% weight gain) | No release in 0.1N HCl, 91.03% drug recovery at the 3 h time point in sod. citrate, pH 7.4 |
| Copper gluconate tablets with Eudragit ® FS (12% weight gain) and Eudragit ® RL (4% weight gain) | No release in 0.1N HCl, 56.44% drug recovery at the 3 h time point in sod. citrate, pH 7.4 |
| Copper gluconate tablets with Eudragit ® FS (12% weight gain) and Eudragit ® RL (6% weight gain) | No release in 0.1N HCl, 20.39% drug recovery at the 3 h time point in sod. citrate, pH 7.4 |

TABLE 21-continued

Summary of Dissolution tests of Coated Copper Gluconate Tablets

| Configuration of Tablet | Description of Results |
|---|---|
| Copper gluconate tablets with Eudragit ® FS (4% weight gain) | No release in 0.1N HCl, 88.18% drug recovery at the 2 h time point in sod. citrate, pH 7.4 |

5.5.6. Example 6: Copper Gluconate and Disulfiram Individual Capsule Formulations While the staggered delivery unit dosage form was under development, disulfiram and copper gluconate were separately formulated in individual capsules (Tables 22 and 23), each designed for immediate release upon ingestion, to be used in a clinical trial testing staggered administration of disulfiram and copper for treatment of cancer (see Example 7).

Copper Gluconate Capsule Formulation

TABLE 22

Copper gluconate capsule formulation

| Ingredients | % w/w | Amount (mg) per capsule | Amount (g) for 26667 Capsules | Actual Amount (g) Weighed |
|---|---|---|---|---|
| Copper gluconate low heavy metalpowder | 11.60 | 10.71 | 285.6 | 285.63 |
| Lactose anhydrous (Supertab 21AN) | 40.65 | 37.5 | 1000 | 1000.01 |
| Microcrystaline cellulose (MCC) 101 | 40.65 | 37.5 | 1000 | 1000.02 |
| Croscarmellose Sodium | 6.11 | 5.64 | 150.4 | 150.4 |
| Magnesium Stearate | 0.48 | 0.45 | 12 | 12.0 |
| Cab-O-Sil | 0.48 | 0.45 | 12 | 12.0 |
| Total | 100 | 92.25 | 2460 | 2460.06 |

All the materials were sifted through 30 mesh and blended for 25 minutes. The blends were tested for blend uniformity analysis (Table 24).

Disulfiram Capsule Formulation

TABLE 23

Disulfiram capsule formulation

| Ingredients | % w/w | Amount (mg) per capsule | Amount (g) for 20000 Capsules | Actual Amount (g) Weighed |
|---|---|---|---|---|
| Disulfiram | 32.52 | 40 | 800 | 800.16 |
| Lactose anhydrous (Supertab 21AN) | 32.52 | 40 | 800 | 800.02 |
| MCC 101 | 32.52 | 40 | 800 | 799.59 |
| Croscarmellose Sodium | 6.34 | 7.8 | 156 | 156.0 |
| Magnesium Stearate | 0.48 | 0.6 | 12 | 12.0 |
| Cab-O-Sil | 0.48 | 0.6 | 12 | 12.0 |
| Total | 100 | 129 | 2580 | 2579.77 |

All the materials were sifted through 30 mesh and blended for 25 minutes. The blend was tested for blend uniformity analysis (Table 24).

Analytical Results of Moisture Content

Moisture content of the disulfiram and copper gluconate blends was tested on an LOD analyzer. The moisture content of the disulfiram blend was 2.27% (Initial). The moisture content of the copper gluconate blend was 2.46% (Initial).

Determination of Blend Uniformity

TABLE 24

Blend uniformity analysis of Disulfiram & Copper gluconate blends

| Sample No. | % Recovery of disulfiram (25 minutes blending) | % Recovery of copper gluconate (25 minutes blending) | % Recovery of copper gluconate (55 minutes blending) |
|---|---|---|---|
| 1 | 102.9 | 93.5 | 86.9 |
| 2 | 105.3 | 91.9 | 100.3 |
| 3 | 99.2 | 93.1 | 92.4 |
| 4 | 107.9 | 90.6 | 90.5 |
| 5 | 103.3 | 91.0 | 91.5 |
| 6 | 102.6 | 94.0 | 96.5 |
| Average | 103.5 | 92.3 | 93.0 |

5.5.7. Example 7: Clinical Study of Disulfiram and Copper Staggered Oral Dosing Regimen for the Treatment of Recurrent Glioblastoma A phase II, multicenter, open-label, single-arm study is performed (ClinicalTrials.gov Identifier: NCT03034135) to confirm the safety, tolerability, and efficacy of a staggered oral dosing regimen of disulfiram and copper gluconate for treatment of recurrent, temozolomide-resistant, glioblastoma.

Patients with temozolomide ("TMZ")-resistant glioblastoma are treated with disulfiram and copper gluconate on a staggered oral dosing regimen to assess re-sensitization of the glioblastoma to TMZ (FIG. 12). TMZ is administered daily on days 1-5 of a 28 day cycle at a dose of 150-200 mg/m$^2$ PO. Two capsules of 40 mg each of disulfiram are administered orally thrice daily ("TID") (total of 240 mg per day) approximately 4-8 hours apart in a 28 day cycle. A capsule of 1.5 mg copper gluconate is administered orally TID (total of 4.5 mg per day) with meals, and not within one hour of the oral administration of disulfiram, TID in a 28 day cycle.

The results of the clinical trial demonstrate that an oral dosing regimen in which disulfiram and copper gluconate are administered on a staggered oral dosing schedule is capable of resensitizing temozolomide-resistant recurrent glioblastoma to temozolomide.

5.5.8. Example 8: Clinical Study of Disulfiram and Copper Staggered Oral Dosing Regimen for the Treatment of Metastatic Pancreatic Cancer A phase II, open label, randomized study with two study arms is performed to confirm the anti-cancer effect of DSF-Cu in combination with gemcitabine and nab-Paclitaxel in patients with metastatic pancreatic cancer.

Study Objectives:

The objectives of the study are to evaluate progression-free survival (PFS) according to Response Evaluation Criteria in Solid Tumors (RECIST) Guidelines Version 1.1, to evaluate changes in plasma levels of CA19-9 from baseline as a marker of tumor response, to evaluate the safety and tolerability of gemcitabine+nab-paclitaxel with or without DSF-Cu in this patient population, to evaluate the objective tumor response according to RECIST guidelines, to evaluate overall survival, and to evaluate changes from baseline for serum albumin and body weight.

Overall Study Design: Open label, randomized study with two study arms:

Treatment A:

25 subjects receive Nab-paclitaxel+gemcitabine+DSF-CU. Nab-paclitaxel 125 mg/m$^2$ is administered by IV over 30 minutes followed by administration of gemcitabine by IV infusion at 1000 mg/m$^2$ over 30 minutes. Nab-paclitaxel+gemcitabine is given weekly for 3 weeks followed by one week of rest. Patients take 80 mg DSF TID with approximately 8 ounces of water at least one hour before food. Copper gluconate is taken at a dose of 1.5 mg with meals TID and not within one hour of DSF.

Treatment B:

25 subjects receive Nab-paclitaxel+gemcitabine. Nab-paclitaxel 125 mg/m2 is administered by IV over 30 minutes followed by administration of gemcitabine by IV infusion at 1000 mg/m$^2$ over 30 minutes. Nab-paclitaxel+gemcitabine will be given weekly for 3 weeks followed by one week of rest. Patients take 80 mg DSF TID with approximately 8 ounces of water at least one hour before food. Copper gluconate is taken at a dose of 1.5 mg with meals TID and not within one hour of DSF.

Patient Inclusion Criteria

Patients enrolled in the study have histologically confirmed adenocarcinoma of the pancreas that is metastatic and for which potential curative measures, such as resection of an isolated metastasis, are not available. Patients have received FOLFIRINOX combination chemotherapy and either have developed progressive disease or intolerance to the FOLFIRINOX regimen. Patients may not have received a second line chemotherapy regimen after developing progressive disease or intolerance to the FOLFIRINOX regimen. Patients have one or more metastatic tumors measurable by CT scan. Patients have measurable disease, defined as at least one lesion that can be accurately measured in at least one dimension (longest diameter to be recorded for non-nodal lesions and short axis for nodal lesions) as ≥20 mm with conventional techniques or as ≥10 mm with spiral CT scan. Patients are male or non-pregnant and non-lactating female and ≥18 to ≤80 years of age. Patients have adequate biological parameters as demonstrated by the following blood counts at Screening (obtained ≤14 days prior to randomization) and at Baseline-Day 0: Absolute neutrophil count (ANC) ≥1.5×10$^9$/L; Platelet count ≥100,000/mm$^3$ (100×10$^9$/L); Hemoglobin (Hgb) ≥9 g/dL. Patients have the following blood chemistry levels at Screening (obtained ≤14 days prior to randomization) and at Baseline-Day 0: AST (SGOT), ALT (SGPT)≤2.5×upper limit of normal range (ULN), unless liver metastases are present, then ≤5×ULN is allowed. Total bilirubin ≤1.5×ULN. Patients have ECOG performance status from 0 to ≤2.

The results of the clinical trial demonstrate that an oral dosing regimen in which disulfiram and copper gluconate are administered on a staggered oral dosing schedule is capable of increasing PFS when added to the standard of care regimen of Nab-paclitaxel+gemcitabine.

5.5.9. Example 9: Clinical Study of the Efficacy of Disulfiram and Copper Staggered Oral Dosing Regimen in Combination with Chemoradiotherapy in Patients with Locally Advanced Rectal Cancer A phase II, open label, randomized study, with two study arms is performed to confirm the anti-cancer effect of DSF-Cu in combination with chemoradiotherapy in patients with locally advanced rectal cancer.

Study Objectives

The primary objective is to confirm an antitumor effect of DSF-Cu in combination with chemoradiotherapy as determined by the incidence of pathologic complete response (no evidence of residual cancer) at the time of surgery. Secondary Objectives are to determine evidence of an antitumor effect of DSF-Cu in combination with chemoradiotherapy as determined by: safety of DSF-Cu in combination with chemoradiotherapy as determined by toxicity assessment according to NCI CTCAE V.4.0, tumor down staging, tumor regression, R0 resection rate; negative circumferential resection rate, and rate of sphincter-sparing surgery.

Overall Study Design: Open label, randomized study with two study arms:

Subjects with locally advanced (T3 or T4 or node positive) rectal adenocarcinoma are enrolled into the study and receive chemoradiotherapy consistent with the institutional standard of care. During a run-in period, 10 subjects are enrolled to receive chemoradiotherapy+DSF-Cu to assess compatibility of the combination and then 50 subjects are randomized to an open label, controlled period with two arms at a ratio of 1:1 to receive: chemoradiotherapy+DSF-Cu, or chemoradiotherapy without DSF-Cu. After the 10$^{th}$ subject has been enrolled and has been followed up until one month post-surgery or the last dose of DSF-Cu+chemoradiotherapy, whichever is first, data from the 10 subjects enrolled in the study are reviewed by the investigators that enrolled the subjects in the study as well as Cantex management (Dr. Stephen Marcus) to assess the safety of the administration of chemoradiation+DSF-Cu and recommend whether continuation with the Randomized Period of the study is indicated.

Treatment A

Chemoradiotherapy is administered in accordance with the institutional standard of care along DSF at 80 mg TID and 1.5 mg of Cu TID. The DSF and copper doses are administered sequentially, with each DSF dose administered at least one hour before the administration of copper.

Treatment B

Chemoradiotherapy is administered in accordance with the institutional standard of care without DSF-Cu.

Ongoing Safety Assessment during the Treatment Period of the Study. If, at any point, there appears to be a 25% or greater increase in the expected/reported incidence of grade 3 or 4 toxicities, accrual is held, and dose modification or study discontinuation is considered.

Patient Inclusion Criteria

Patients must have histologically confirmed adenocarcinoma of the rectum with pathological material reviewed by the Department of Pathology at MDACC. The clinical stage must be T3, T4, or node positive T1 or 2. Patients must have no evidence of metastatic disease. Patient is Male or a non-pregnant and non-lactating female and ≥18 to ≤80 years of age. Patient has adequate biological parameters as demonstrated by the following blood counts at Screening (obtained ≤14 days prior to randomization) and at Baseline-Day 0: Absolute neutrophil count (ANC) ≥1.5×10$^9$/L; Platelet count ≥100,000/mm$^3$ (100×10$^9$/L); Hemoglobin (Hgb) ≥9 g/dL. Patient has the following blood chemistry levels at Screening (obtained ≤14 days prior to randomization) and at Baseline-Day 0: AST (SGOT), ALT (SGPT)≤2.5×upper limit of normal range (ULN), unless liver metastases are present, then ≤5×ULN is allowed. Total bilirubin ≤1.5× ULN. Patient has ECOG performance status from 0 to 2. Patient has been informed about the nature of the study, and has agreed to participate in the study, and signed the Informed Consent Form (ICF) prior to participation in any study-related activities.

5.5.10. Example 10: Disulfiram and Zinc Gluconate Form a Precipitate at Low pH Compatibility of disulfiram and zinc gluconate for simultaneous oral administration was assessed. 5 mg of zinc gluconate and 40 mg of disulfiram were mixed in 50 mL volumetric flasks, and 0.1N HCl was added to the flasks. The solution was observed for color development after storage at 25° C./ambient humidity for 2 days (FIG. 9). A control was run in parallel: 0.1N HCl solution containing 50 mg of zinc gluconate alone. There was no color change observed in the 0.1N HCl solutions containing the mixture of zinc gluconate and disulfiram or zinc gluconate alone. However, the 0.1N HCl solution containing zinc gluconate and disulfiram showed a white precipitate in the bottom of the volumetric flask at T0 and T=2 days. The 0.1N HCl solution containing 50 mg of zinc gluconate alone remained clear throughout the entire study. The results after storage for 2 days at 25° C. are shown in FIG. 13.

Stability of disulfiram and zinc gluconate was tested after 4 weeks at 40° C. in 0.1 N HCl. (Table 24). The percent recovery of disulfiram after 4 weeks combined with zinc gluconate was 80.51% while the percent recovery of disulfiram after 4 weeks combined with copper gluconate was 83.03%. These results demonstrate that disulfiram is unstable in the presence of zinc gluconate.

TABLE 24

Stability of zinc gluconate and disulfiram after 4 weeks @ 40° C./75% RH

| Sample | RT | PA | Conc. (mg/mL) | Actual Conc. (mg/mL) | % Recovery |
|---|---|---|---|---|---|
| DSF | 3.4 | 1158244 | 0.040 | 0.040 | 99.28 |
| DSF + Zinc Gluconate | 3.5 | 943896 | 0.032 | 0.040 | 80.51 |

TABLE 24-continued

Stability of zinc gluconate and disulfiram after 4 weeks @ 40° C./75% RH

| Sample | RT | PA | Conc. (mg/mL) | Actual Conc. (mg/mL) | % Recovery |
|---|---|---|---|---|---|
| DSF + Copper Gluconate | 3.5 | 973035 | 0.033 | 0.040 | 83.03 |

It is known that the zinc and DSF must be administered in sufficient temporal proximity to allow formation of zinc-disulfiram complexes. However, the formation of the white precipitate indicates that simultaneous oral administration of disulfiram and zinc would provide poor bioavailability of both active ingredients, leading us to conclude that staggered oral administration is preferable to ensure maximal bioavailability, and may in fact be required to achieve therapeutic levels of the zinc-disulfiram complexes in vivo.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. An oral dosage form configured to temporally stagger release of disulfiram ("DSF") and copper after ingestion, wherein the copper is released following the release of DSF, is formulated to be released greater than 30 minutes after the release of DSF, and is in the form of copper gluconate or copper glycinate.

2. An oral dosage form configured to temporally stagger release of disulfiram ("DSF") and copper after ingestion, wherein the copper is released following the release of DSF, wherein the DSF is formulated to be released in the stomach of the subject and wherein the copper is in the form of copper gluconate or copper glycinate and is coated with an enteric coating or a gastro-resistant coating.

* * * * *